US012616421B2

(12) United States Patent
Nierenberg et al.

(10) Patent No.: US 12,616,421 B2
(45) Date of Patent: May 5, 2026

(54) SYSTEM AND METHOD FOR GENERATING A PROBABILITY VALUE FOR AN EPILEPTIFORM ABNORMALITY BY NEURAL NETWORK TO IDENTIFY SIGNAL SPIKES

(71) Applicant: Persyst Development Corporation, Solana Beach, CA (US)

(72) Inventors: Nicolas Nierenberg, La Jolla, CA (US); Scott B. Wilson, Del Mar, CA (US); Mark L. Scheuer, Wexford, PA (US)

(73) Assignee: Persyst Development Corporation, Solana Beach, CA (US)

( * ) Notice: Subject to any disclaimer, the term of this patent is extended or adjusted under 35 U.S.C. 154(b) by 286 days.

(21) Appl. No.: 18/225,322

(22) Filed: Jul. 24, 2023

(65) Prior Publication Data

US 2023/0368023 A1 Nov. 16, 2023

Related U.S. Application Data

(63) Continuation of application No. 17/175,635, filed on Feb. 13, 2021, now Pat. No. 11,803,753, which is a continuation of application No. 16/101,485, filed on Aug. 12, 2018, now Pat. No. 10,929,753, which is a (Continued)

(51) Int. Cl.

*G06N 3/08* (2023.01)
*A61B 5/00* (2006.01)
*A61B 5/31* (2021.01)
*A61B 5/384* (2021.01)

(52) U.S. Cl.

CPC .............. *A61B 5/7267* (2013.01); *A61B 5/31* (2021.01); *A61B 5/384* (2021.01); *A61B 5/7203* (2013.01)

(58) Field of Classification Search

CPC . G06N 3/08; G06N 3/084; A61B 5/31; A61B 5/384; A61B 5/7203; A61B 5/374; A61B 5/4094; A61B 5/7267; A61B 5/7275; G16H 50/20

See application file for complete search history.

(56) References Cited

U.S. PATENT DOCUMENTS

| | | | |
|---|---|---|---|
| RE30,502 | E | 2/1981 | Lencioni, Jr. |
| 4,550,736 | A | 11/1985 | Broughton et al. |
| 4,644,956 | A | 2/1987 | Morgenstern |

(Continued)

FOREIGN PATENT DOCUMENTS

| | | |
|---|---|---|
| EP | 0013183 | 7/1980 |
| EP | 0898460 | 8/2006 |

(Continued)

OTHER PUBLICATIONS

Teplan, Fundamentals of EEG Measurement, Measurement Science Review, vol. 2, Section 2, 2002.

(Continued)

*Primary Examiner* — Serkan Akar

(74) *Attorney, Agent, or Firm* — Clause Eight; Michael Catania

(57) ABSTRACT

A method and system for generating a probability value for an event. The system includes a source for generating a plurality of digital input signals, a processor connected to the source to receive the plurality of digital input signals from the source, and a display connected to the processor for displaying a final output. Preferably, the method further includes validating the probability value.

4 Claims, 48 Drawing Sheets

300

Related U.S. Application Data continuation of application No. 14/222,655, filed on Mar. 23, 2014, now abandoned.

(60) Provisional application No. 61/929,120, filed on Jan. 20, 2014.

(56) References Cited

U.S. PATENT DOCUMENTS

| | | | |
|---|---|---|---|
| 4,709,702 | A | 12/1987 | Sherwin |
| 4,936,306 | A | 6/1990 | Doty |
| 4,967,038 | A | 10/1990 | Gevins et al. |
| 5,038,782 | A | 8/1991 | Gevins et al. |
| 5,230,344 | A | 7/1993 | Ozdamar et al. |
| 5,230,346 | A | 7/1993 | Leuchter et al. |
| 5,305,746 | A | 4/1994 | Fendrock |
| 5,309,909 | A | 5/1994 | Gadsby et al. |
| 5,520,191 | A | 5/1996 | Karlsson et al. |
| 5,626,145 | A | 5/1997 | Clapp et al. |
| 5,687,286 | A | 11/1997 | Bar-Yam |
| 5,721,807 | A | 2/1998 | Tschirk |
| 5,730,146 | A | 3/1998 | Itil et al. |
| 5,846,208 | A | 12/1998 | Pichlmayr et al. |
| 5,859,925 | A | 1/1999 | Yaeger et al. |
| 5,983,128 | A | 11/1999 | Baudonniere et al. |
| 6,201,982 | B1 | 3/2001 | Menkes et al. |
| 6,224,549 | B1 | 5/2001 | Drongelen |
| 6,334,856 | B1 | 1/2002 | Allen et al. |
| 6,493,576 | B1 | 12/2002 | Dankwart-Eder |
| 6,591,132 | B2 | 7/2003 | Gotman et al. |
| 6,602,202 | B2 | 8/2003 | John |
| 6,735,467 | B2 | 5/2004 | Wilson |
| 6,931,274 | B2 | 8/2005 | Williams |
| 7,170,418 | B2 | 1/2007 | Rose-Pehrsson et al. |
| 7,286,871 | B2 | 10/2007 | Cohen |
| 7,460,905 | B2 | 12/2008 | Mase et al. |
| 7,672,717 | B1 | 3/2010 | Zikov et al. |
| 7,754,190 | B2 | 7/2010 | Suffin |
| 7,809,433 | B2 | 10/2010 | Keenan |
| 7,904,144 | B2 | 3/2011 | Causevic et al. |
| 7,941,201 | B2 | 5/2011 | Chiou et al. |
| 8,112,141 | B2 | 2/2012 | Wilson et al. |
| 8,155,736 | B2 | 4/2012 | Sullivan et al. |
| 8,185,183 | B1 | 5/2012 | Wilson et al. |
| 8,271,065 | B1 | 9/2012 | Wilson et al. |
| 8,428,681 | B2 | 4/2013 | Wilson et al. |
| 8,447,407 | B2 | 5/2013 | Talathi et al. |
| 8,538,502 | B1 | 9/2013 | Wilson et al. |
| 8,666,484 | B2 | 3/2014 | Nierenberg et al. |
| 8,694,070 | B2 | 4/2014 | Wilson |
| 8,744,808 | B2 | 6/2014 | Lee |
| 8,972,001 | B2 | 3/2015 | Nierenberg et al. |
| 9,055,927 | B2 | 6/2015 | Wilson et al. |
| 9,232,922 | B2 | 1/2016 | Wilson et al. |
| 9,563,740 | B2 | 2/2017 | Abdelghani et al. |
| 9,592,389 | B2 | 3/2017 | Moffitt |
| 10,022,291 | B2 | 7/2018 | Wilson et al. |
| 10,105,091 | B2 | 10/2018 | Papay et al. |
| 10,939,839 | B2 | 3/2021 | Baker et al. |
| 10,945,622 | B2 | 3/2021 | Sohrabpour et al. |
| 2002/0082513 | A1 | 6/2002 | Ennen et al. |
| 2002/0082551 | A1 | 6/2002 | Ennen et al. |
| 2002/0099306 | A1 | 7/2002 | Shaw et al. |
| 2003/0144600 | A1 | 7/2003 | Yarita |
| 2003/0144601 | A1 | 7/2003 | Prichep |
| 2004/0059215 | A1 | 3/2004 | Nishimura et al. |
| 2004/0059241 | A1 | 3/2004 | Suffin |
| 2004/0077967 | A1 | 4/2004 | Jordan |
| 2004/0152957 | A1 | 8/2004 | Stivoric et al. |
| 2004/0199482 | A1 | 10/2004 | Wilson |
| 2004/0249258 | A1 | 12/2004 | Tupin |
| 2005/0059874 | A1 | 3/2005 | Fuchs et al. |
| 2005/0107716 | A1 | 5/2005 | Eaton et al. |
| 2005/0144042 | A1 | 6/2005 | Joffe et al. |
| 2006/0100530 | A1 | 5/2006 | Kliot et al. |
| 2007/0032737 | A1 | 2/2007 | Causevic et al. |
| 2007/0066914 | A1 | 3/2007 | Le et al. |
| 2007/0135727 | A1 | 6/2007 | Virtanen et al. |
| 2007/0167858 | A1 | 7/2007 | Virtanen et al. |
| 2007/0173733 | A1 | 7/2007 | Le et al. |
| 2008/0027515 | A1 | 1/2008 | Harris et al. |
| 2008/0249430 | A1 | 10/2008 | John et al. |
| 2008/0249431 | A1 | 10/2008 | Bier et al. |
| 2008/0262335 | A1 | 10/2008 | Sun et al. |
| 2008/0262367 | A1 | 10/2008 | Mugler et al. |
| 2008/0269630 | A1 | 10/2008 | Denison et al. |
| 2008/0273709 | A1 | 11/2008 | Thiagarajan et al. |
| 2008/0294031 | A1 | 11/2008 | Wilson et al. |
| 2009/0054743 | A1 | 2/2009 | Stewart |
| 2009/0062680 | A1 | 3/2009 | Sandford |
| 2009/0222369 | A1 | 9/2009 | Zoldi et al. |
| 2009/0247895 | A1 | 10/2009 | Morikawa et al. |
| 2009/0264786 | A1 | 10/2009 | Jacquin |
| 2009/0287107 | A1 | 11/2009 | Nielsen et al. |
| 2010/0010364 | A1 | 1/2010 | Verbitskiy |
| 2010/0036276 | A1 | 2/2010 | Ochs |
| 2010/0036672 | A1 | 2/2010 | Li et al. |
| 2010/0060350 | A1 | 3/2010 | Zhang et al. |
| 2010/0098289 | A1 | 4/2010 | Tognoli et al. |
| 2010/0249638 | A1 | 9/2010 | Liley |
| 2011/0015503 | A1 | 1/2011 | Joffe et al. |
| 2011/0015537 | A1 | 1/2011 | Virkkala et al. |
| 2011/0105939 | A1 | 5/2011 | Yong et al. |
| 2011/0112426 | A1 | 5/2011 | Causevic |
| 2011/0125046 | A1 | 5/2011 | Burton et al. |
| 2011/0130675 | A1 | 6/2011 | Bibian |
| 2011/0144520 | A1 | 6/2011 | Causevic |
| 2011/0166434 | A1 | 7/2011 | Gargiulo |
| 2011/0178421 | A1 | 7/2011 | Schultz |
| 2011/0224569 | A1 | 9/2011 | Isenhart et al. |
| 2012/0089004 | A1 | 4/2012 | Hsu et al. |
| 2012/0101401 | A1 | 4/2012 | Faul |
| 2012/0277618 | A1 | 11/2012 | Giftakis et al. |
| 2013/0096450 | A1 | 4/2013 | Duckert et al. |
| 2013/0204755 | A1 | 8/2013 | Zoldi et al. |
| 2013/0261490 | A1 | 10/2013 | Truccolo et al. |
| 2013/0267873 | A1 | 10/2013 | Fuchs |
| 2014/0005563 | A1 | 1/2014 | Ramanathan et al. |
| 2015/0112223 | A1 | 4/2015 | Nierenberg et al. |
| 2015/0351654 | A1 | 12/2015 | Kilsgaard et al. |
| 2016/0120457 | A1 | 5/2016 | Wu et al. |
| 2017/0178324 | A1 | 6/2017 | Saget et al. |
| 2017/0332933 | A1 | 11/2017 | Krishnaswamy et al. |
| 2018/0221644 | A1 | 8/2018 | Grill et al. |
| 2018/0296167 | A1 | 10/2018 | Stewart et al. |
| 2020/0054888 | A1 | 2/2020 | Etkin et al. |

FOREIGN PATENT DOCUMENTS

| | | |
|---|---|---|
| JP | 11318843 | 11/1999 |
| JP | 2006109964 | 4/2006 |
| RU | 2415642 | 4/2011 |
| WO | WO2007144307 | 12/2007 |
| WO | WO2008038194 | 4/2008 |
| WO | WO2008057365 | 5/2008 |
| WO | WO2008058343 | 5/2008 |
| WO | WO2008061292 | 5/2008 |
| WO | WO2009144655 | 12/2009 |
| WO | WO2010107473 | 9/2010 |
| WO | WO2010115939 | 10/2010 |
| WO | WO2011088227 | 7/2011 |

OTHER PUBLICATIONS

Intl. search Report For PCT Application PCT/US2021/033916, mailed Aug. 26, 2021.

Written Opinion For PCT Application PCT/US2021/033916, mailed Aug. 26, 2021.

Intl. Search Report and Written Opinion for PCT Application PCT/US2019/020433, mailed on May 31, 2019.

EEG-Based neonatal seizure detection with Support Vector Machines, Clinical Neurophysiology, 122(3) 464-473, Mar. 2011.

(56) References Cited

OTHER PUBLICATIONS

Zainuddin et al., Reliable Epileptic Seizure Detection Using An Improved Wavelet Neural Network, Australasian Medical Journal, 2013, 6, 5, 308-314.
Osorio et al., Pharmaco-resistant seizures: self-triggering capacity scale-free properties and predictability, European Journal Of Neuroscience, vol. 30, pp. 1554-1558, 2009.
Intl. Search Report and Written Opinion for PCT Application PCT/US2014/061433, mailed on Feb. 5, 2015.
Statistica Automated Neural Networks, URL:httpwwwstatsoftcom/product/STATISTICA/Automated-Neural -Networks, Jul. 4, 2013.
Neyronnye seti, Statsoft Elecktronny uchebnik po statisike, URL:httpwwwstatsoft.ru/home/textbook/modules/stneunethtml, May 18, 2013.
Office Action for U.S. Appl. No. 13/831,609, mailed on Oct. 15, 2015.
Office Action for U.S. Appl. No. 13/830,742, mailed on Mar. 18, 2016.
Office Action for U.S. Appl. No. 13/542,665, mailed on Jan. 15, 2013.
Office Action for U.S. Appl. No. 13/620,784, mailed on Jan. 7, 2013.
International Search Report for PCT Application PCT/US2012/055692.
International Search Report for PCT Application PCT/US2012/066480, mailed on Feb. 11, 2013.
Patentability Report for PCT Application PCT/US2012/066480, mailed on Feb. 11, 2013.
Gao et al., Automatic Removal Of Various Artifact From EEG Signals Uisng Combined Methods, Journal of Clinical Neurophysiology, vol. 27, No. 5, Oct. 2010.
European Patent Office search Report for European Patent Application 12833897.7, Feb. 5, 2015.
European Patent Office search Report for European Patent Application 12851532.7, Jul. 1, 2015.
Intl. search Report and Written Opinion for PCT Application PCT/US2014/020933, mailed Jun. 3, 2014.
A Garces Correa et al. Artifact removal from EEG signals using adaptive filters in cascade. 2007 Issue 1. Journal of Physics: Conference Series 90 0I2081. 16th Argentine Bioengineering Congress and the 5th Conference of Clinical Engineering. IOP Publishing. abstract, p. 1, par.2.
Saied Sanei et al. EEG Signal Processing. Centre of Digital Signal Processing. Cardiff University. 2007. John Wiley & Sons Ltd., Bicentennial. UK. p. 87.
Ricardo A. Salido Ruiz et al. EEG montage analysis in the Blind Source Separation framework. Preprint submitted to Biomedical Signal Processing and Control. May 5, 2010. p. 3,par.3,p. 20, par.4, p. 22,par.1,p. 26,par. 1, p. 24, par.1,2, tabl. 1, Fig.2,4.
Intl. search Report for PCT/US2012/055692, filed Sep. 17, 2012.
Intl. Written Opinion for PCT/US2012/066471, filed Nov. 23, 2012.
Intl. Search Report for PCT/US2012/066471, filed Nov. 23, 2012.
Kappenman et al, The effects Of Electrode Impedance On Data Quality and statistical Significance in ERP Recordings NIH Public Access, Mar. 1, 2011.
Intl. Written Opinion for PCT/US2017/018012, May 11, 2017.
European Patent Office Search Report for EP Application 12851745.5, Aug. 28, 2015.
Scherg et al, Advanced Tools FOr Digital EEG Review, Journal of Clincial Neurophysiology, vol. 19, No. 2, 2002.
Klass, The Continuing Challenge of Artifacts in the EEG, AM. J. EEG Technol. 35:239-269, 1995.

201 — Generate a plurality of digital input signals from a machine comprising a source, a processor and a display.

202 — Submit the plurality of digital input signals to a recognition algorithm to generate a raw score.

203 — Calibrate the raw score to generate a probability value that an event will occur.

204 — Generate a graph of the probability value versus time.

200

350

370

700

701 — Generate original EEG signal from a machine comprising electrodes, an amplifier and a processor.

702 — Partition the original EEG signal from set of channels into epochs, of which has a duration length and an overlap increment.

703 — Perform artifact reduction on the epochs to generate artifact reduced epochs.

704 — Combine the artifact reduced epochs, of which overlaps an adjacent epoch for a continuous EEG recording, to generate a processed EEG recording.

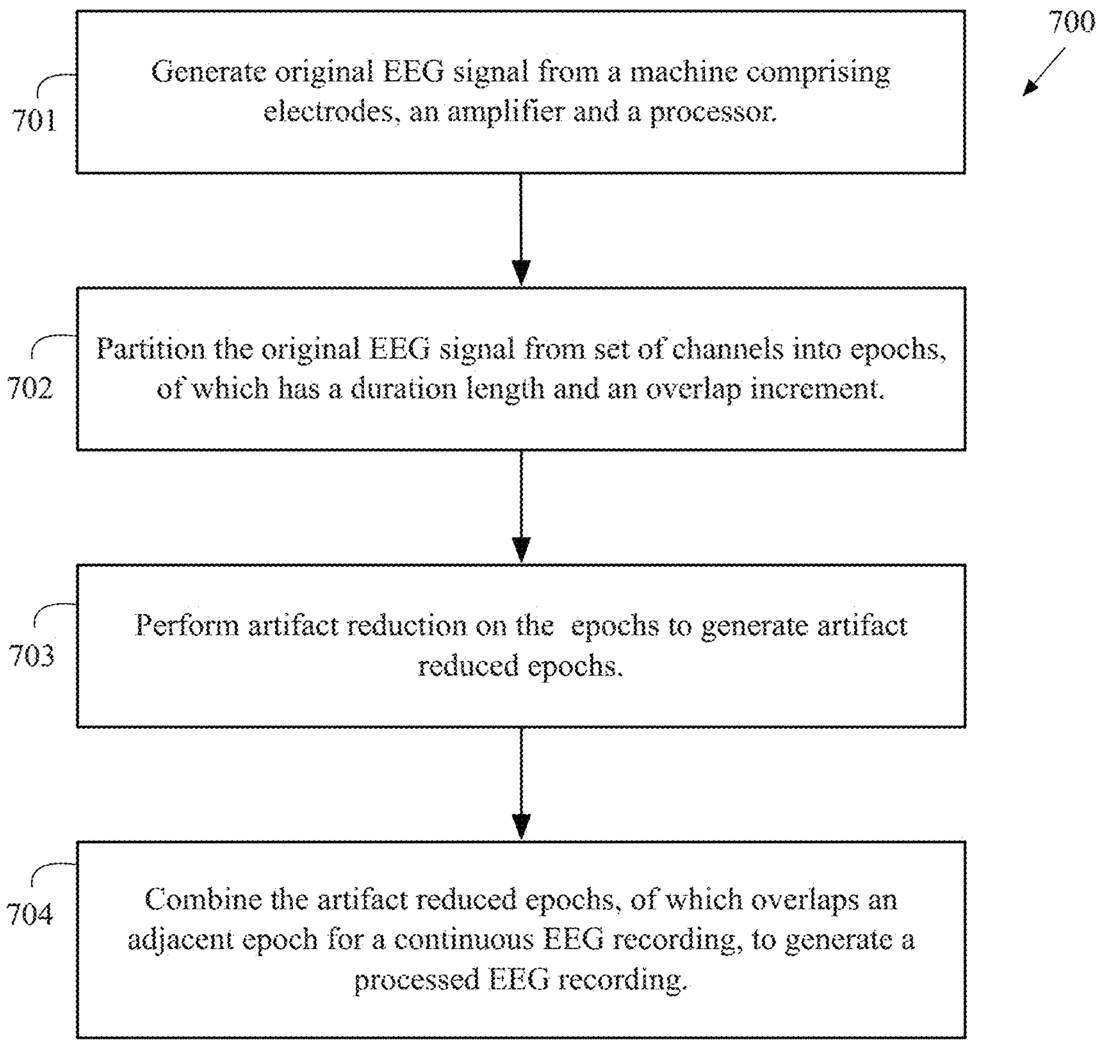

FIG. 18

901 — Generate an original EEG report, comprising a first set of channels, from an EEG signal; report generated from EEG machine with electrodes and a processor.

902 — Perform artifact reduction on the original EEG signal to generate a processed EEG report with a second set of channels.

903 — Overlay the processed EEG report on the original EEG report to generate a combined EEG report, with the x-axis and y-axis appropriately aligned and with equal channel sets.

904 — Display the combined EEG report, the processed EEG distinct from the original EEG; an artifact reduction at time $x$ on one channel of original EEG is identifiable on corresponding channel of second set of channels of the processed EEG report at time $x$.

900

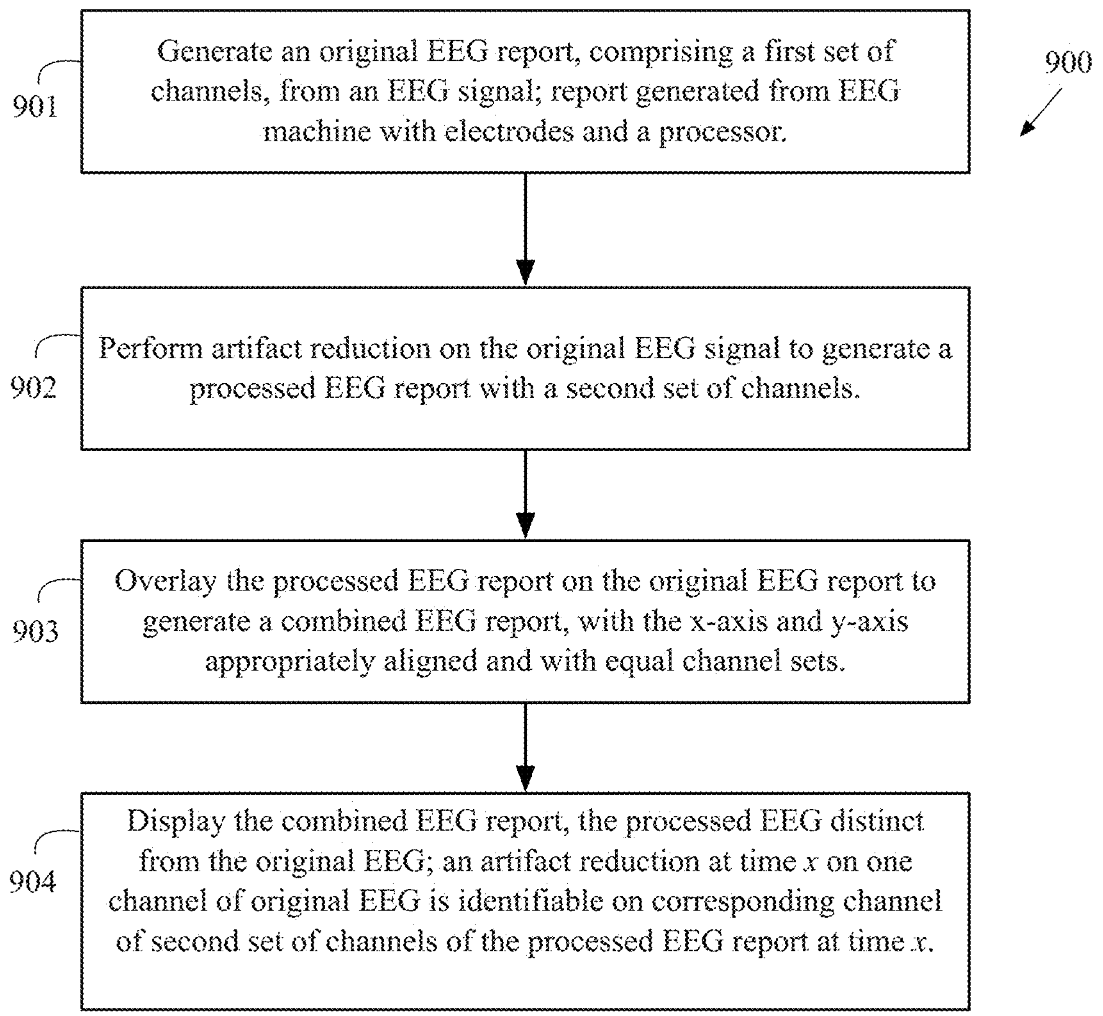

| File Edit View Insert Scroll Montage Reconstruction Tools Help |
|---|

| 5 sec | 7 uV | 1x | Bipolar longitudinal A | 0.16 se | 70Hz | (off) |

FP1-F3
F3-C3
C3-P3
P3-O1
FP2-F4
F4-C4
C4-P4
P4-O2
FP1-F7
F7-T3
T3-T5
T5-O1
FP2-F8
F8-T4
T4-T6
T6-O2
Fz-Cz
CZ-PZ

| Time | 15346.0 | 15347.0 | 15348.0 | 15349.0 | 15350.0 |

1600

| File Edit View Insert Scroll Montage Reconstruction Tools Help | | |
|---|---|---|
| 5 sec | 7 uV | 1x | Bipolar longitudinal A | (off) | 70Hz | (off) |

FP1-F3

F3-C3

C3-P3

P3-O1

FP2-F4

F4-C4

C4-P4

P4-O2

FP1-F7

F7-T3

T3-T5

T5-O1

FP2-F8

F8-T4

T4-T6

T6-O2

Fz-Cz

CZ-PZ

| Time | 15346.0 | 15347.0 | 15348.0 | 15349.0 | 15350.0 |

1700

| File Edit View Insert Scroll Montage Reconstruction Tools Help |

| (5 sec) (7 uV) (1x) (Bipolar longitudinal A) ((off)) (70Hz) ((off)) |

FP1-F3

F3-C3

C3-P3

P3-O1

FP2-F4

F4-C4

C4-P4

P4-O2

FP1-F7

F7-T3

T3-T5

T5-O1

FP2-F8

F8-T4

T4-T6

T6-O2

Fz-Cz

CZ-PZ

| Time | 15346.0 | 15347.0 | 15348.0 | 15349.0 | 15350.0 |

SYSTEM AND METHOD FOR GENERATING A PROBABILITY VALUE FOR AN EPILEPTIFORM ABNORMALITY BY NEURAL NETWORK TO IDENTIFY SIGNAL SPIKES

CROSS REFERENCES TO RELATED APPLICATIONS

The Present application is a continuation of U.S. patent application Ser. No. 17/175,635, filed on Feb. 13, 2021, which is a continuation of U.S. patent application Ser. No. 16/101,485, filed on Aug. 12, 2018, now U.S. patent Ser. No. 10/929,753, issued on Feb. 23, 2021, which is a continuation of U.S. patent application Ser. No. 14/222,655, filed on Mar. 23, 2014, now abandoned, which claims priority to U.S. Provisional Patent Application No. 61/929,120, filed on Jan. 20, 2014, each of which is hereby incorporated by reference in its entirety.

STATEMENT REGARDING FEDERALLY SPONSORED RESEARCH OR DEVELOPMENT

Not Applicable

BACKGROUND OF THE INVENTION

Field of the Invention

The present invention generally relates to a method and system for generating a probability value. More specifically, the present invention relates to a method and system for training a neural network for generating a probability value.

Description of the Related Art

Artificial neural networks are computational models capable of machine learning and pattern recognition. The artificial neural network generally is interconnected neurons that compute values from inputs by feeding data through the artificial neural network. Artificial neural networks have application in numerous areas including voice recognition, medical diagnosis, finance, trading, facial recognition, chemistry, game playing, decision making, robotics, and the like.

General definitions for terms utilized in the pertinent art are set forth below.

Boolean algebra is the subarea of algebra in which the values of the variables are the truth values true and false, usually denoted 1 and 0 respectively.

A Boolean network (BN) is a mathematical model of biological systems based on Boolean logic. The BN has a network structure consisting of nodes that correspond to genes or proteins. Each node in a BN takes a value of 1 or 0, meaning that the gene is or is not expressed.

Fuzzy logic is a form of many-valued logic; it deals with reasoning that is approximate rather than fixed and exact. Compared to traditional binary sets (where variables may take on true or false values) fuzzy logic variables may have a truth value that ranges in degree between 0 and 1. Fuzzy logic has been extended to handle the concept of partial truth, where the truth value may range between completely true and completely false. Furthermore, when linguistic variables are used, these degrees may be managed by specific functions. Irrationality can be described in terms of what is known as the "fuzzjective".

Multilayer perceptron ("MLP") is a feedforward artificial neural network model that maps sets of input data onto a set of appropriate outputs. An MLP consists of multiple layers of nodes in a directed graph, with each layer fully connected to the next one. Except for the input nodes, each node is a neuron (or processing element) with a nonlinear activation function.

Neural network ("NN") is an interconnected group of natural or artificial neurons that uses a mathematical or computational model for information processing based on a connectionistic approach to computation. In more practical terms neural networks are non-linear statistical data modeling or decision making tools. They can be used to model complex relationships between inputs and outputs or to find patterns in data.

Perceptron is a simple model of an artificial neuron which can predict boolean events after having been trained on past events. The perceptron is specified by the number of inputs N, and the weights connecting the inputs to the output node. The weights are the parameters which must be either set by hand or learned by a learning algorithm.

ROC curve (receiver operating characteristic) is a graphical plot of test sensitivity as the y coordinate versus its 1 minus specificity or false positive rate (FPR), as the x coordinate. The ROC curve is an effective method of evaluating the performance of diagnostic tests.

"Amplitude" refers to the vertical distance measured from the trough to the maximal peak (negative or positive). It expresses information about the size of the neuron population and its activation synchrony during the component generation.

The term "analogue to digital conversion" refers to when an analogue signal is converted into a digital signal which can then be stored in a computer for further processing. Analogue signals are "real world" signals (e.g., physiological signals such as electroencephalogram, electrocardiogram or electrooculogram). In order for them to be stored and manipulated by a computer, these signals must be converted into a discrete digital form the computer can understand.

An electroencephalogram ("EEG") is a diagnostic tool that measures and records the electrical activity of a person's brain in order to evaluate cerebral functions. Multiple electrodes are attached to a person's head and connected to a machine by wires. The machine amplifies the signals and records the electrical activity of a person's brain. The electrical activity is produced by the summation of neural activity across a plurality of neurons. These neurons generate small electric voltage fields. The aggregate of these electric voltage fields create an electrical reading which electrodes on the person's head are able to detect and record. An EEG is a superposition of multiple simpler signals. In a normal adult, the amplitude of an EEG signal typically ranges from 1 micro-Volt to 100 micro-Volts, and the EEG signal is approximately 10 to 20 milli-Volts when measured with subdural electrodes. The monitoring of the amplitude and temporal dynamics of the electrical signals provides information about the underlying neural activity and medical conditions of the person.

An EEG is performed to: diagnose epilepsy; verify problems with loss of consciousness or dementia; verify brain activity for a person in a coma; study sleep disorders, monitor brain activity during surgery, and additional physical problems.

Multiple electrodes (typically 17-21, however there are standard positions for at least 70) are attached to a person's head during an EEG. The electrodes are referenced by the position of the electrode in relation to a lobe or area of a person's brain. The references are as follows: F=frontal; Fp=frontopolar; T=temporal; C=central; P=parietal; O=occipital; and A=auricular (ear electrode). Numerals are used to further narrow the position and "z" points relate to electrode sites in the midline of a person's head. An electrocardiogram ("EKG") may also appear on an EEG display.

The EEG records brain waves from different amplifiers using various combinations of electrodes called montages. Montages are generally created to provide a clear picture of the spatial distribution of the EEG across the cortex. A montage is an electrical map obtained from a spatial array of recording electrodes and preferably refers to a particular combination of electrodes examined at a particular point in time.

In bipolar montages, consecutive pairs of electrodes are linked by connecting the electrode input 2 of one channel to input 1 of the subsequent channel, so that adjacent channels have one electrode in common. The bipolar chains of electrodes may be connected going from front to back (longitudinal) or from left to right (transverse). In a bipolar montage signals between two active electrode sites are compared resulting in the difference in activity recorded. Another type of montage is the referential montage or monopolar montage. In a referential montage, various electrodes are connected to input 1 of each amplifier and a reference electrode is connected to input 2 of each amplifier. In a reference montage, signals are collected at an active electrode site and compared to a common reference electrode.

Reference montages are good for determining the true amplitude and morphology of a waveform. For temporal electrodes, CZ is usually a good scalp reference.

Being able to locate the origin of electrical activity ("localization") is critical to being able to analyze the EEG. Localization of normal or abnormal brain waves in bipolar montages is usually accomplished by identifying "phase reversal," a deflection of the two channels within a chain pointing to opposite directions. In a referential montage, all channels may show deflections in the same direction. If the electrical activity at the active electrodes is positive when compared to the activity at the reference electrode, the deflection will be downward. Electrodes where the electrical activity is the same as at the reference electrode will not show any deflection. In general, the electrode with the largest upward deflection represents the maximum negative activity in a referential montage.

Some patterns indicate a tendency toward seizures in a person. A physician may refer to these waves as "epileptiform abnormalities" or "epilepsy waves." These include spikes, sharp waves, and spike-and-wave discharges. Spikes and sharp waves in a specific area of the brain, such as the left temporal lobe, indicate that partial seizures might possibly come from that area. Primary generalized epilepsy, on the other hand, is suggested by spike-and-wave discharges that are widely spread over both hemispheres of the brain, especially if they begin in both hemispheres at the same time.

There are several types of brain waves: alpha waves, beta waves, delta wave, theta waves and gamma waves. Alpha waves have a frequency of 8 to 12 Hertz ("Hz"). Alpha waves are normally found when a person is relaxed or in a waking state when a person's eyes are closed but the person is mentally alert. Alpha waves cease when a person's eyes are open or the person is concentrating. Beta waves have a frequency of 13 Hz to 30 Hz. Beta waves are normally found when a person is alert, thinking, agitated, or has taken high doses of certain medicines. Delta waves have a frequency of less than 3 Hz. Delta waves are normally found only when a person is asleep (non-REM or dreamless sleep) or the person is a young child. Theta waves have a frequency of 4 Hz to 7 Hz. Theta waves are normally found only when the person is asleep (dream or REM sleep) or the person is a young child. Gamma waves have a frequency of 30 Hz to 100 Hz. Gamma waves are normally found during higher mental activity and motor functions.

The following definitions are used herein.

"Amplitude" refers to the vertical distance measured from the trough to the maximal peak (negative or positive). It expresses information about the size of the neuron population and its activation synchrony during the component generation.

The term "analogue to digital conversion" refers to when an analogue signal is converted into a digital signal which can then be stored in a computer for further processing. Analogue signals are "real world" signals (e.g., physiological signals such as electroencephalogram, electrocardiogram or electrooculogram). In order for them to be stored and manipulated by a computer, these signals must be converted into a discrete digital form the computer can understand.

"Artifacts" are electrical signals detected along the scalp by an EEG, but that originate from non-cerebral origin. There are patient related artifacts (e.g., movement, sweating, ECG, eye movements) and technical artifacts (50/60 Hz artifact, cable movements, electrode paste-related).

The term "differential amplifier" refers to the key to electrophysiological equipment. It magnifies the difference between two inputs (one amplifier per pair of electrodes).

"Duration" is the time interval from the beginning of the voltage change to its return to the baseline. It is also a measurement of the synchronous activation of neurons involved in the component generation.

"Electrode" refers to a conductor used to establish electrical contact with a nonmetallic part of a circuit. EEG electrodes are small metal discs usually made of stainless steel, tin, gold or silver covered with a silver chloride coating. They are placed on the scalp in special positions.

"Electrode gel" acts as a malleable extension of the electrode, so that the movement of the electrodes leads is less likely to produce artifacts. The gel maximizes skin contact and allows for a low-resistance recording through the skin.

The term "electrode positioning" (10/20 system) refers to the standardized placement of scalp electrodes for a classical EEG recording. The essence of this system is the distance in percentages of the 10/20 range between Nasion-Inion and fixed points. These points are marked as the Frontal pole (Fp), Central (C), Parietal (P), occipital (O), and Temporal (T). The midline electrodes are marked with a subscript z, which stands for zero. The odd numbers are used as subscript for points over the left hemisphere, and even numbers over the right "Electroencephalogram" or "EEG" refers to the tracing of brain waves, by recording the electrical activity of the brain from the scalp, made by an electroencephalograph.

"Electroencephalograph" refers to an apparatus for detecting and recording brain waves (also called encephalograph).

"Epileptiform" refers to resembling that of epilepsy.

"Filtering" refers to a process that removes unwanted frequencies from a signal.

"Filters" are devices that alter the frequency composition of the signal.

"Montage" means the placement of the electrodes. The EEG can be monitored with either a bipolar montage or a referential one. Bipolar means that there are two electrodes per one channel, so there is a reference electrode for each channel. The referential montage means that there is a common reference electrode for all the channels.

"Morphology" refers to the shape of the waveform. The shape of a wave or an EEG pattern is determined by the frequencies that combine to make up the waveform and by their phase and voltage relationships. Wave patterns can be described as being: "Monomorphic". Distinct EEG activity appearing to be composed of one dominant activity. "Polymorphic". distinct EEG activity composed of multiple frequencies that combine to form a complex waveform. "Sinusoidal". Waves resembling sine waves. Monomorphic activity usually is sinusoidal. "Transient". An isolated wave or pattern that is distinctly different from background activity.

"Spike" refers to a transient with a pointed peak and a duration from 20 to under 70 msec.

The term "sharp wave" refers to a transient with a pointed peak and duration of 70-200 msec.

The term "neural network algorithms" refers to algorithms that identify sharp transients that have a high probability of being epileptiform abnormalities.

"Noise" refers to any unwanted signal that modifies the desired signal. It can have multiple sources.

"Periodicity" refers to the distribution of patterns or elements in time (e.g., the appearance of a particular EEG activity at more or less regular intervals). The activity may be generalized, focal or lateralized.

"Sampling" or the term "sampling the signal" refers to reducing a continuous signal to a discrete signal. A digital signal is a sampled signal; obtained by sampling the analogue signal at discrete points in time.

The term "sampling interval" is the time between successive samples; these points are usually evenly spaced in time.

The term "sampling rate" refers to the frequency expressed in Hertz (Hz) at which the analogue-to-digital converter (ADC) samples the input analogue signal.

The term "Signal to Noise Ratio" (SNR) refers to a measurement of the amplitude of variance of the signal relative to the variance of the noise.

An EEG epoch is an amplitude of an EEG signal as a function of time and frequency.

Various techniques have been developed to present the EEG data to a physician or technician. However, these techniques are still lacking. Learning what is an artifact and how to see what is in the underlying signal is one of the most difficult problems in EEG interpretation. A number of techniques have been developed for algorithmically removing artifact to produce a cleaner EEG, but in order for these to be adopted commercially it is necessary to develop a user interface that allows the user to see how the original signal has evolved to the clean signal.

Thus, there is a need for improving training of neural networks.

BRIEF SUMMARY OF THE INVENTION

The present invention provides a solution to the shortcomings of the prior art. The present invention provides a method and system for training a neural network.

One aspect of the present invention is a system for generating a probability value for an event. The system includes a source for generating a plurality of digital input signals, a processor connected to the source to receive the plurality of digital input signals from the source, and a display connected to the processor for displaying a final output.

Preferably, the processor is configured to submit the plurality of digital input signals to a recognition algorithm to generate a raw score, to calibrate the raw score to generate a probability value that an event has occurred, and to generate a display of the probability value versus time. The processor is further configured to validate the probability value.

Preferably, the system further includes that the plurality of digital input signals comprises at least one of a value for a fraudulent credit card transaction, a value for a monthly salary income for the loan applicant, a value for monthly rental income for the loan applicant, a value of a collateral for the loan, a value for a monthly car payment for the loan applicant, a value of a number of years employed for the loan applicant.

Another aspect of the present invention is a method for generating a probability value for an event. The method includes generating a plurality of digital input signals from a machine comprising a source, a processor and a display, submitting the plurality of digital input signals to a recognition algorithm to generate a raw score, calibrating the raw score to generate a probability value that an event will occur, and generating a graph of the probability value versus time.

Preferably, the method further includes validating the probability value.

Yet another aspect of the present invention is a system for validating a seizure probability for an EEG. The system includes a plurality of electrodes for generating a plurality of EEG signals, a processor connected to the plurality of electrodes to generate an EEG recording from the plurality of EEG signals, and a display connected to the processor for displaying a seizure detection probability.

Preferably, the processor is configured to submit the EEG recording to a neural network to generate a raw score, to calibrate the raw score to generate a probability value for a seizure, and to generate a graph of the probability value versus time. The processor is also preferably configured to validate the probability value.

Yet another aspect of the present invention is a method for validating a seizure probability for an EEG. The method includes generating a plurality a plurality of EEG signals, generating an EEG recording from the plurality of EEG signals, submitting the EEG recording to a neural network to generate a raw score, calibrating the raw score to generate a probability value that a seizure has occurred, and generating a graph of the probability value versus time.

Preferably, the method further includes validating the probability value.

Yet another aspect of the present invention is a method for generating a probability value for an event. The method includes generating a plurality of training set inputs from a machine comprising a source, a processor and a user-interface, submitting the plurality of training set inputs to a recognition algorithm to generate a raw score, calibrating the raw score to generate a probability value that an event will occur, validating a set to test, and generating probability values against data submitted for analysis.

The present invention also provides a solution to the problem of presenting the EEG data to a physician or technician for EEG interpretation by providing a user interface for artifact removal in an EEG. This is important for two main reasons. First, it provides confidence to the user that the cleaner EEG correctly represents what would be present in the absence of artifacts. Secondly, the user may want to see the original signal, or the signal after only partial cleaning in order to determine if there is information present that is useful.

In the present invention a process of producing a "clean" EEG involves a series of steps. For example, artifacts related to electrical issues might be one step. Another step would remove eye blinks. Another step might remove surface muscle. Yet another step might remove effects of tongue movement. Each step is a kind of algorithmic filter, although this is very different than the classic filters that remove everything within a certain frequency range. Currently, EEG is typically displayed as a series of traces organized by channel. Channels commonly represent the voltage difference between two scalp electrodes, but they can also represent the differences between an electrode and an average or other aggregation of a group of electrodes. The traces have a vertical axis of voltage and a horizontal axis of time. Sets of channels are displayed on a page, and a set of channels is called a montage.

The information displayed in a montage can commonly be filtered by removing certain frequency ranges. There are also frequently other options such as limiting "pen deflection" which limits the amplitude of a trace and drawing a horizontal line until the amplitude is below the limit.

With the introduction of artifact filters the user will need the ability to select which artifact filters are being applied and have that confirmed on the display. In addition, they will need the ability to simultaneously show a set of traces for each channel representing the effects of the artifact filters. One choice would be to show both the original signal as well as the signal after applying the entire set of selected filters. They may also want to see a trace with the difference between the original signal and the filtered signal. They may also want to see traces showing the signal at different points in the process of artifact filtering. For example, they might want to see a trace with just the muscle artifacts removed but leaving the eye blinks. In order to remove some artifacts like eye blinks the software might use specific recognition algorithms that detect the pattern. In this case the user may simply want to see an indication that an eye blink or other pattern was present while still removing the effects of the pattern from the trace. (People reading EEGs use eye blinks as one way to tell that the patient is awake, but the eye blink produces a large artifact obscuring other information on the channels it affects).

Another feature of the present invention is the ability to select colors for the various traces and the amount of darkness/emphasis. Some users may want the original signal to be primary with the artifact filtered traces present in the background as reference. Other users may want one of the filtered traces to be primary. Choice of colors is important for this reason and also because a significant fraction of people are color blind to certain colors.

Another aspect of the artifact filtering process is that it will break the signal into a set of underlying signals. This can be useful even after artifacts are removed in seeing the various components of the true signal from the brain. For example, there might be slow waves separate from individual epileptiform patterns. A user might want to choose to see these components separately on a channel to make it easier to see the various portions of the true signal. Doing this would likely not have been useful prior to removing most significant artifacts.

Another aspect of the present invention is a single "button" that applies a set of pre-selected artifact filters in a standard program used to review EEG. The button allows a technician to toggle on and off to allow for filtered and unfiltered traces for review by the technician.

One aspect of the present invention is a method for analyzing an EEG recording. The method includes generating an EEG recording from a machine comprising a plurality of electrodes, an amplifier and processor. The method also includes processing the EEG to create a processed EEG recording for analysis. The method also includes recognizing a pattern in the processed EEG recording.

Another aspect of the present invention is a system for analyzing an EEG recording. The system includes electrodes for generating a plurality of EEG signals, at least one amplifier connected to each of the plurality of electrodes by a plurality of wires to amplify each of the plurality of EEG signals, a processor connected to the amplifier to generate an EEG recording from the plurality of EEG signals, a display connected to the processor for displaying an EEG recording. The processor is configured to recognize a pattern in the processed EEG recording.

Yet another aspect of the present invention is a method for analyzing an EEG recording. The method includes generating an EEG recording from a machine comprising a plurality of electrodes, an amplifier and processor. The method also includes processing the EEG to create a processed EEG recording for analysis. The method also includes detecting a plurality of events in the processed EEG recording. The method also includes presenting the plurality of events as an event density graph.

Another aspect of the present provides an EEG system and method that overlays a processed EEG report over a raw EEG report to permit a physician or technician to clearly see the activity reported.

This embodiment provides the ability to select short overlapping epochs where the results of artifact removal from each epoch is stitched together with the result from the next and previous epoch. This stitching can be accomplished many ways, but in a preferred method the signals from the two epochs are combined using a weighted average where the weight is proportional to the ratio of the distance to the epoch centers.

For example, an epoch length of two seconds is selected with an increment (epoch step) of one second. Artifact removal using BSS and other techniques is performed on a set of channels for seconds one and two producing a two second length "clean" result. Then artifact removal is performed on seconds two and three producing an overlapping clean result. The results overlap in the second second of the record. For each channel, the weighted average of the two overlapping results produces a final result without discontinuities. In the portion of the second nearer the center of the first epoch the value from the first epoch is weighted higher, and likewise for the portion nearer the center of the second epoch. Those skilled in the pertinent art will recognize that different or variable epoch lengths or steps may be selected while moving through the record. Also, a different stitching technique might be used.

One aspect of the present invention is a method for filtering artifacts from an EEG signal. The method includes generating an EEG signal from a machine comprising a plurality of electrodes, an amplifier and processor. The method also includes transforming the EEG signal from a set of channels into a plurality of epochs. Each of the plurality of epochs has an epoch duration length of less than or equal to two seconds and an increment of less than or equal to one second. The method also includes filtering artifacts from each of the plurality of epochs using a blind source separation algorithm to generate a plurality of clean epochs. The method also includes combining the plurality of clean epochs to generate a processed EEG recording.

Yet another aspect of the present invention is a method for filtering artifacts from an EEG signal using a blind source separation algorithm. The method includes generating an EEG signal from a machine comprising a plurality of electrodes, an amplifier and processor. The method also includes transforming the EEG signal from a set of channels into a plurality of epochs. The method also includes filtering artifacts from each of the plurality of epochs using a blind source separation algorithm to generate a plurality of clean epochs. The method also includes combining the plurality of clean epochs to generate a processed EEG recording.

Yet another aspect of the present invention is a system for filtering artifacts from an EEG signal. The system includes electrodes, an amplifier, a processor and a display. The electrodes generate EEG signals. The amplifier is connected to each of the electrodes by wires and amplifies the EEG signals. The processor is connected to the amplifier to generate an EEG recording from the EEG signals. The display is connected to the processor to display an EEG recording. The processor is configured to transform each of the plurality of EEG signals from a set of channels into a plurality of epochs, remove artifacts from each of the plurality of epochs using a blind source separation algorithm to generate a plurality of clean epochs, and combine the plurality of clean epochs to generate a processed EEG recording for display.

Yet another aspect of the present invention is a method for filtering artifacts from an EEG signal using an artifact removal algorithm. The method includes generating an EEG signal from a machine comprising a plurality of electrodes, an amplifier and processor. The method also includes transforming the EEG signal from a set of channels into a plurality of epochs. The method also includes filtering artifacts from each of the plurality of epochs using an artifact removal algorithm to generate a plurality of clean epochs. The method also includes combining the plurality of clean epochs to generate a processed EEG recording.

Yet another aspect of the present invention is a method for filtering artifacts from an EEG signal by selecting an epoch time and increment. The method includes generating an EEG signal for a patient from a machine comprising a plurality of electrodes attached to the patient, an amplifier and processor. The method also includes selecting an epoch time length and an epoch time increment. The method also includes filtering artifacts for each of a plurality of epochs using an artifact removal algorithm to generate a plurality of clean epochs. The method also includes assigning a weighted average to each of the plurality of clean epochs. The method also includes combining the plurality of clean epochs to overlap to generate a processed EEG recording without discontinuities.

Yet another aspect of the present invention is a system for filtering artifacts from an EEG signal. The system includes electrodes, a processor, and a display. The electrodes generate EEG signals. The processor is connected to the electrodes to generate an EEG recording from the EEG signals. The display is connected to the processor and displays an EEG recording. The processor is configured to select an epoch time length and an epoch time increment, filter artifacts for each of a plurality of epochs using an artifact removal algorithm to generate a plurality of clean epochs, assign a weighted average to each of the plurality of clean epochs, and combine the plurality of clean epochs to overlap to generate a processed EEG recording without discontinuities.

Still another aspect of the present invention is a method for displaying EEG data. The method includes generating an original EEG report from an EEG signal. The original EEG report is generated from an EEG machine comprising a plurality of electrodes and processor. The original EEG report comprises a first plurality of channels. The method also includes performing artifact reduction on the original EEG signal to generate a processed EEG report. The processed EEG report comprises a second plurality of channels. The method also includes overlaying the processed EEG report on the original EEG report to generate a combined EEG report. An x-axis of the processed EEG report is aligned with an x-axis of the original EEG report. A y-axis of the processed EEG report is aligned with an y-axis of the original EEG report. The first plurality of channels of the original EEG report are equal to the second plurality of channels of the processed EEG report. The method also includes displaying the combined EEG report wherein the processed EEG report is visually distinctive from the original EEG report. An activity at a specific time on one channel of the first plurality of channels of the original EEG report is identifiable on a corresponding channel of the second plurality of channels of the processed EEG report at the specific time. The activity is preferably spikes, sharp waves, spike and wave discharges, artifacts, and the like.

Still another aspect of the present invention is a method for displaying a combined EEG report. The method includes generating an original EEG report from an EEG signal. The original EEG report is generated from an EEG machine comprising a plurality of electrodes and processor. The original EEG report comprises a first plurality of channels. The method also includes performing artifact reduction on the original EEG signal to generate a processed continuous EEG report. The processed EEG report comprises a second plurality of channels. The method also includes overlaying the processed continuous EEG report on the original EEG report to generate a combined EEG report. An x-axis of the processed continuous EEG report is aligned with an x-axis of the original EEG report. A y-axis of the processed continuous EEG report is aligned with an y-axis of the original EEG report. The first plurality of channels of the original EEG report are equal to the second plurality of channels of the processed continuous EEG report. The method also includes displaying the combined EEG report wherein the processed EEG report is visually distinctive from the original EEG report. An activity at a specific time on one channel of the first plurality of channels of the original EEG report is identifiable on a corresponding channel of the second plurality of channels of the processed continuous EEG report at the specific time.

Still another aspect of the present invention is a system for displaying EEG data. The system includes a patient component, a machine component and a display screen. The patient component comprises a plurality of electrodes for generating an EEG signal. The EEG machine component comprises an amplifier and a processor. The processor is configured to generate an original EEG report from an EEG signal. The original EEG report comprises a first plurality of channels. The processor is also configured to perform artifact reduction on the original EEG signal to generate a processed EEG report. The processed EEG report comprises a second plurality of channels. The processor is also configured to overlay the processed EEG report on the original EEG report to generate a combined EEG report. An x-axis of the processed EEG report is aligned with an x-axis of the original EEG report. A y-axis of the processed EEG report is aligned with an y-axis of the original EEG report. The first plurality of channels of the original EEG report are equal to the second plurality of channels of the processed EEG report. The display screen displays the combined EGG report wherein the processed EEG report is visually distinctive from the original EEG report, and wherein an activity at a specific time on one channel of the first plurality of channels of the original EEG report is identifiable on a corresponding channel of the second plurality of channels of the processed EEG report at the specific time.

Having briefly described the present invention, the above and further objects, features and advantages thereof will be recognized by those skilled in the pertinent art from the following detailed description of the invention when taken in conjunction with the accompanying drawings.

BRIEF DESCRIPTION OF THE SEVERAL VIEWS OF THE DRAWINGS

FIG. 18 is a flow chart of a method for displaying EEG data.

FIG. 26 is a flow chart of a method for displaying EEG data.

DETAILED DESCRIPTION OF THE INVENTION

Figure 1:
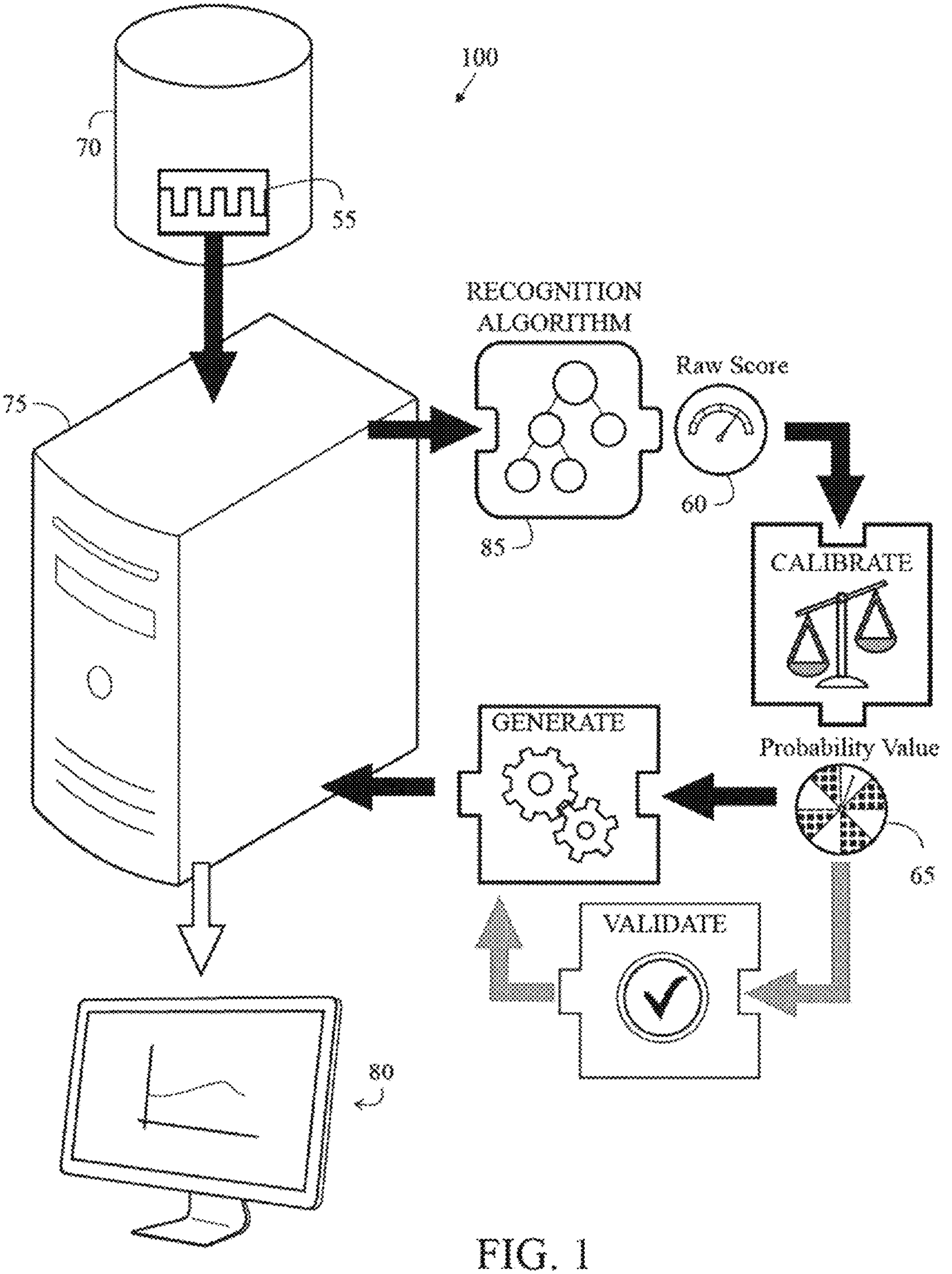
FIG. 1 is a block diagram of a system for generating a probability value for an event.
Figure 1A:
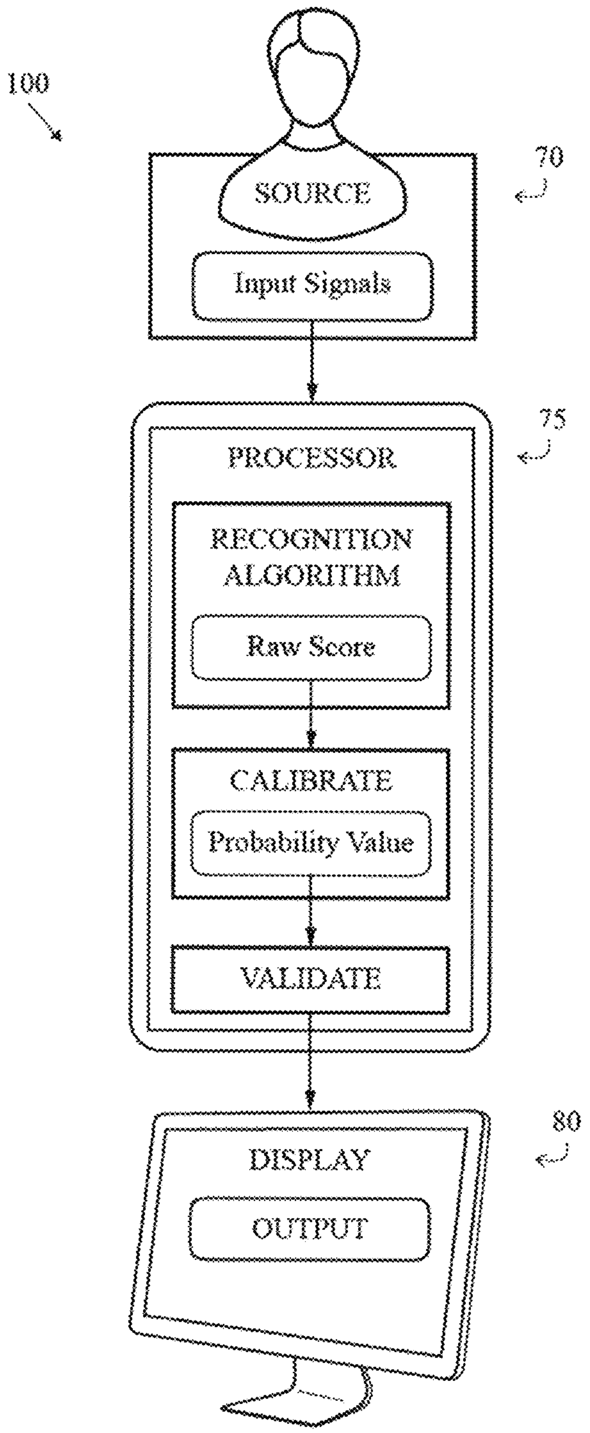
FIG. 1A is a block diagram of a system for generating a probability value for an event.

As shown in FIGS. 1 and 1A, a system for generating a probability value is generally designated 100. The system 100 preferably comprises a source 70, a processor 75, and a display 80. The source 70 generates digital input signals, which are received by a processor 75 that is connected to the source 70. The processor 75 is configured to submit the digital input signals to a recognition algorithm 85 to generate a raw score 60. The processor 75 is also configured to calibrate the raw score 60 to generate a probability value 65 that an event has occurred and then to generate a display of the probability value 65 versus time. Further, the processor 75 is configured to validate the probability value 65. The processor 75 is also connected to a display 80 for displaying a final output.

Figure 2:
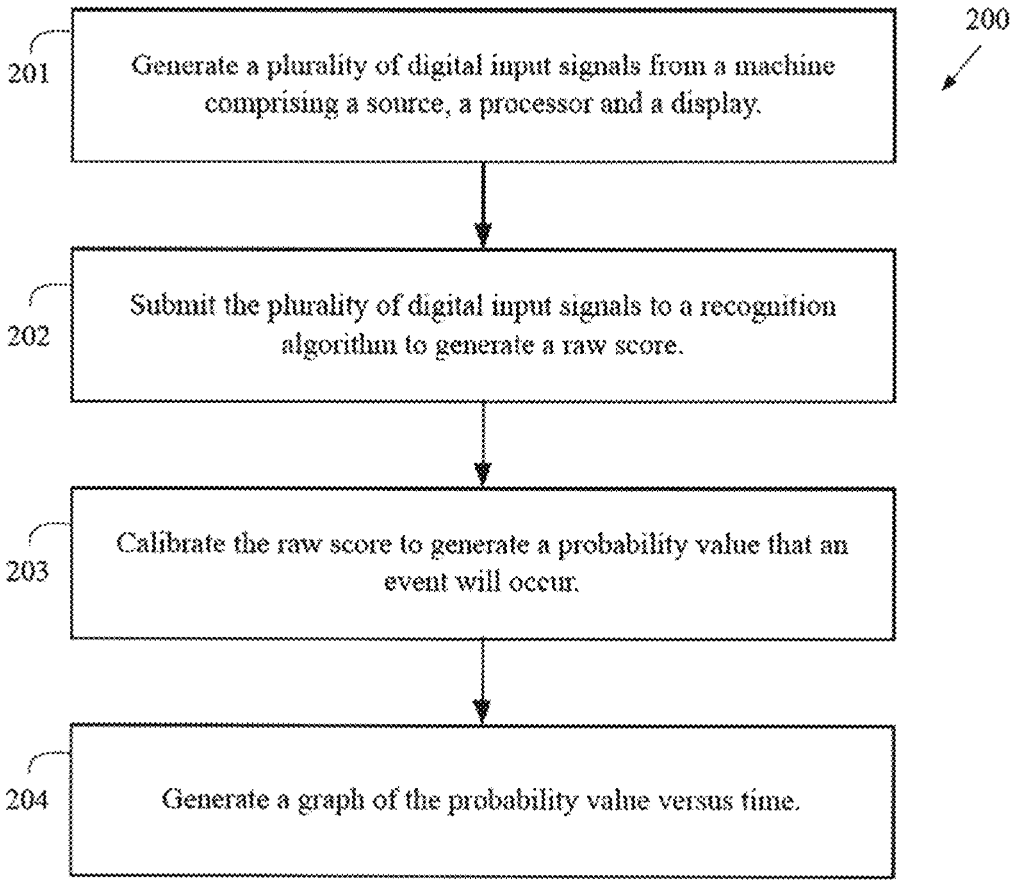
FIG. 2 is a flow chart of a method for generating a probability value for an event.

A general method 200 for generating a probability value is illustrated in the flow chart of FIG. 2. At block 201, a plurality of digital input signals is generated from a machine comprising a source, a processor and a display. At block 202, the plurality of digital input signals is submitted to a recognition algorithm to generate a raw score. At block 203, a raw score is calibrated to generate a probability value that an event will occur. At block 204, a graph of the probability value versus time is generated.

Figure 3:
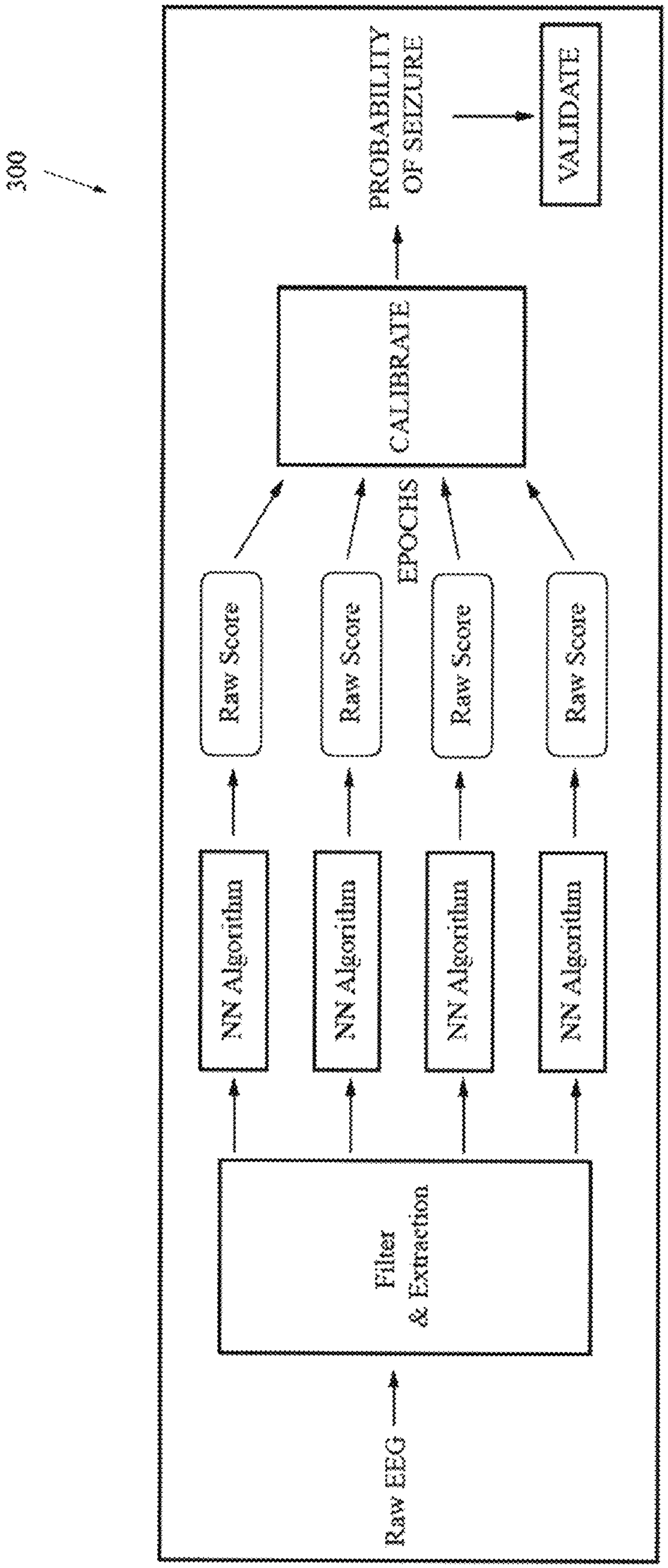
FIG. 3 is a block diagram for generating a probability value for a seizure.

FIG. 3 is a block diagram of a specific example of a system 300 for generating a probability value for detecting a seizure from a raw EEG recording. The raw EEG is processed through artifact reduction filters and neural network algorithms to generate raw score epochs that are calibrated to generate a probability value that a seizure is occurring. For example, taking one hundred epochs of one second duration that were given a 20% probability score of a seizure, the system determines if twenty of those one hundred were actually a seizure. This occurs by calibrating fifty of the epochs to measure if seizures occurred in ten of those fifty. The calibration will provide a probability value, which will be validated against the remaining fifty epochs. Next, one hundred epochs of one second duration that were given a 30% probability score of a seizure, the system determines if thirty of those one hundred were actually a seizure. This occurs by calibrating fifty of the epochs to measure if seizures occurred in fifteen of those fifty. The calibration will provide a probability value, which will be validated against the remaining fifty epochs. If fifteen of the remaining fifty evidence a seizure, then the probability value is validated. This also allows for training of a neural network to generate a validated probability value.

In another example, the digital input signals from the source 70 are a value for a fraudulent credit card transaction, a value for a monthly salary income for a loan applicant, a value for monthly rental income for a loan applicant, a value of a collateral for a loan, a value for a monthly car payment for a loan applicant, or a value of a number of years employed for a loan applicant.

Artificial neural networks (ANN) have been used to solve various tasks in numerous fields that are hard to solve using ordinary rule-based programming. An ANN can learn and adapt through learning algorithms. The types of ANNs and ANN architecture varies, mainly in the learning method.

The basic phases of an example algorithm 300 are shown in FIG. 3.

Figure 5:
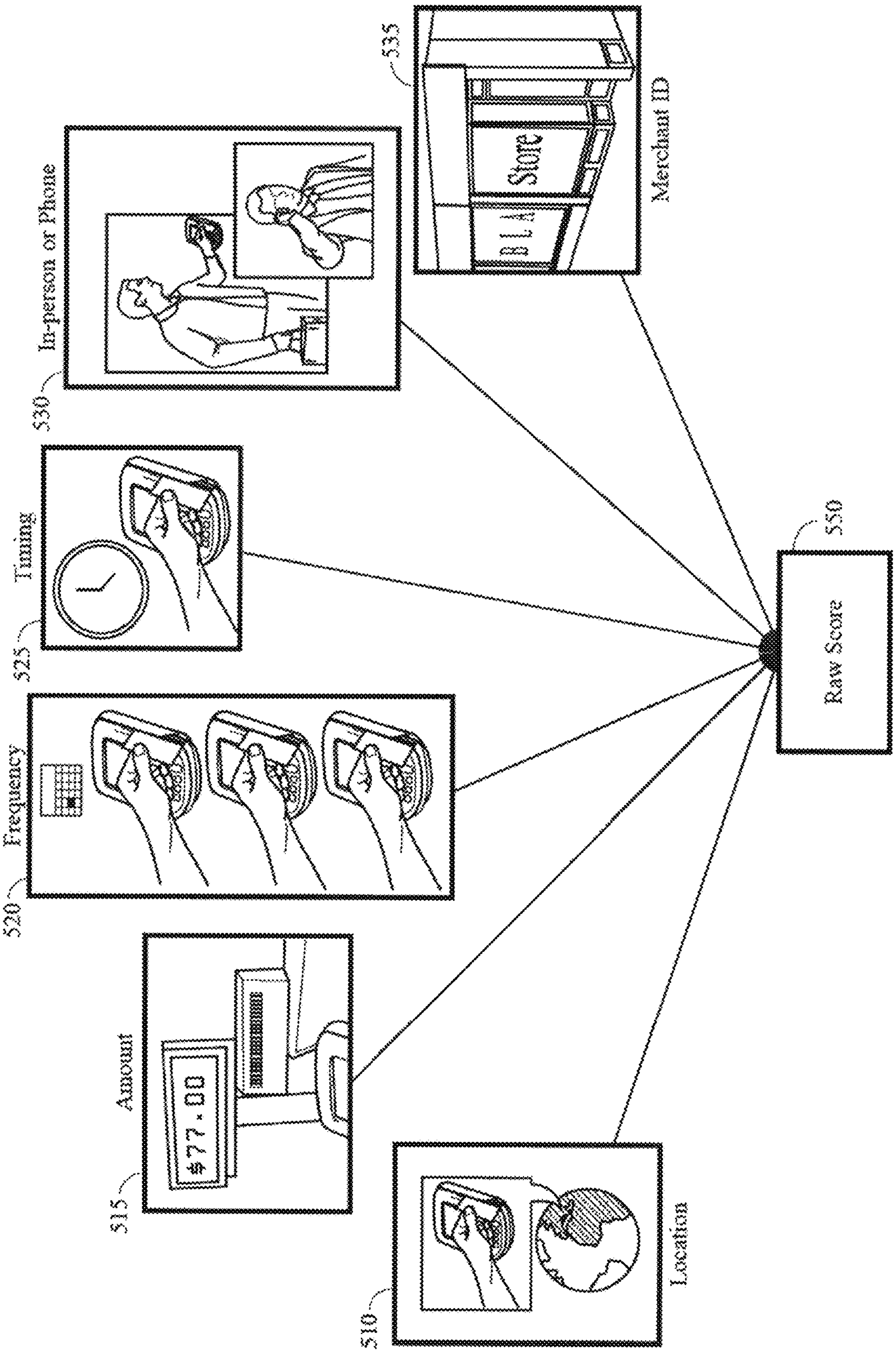
FIG. 5 is a block diagram of a flow chart of inputs for generating a raw score for a fraudulent credit card transaction.

A multilayer perceptron (MLP) is a feed forward ANN. FIG. 5 shows a graphical depiction of the MLP architecture with six inputs ($x_1$-$x_6$), three hidden nodes and a single output ($y_k$) Using a value for a fraudulent credit card transaction as the digital input signal as an example, an ANN can be used to recognize patterns of credit card use. The inputs can be information such as related to the cardholder or to the transactions. Example inputs can include types of purchases, frequency of specific purchases, time of purchase, or where purchases were made. The inputs are processed through the hidden node and then the output is a decision after processing. While the algorithm does not "match up" the pattern, the purpose is to determine the differences and find a threshold for the difference before determining that the use is fraudulent.

Figure 4:
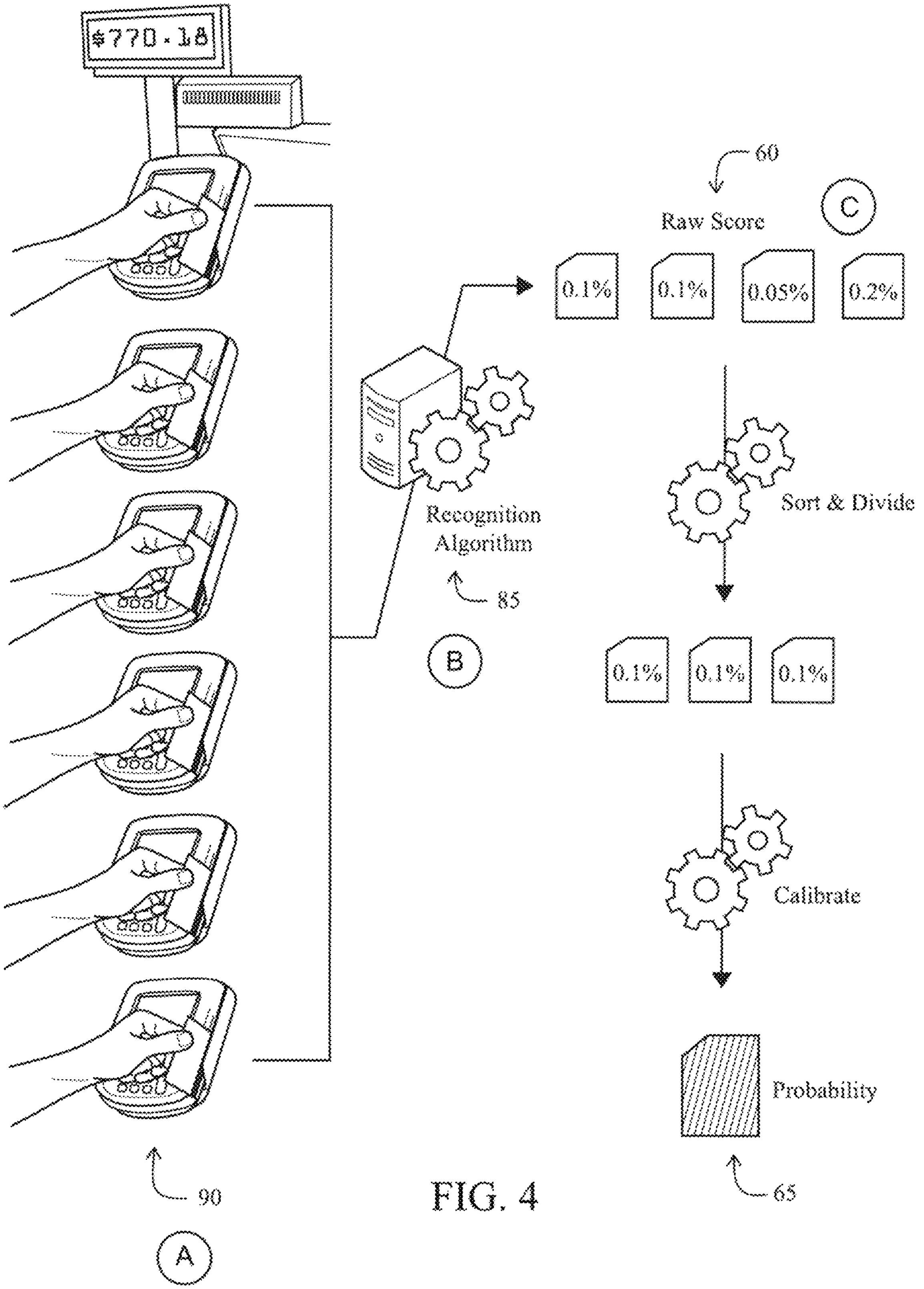
FIG. 4 is a block diagram of a flow chart of determining a probability value for a fraudulent credit card transaction.

FIGS. 4 and 5 are directed to an embodiment for determining a probability value for fraudulent credit card transactions. As shown in FIG. 4, at stage A, multiple credit card transactions 90 are performed credit card users. At stage B, each transaction 90 is transmitted to a server for a credit card company for authorization of each of the charges. The server utilizes an algorithm 85 to generate a raw score 60 value at stage C. FIG. 5 illustrates some of the inputs utilized in an algorithm to generate a raw score value. The inputs for the algorithm of the example include: location 510, amount 515, frequency of credit card use 520, the timing of the use 525, in-person or by phone 530, and the identification of the merchant 535. These inputs are used to generate a raw score 550. However, those skilled in the pertinent art will recognize that other algorithms will use more or less inputs to generate a raw score without departing from the scope and spirit of the present invention.

Returning to FIG. 4, the raw scores are sorted by similar values, such as 0.1% for one group and 0.05% for another group. Then, half of the raw score values are calibrated to generate a probability value 65. During the calibration stage, the groups sorted by raw scores are analyzed with the actual data for each credit card transaction in the group to calibrate the raw score value. For example, if all of the credit card transactions with a 0.1% raw score value area analyzed, then only 0.1% of the transactions should be fraudulent. However, if the actual data shows that the true value is 0.095% of the transactions were fraudulent, then the raw score value is calibrated and a probability value for those raw scores values is now 0.0095%.

Next, the other half of the raw score values are validated with the corrected algorithm using the probability value. If the actual data for this second half of raw scores values demonstrates that the probability value is correct, then the calibrated algorithm has been validated. However, if the validation is incorrect, the process is repeated.

In classification, the task is to a classify a variable $y=x_0$ called class variable or output given a set of variables $x=x_1 \ldots x_n$, called attribute variables or input. A classifier $h:x \rightarrow y$ is a function that maps an instance of x to a value of y. The classifier is learned from a dataset d consisting of samples over (x, y). The learning task consists of finding an appropriate Bayesian network given a data set d over U. Let $U=\{x_1, \ldots, x_n\}$, $n \geq 1$ be a set of variables.

In an example for a loan application, there are two classes, low-risk and high-risk applicants. In order to find out if an applicant may default on the loan, a probability is calculated, $P(Y|X)$, where X is the input, such as salary income, and Y is the 0 or 1 to indicate low-risk or high-risk, respectively. For a given X=x, $P(Y=1|X=x)=0.9$, the probability is 90 percent that the applicant is high-risk.

A perceptron models a biological neuron as a mathematical function, $$y = \sum_{j=1}^{d} w_j x_j + w_0$$

where the weighted sum, y, of the input values, $x_j \in \mathfrak{R}$, j=1, . . . , $d_j$, are calculated. The weights are $w_j \in \mathfrak{R}$.

The following is a Perceptron Training Algorithm for training a MLP with K outputs.

```
For i = 1, . . . , K
  For j = 0, . . . , d
    w_ij ← rand(−0.01,0.01)
Repeat
  For all (x^t, r^t) ∈ X in random order
    For i = 1, . . . , K
      o_i ← 0
      For j = 0, . . . , d
        o_i ← o_i + w_ij x^t_j
    For i = 1, . . . , K
      y_i ← exp(o_i) / Σ_k exp(o_k)
    For i = 1, . . . , K
      For j = 0, . . . , d
        w_ij ← w_ij + η (r^t_i − y_i)x^t_j
Until convergence
```

Where η is the learning factor.

The following is a Backpropagation Algorithm for training a MLP with K outputs.

```
Initialize all v_ih and w_hj to rand(−0.01,0.01)
Repeat
  For all (x^t, r^t) ∈ X in random order
    For h = 1, . . . , H
      z_h ← sigmoid(w^T_h x^t)
    For i = 1, . . . , K
      y_i = v^T_i z
    For i = 1, . . . , K
      Δ v_i = η (r^t_i − y^t_i) z
    For h = 1, . . . , H
      Δ w_h = η ( Σ_i (r^t_i − y^t_i) v_ih) z_h (1 − z_h) x^t
    For i = 1, . . . , K
      v_i ← v_i + Δ v_i
    For h = 1, . . . , H
      w_h ← w_h + Δ w_h
until convergence.
```

Figure 6:
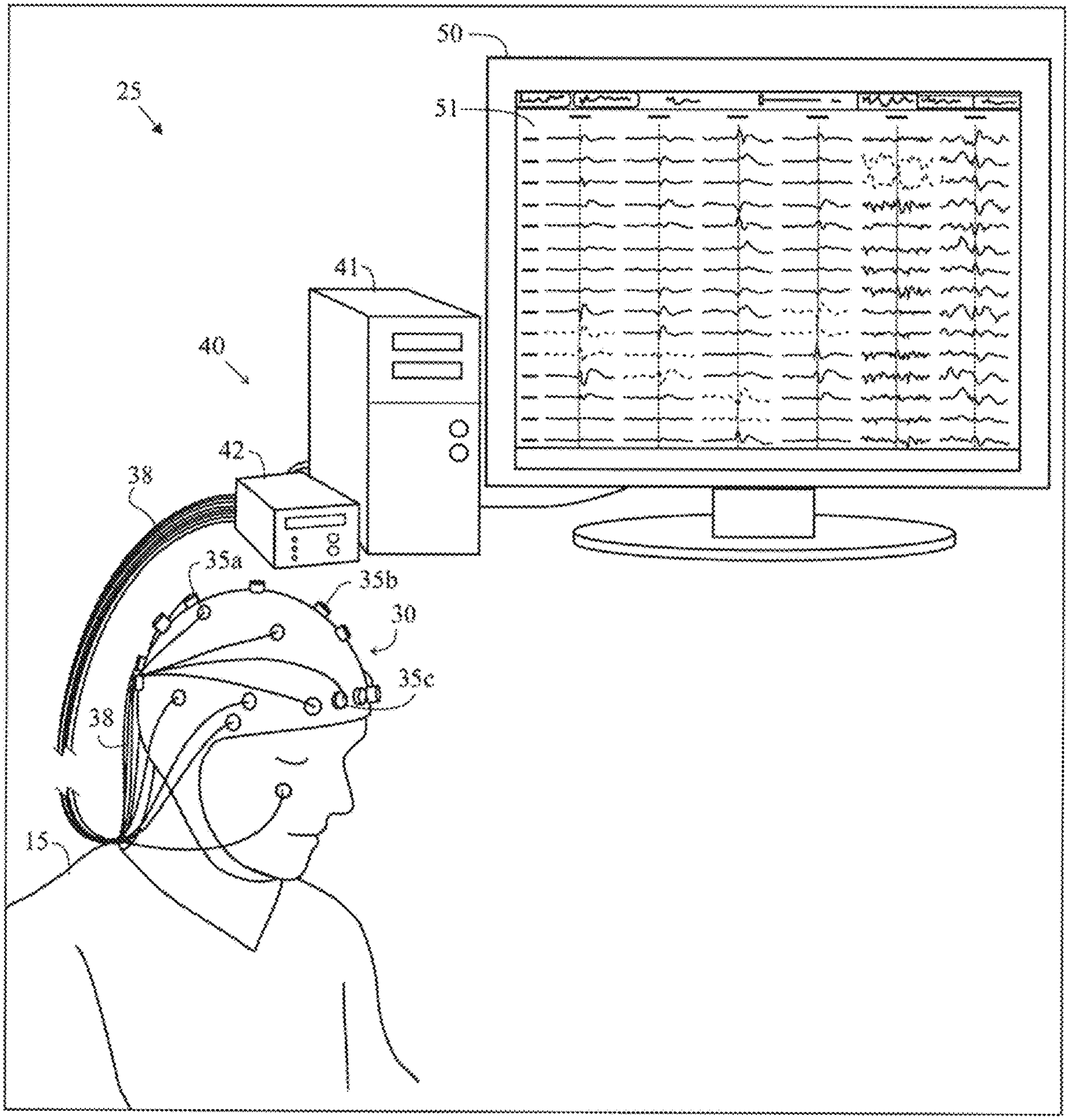
FIG. 6 is an illustration of an EEG system used on a patient.

FIG. 6 illustrates a system 25 for a user interface for automated artifact filtering for an EEG. A patient 15 wears an electrode cap 30, consisting of a plurality of electrodes 35*a*-35*c*, attached to the patient's head with wires 38 from the electrodes 35 connected to an EEG machine component 40 which consists of an amplifier 42 for amplifying the signal to a computer 41 with a processor, which is used to analyze the signals from the electrodes 35 and create an EEG recording 51, which can be viewed on a display 50.

Figure 7:
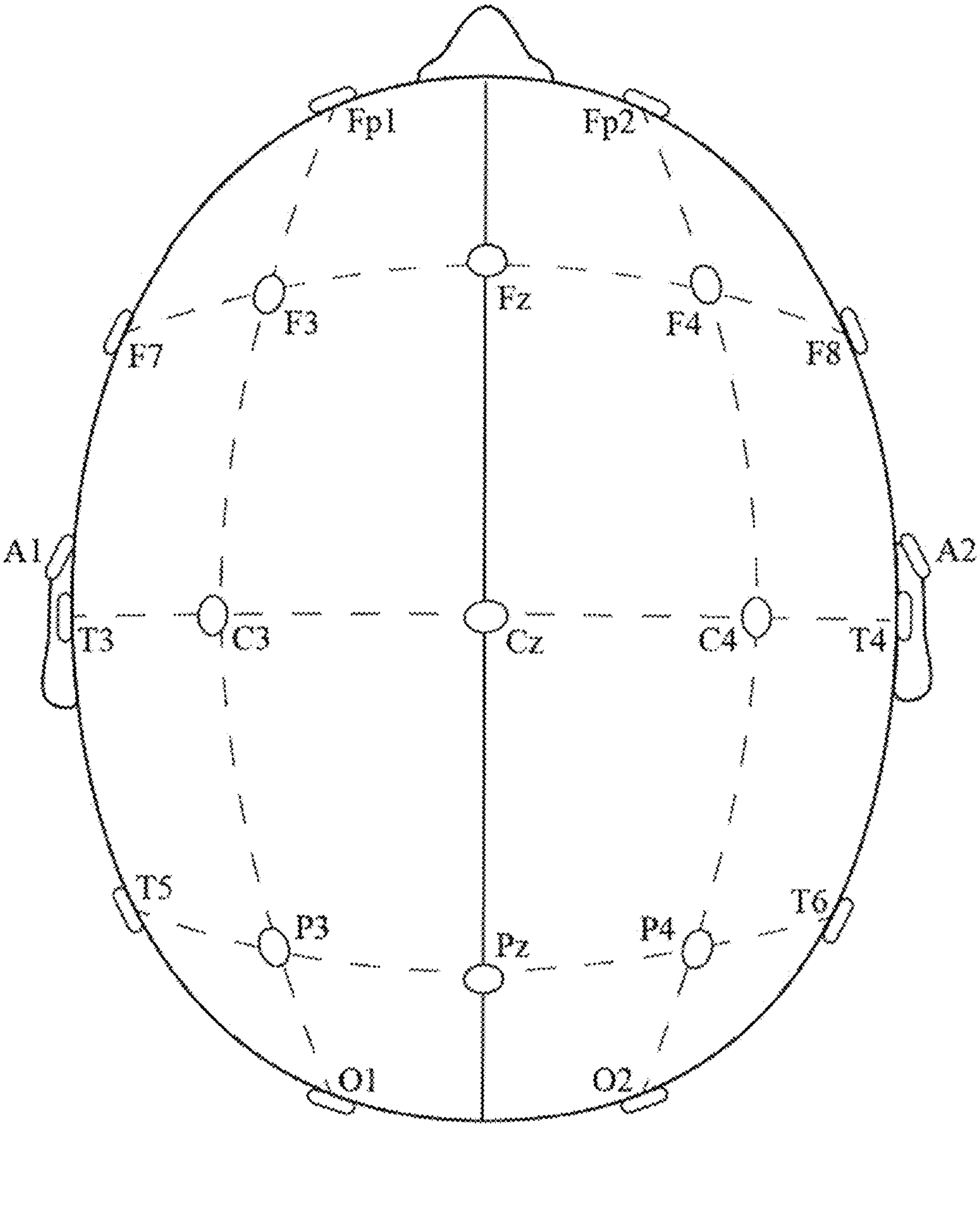
FIG. 7 is a map representing the international 10-20 electrode system for electrode placement for an EEG.
Figure 8:
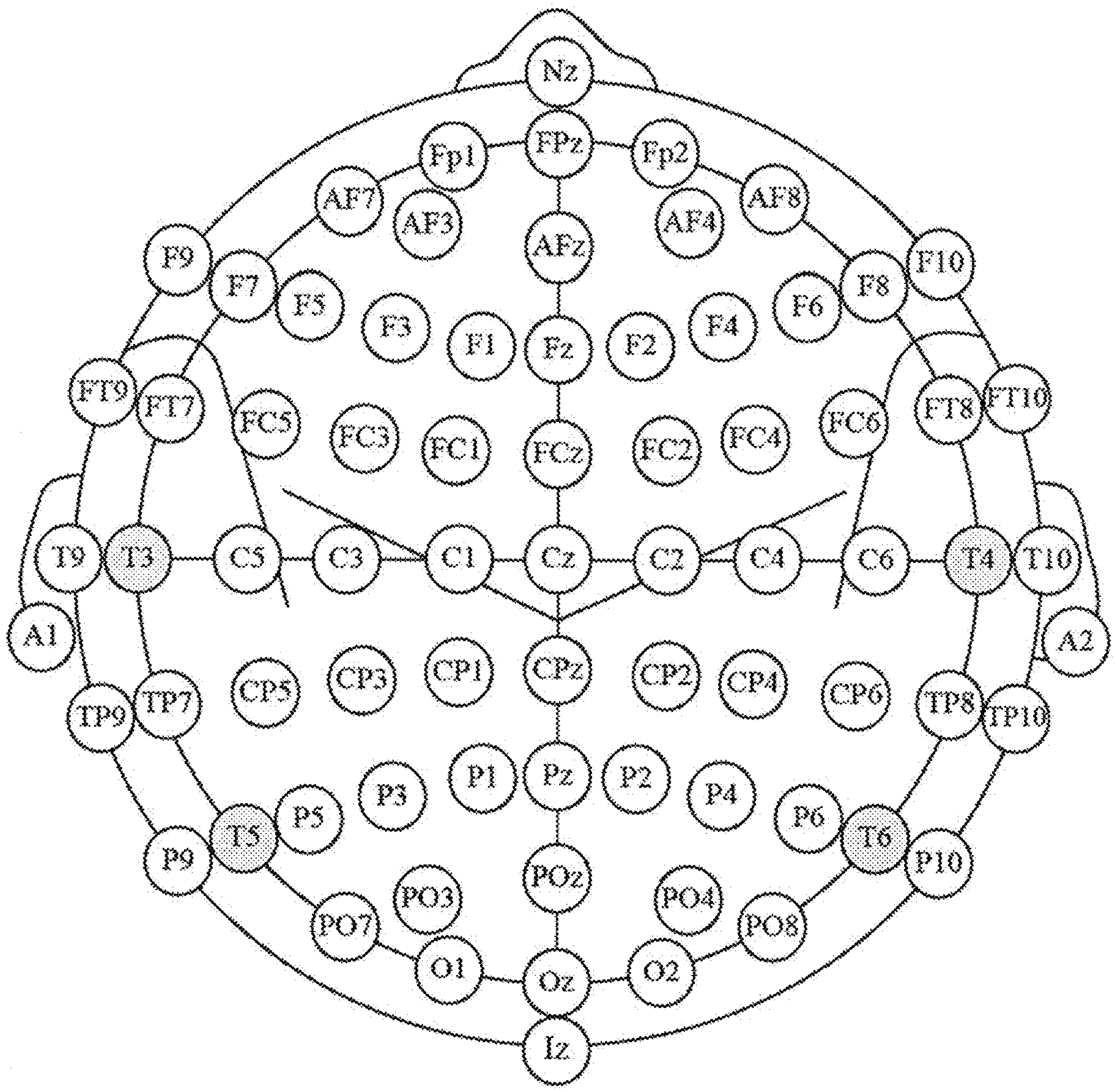
FIG. 8 is a detailed map representing the intermediate 10% electrode positions, as standardized by the American Electroencephalographic Society, for electrode placement for an EEG.

The brain produces different signals at different points on a patient's head. Multiple electrodes are positioned on a patient's head. The CZ site is in the center. The number of electrodes determines the number of channels for an EEG. A greater number of channels produce a more detailed representation of a patient's brain activity. Preferably, each amplifier 42 of an EEG machine component 40 corresponds to two electrodes 35 attached to a head of the patient 15. The output from an EEG machine component 40 is the difference in electrical activity detected by the two electrodes. The placement of each electrode is critical for an EEG report since the closer the electrode pairs are to each other, the less difference in the brainwaves that are recorded by the EEG machine component 40. FIG. 7 is a map representing the international 10-20 electrode system for electrode placement for an EEG. FIG. 8 is a detailed map representing the intermediate 10% electrode positions, as standardized by the American Electroencephalographic Society, for electrode placement for an EEG. A more thorough description of an electrode utilized with the present invention is detailed in Wilson et al., U.S. Pat. No. 8,112,141 for a Method And Device For Quick Press On EEG Electrode, which is hereby incorporated by reference in its entirety.

A button on computer 41, either through a keyboard or touchscreen button on display 50 allows for the application of a plurality of filters to remove the plurality of artifacts from the EEG and generate a clean EEG. The EEG is optimized for automated artifact filtering. The EEG recordings are then processed using neural network algorithms to generate a processed EEG recording, a raw score. The processor 41 is also configured to calibrate the raw score to generate a probability value that an event has occurred and then to generate a display of the probability value versus time. Further, the processor 41 is configured to validate the probability value. The processor is also connected to the display for displaying a final output.

An additional description of analyzing EEG recordings is set forth in Wilson et al., U.S. patent application Ser. No. 13/620,855, filed on Sep. 15, 2012, for a *Method And System For Analyzing An EEG Recording*, which is hereby incorporated by reference in its entirety.

Algorithms for removing artifact from EEG typically use Blind Source Separation (BSS) algorithms like CCA (canonical correlation analysis) and ICA (Independent Component Analysis) to transform the signals from a set of channels into a set of component waves or "sources." The sources that are judged as containing artifact are removed and the rest of the sources are reassembled into the channel set.

FIGS. 9, 9A, 9B and 9C illustrate a graphical display of the amount of artifact present in an EEG recording. An artifact intensity channel 110 is shown as a series of horizontal lines 111. The plurality of horizontal lines 111, shown in FIG. 9C, comprises a horizontal line 112 for a muscle artifact, a horizontal line 113 for a chewing artifact, a horizontal line 114 for a vertical eye movement artifact, and a horizontal line 115 for a lateral eye movement artifact. Those skilled in the pertinent art will recognize that more or less horizontal lines may be used without departing from the scope and spirit of the present invention.

Figure 9:
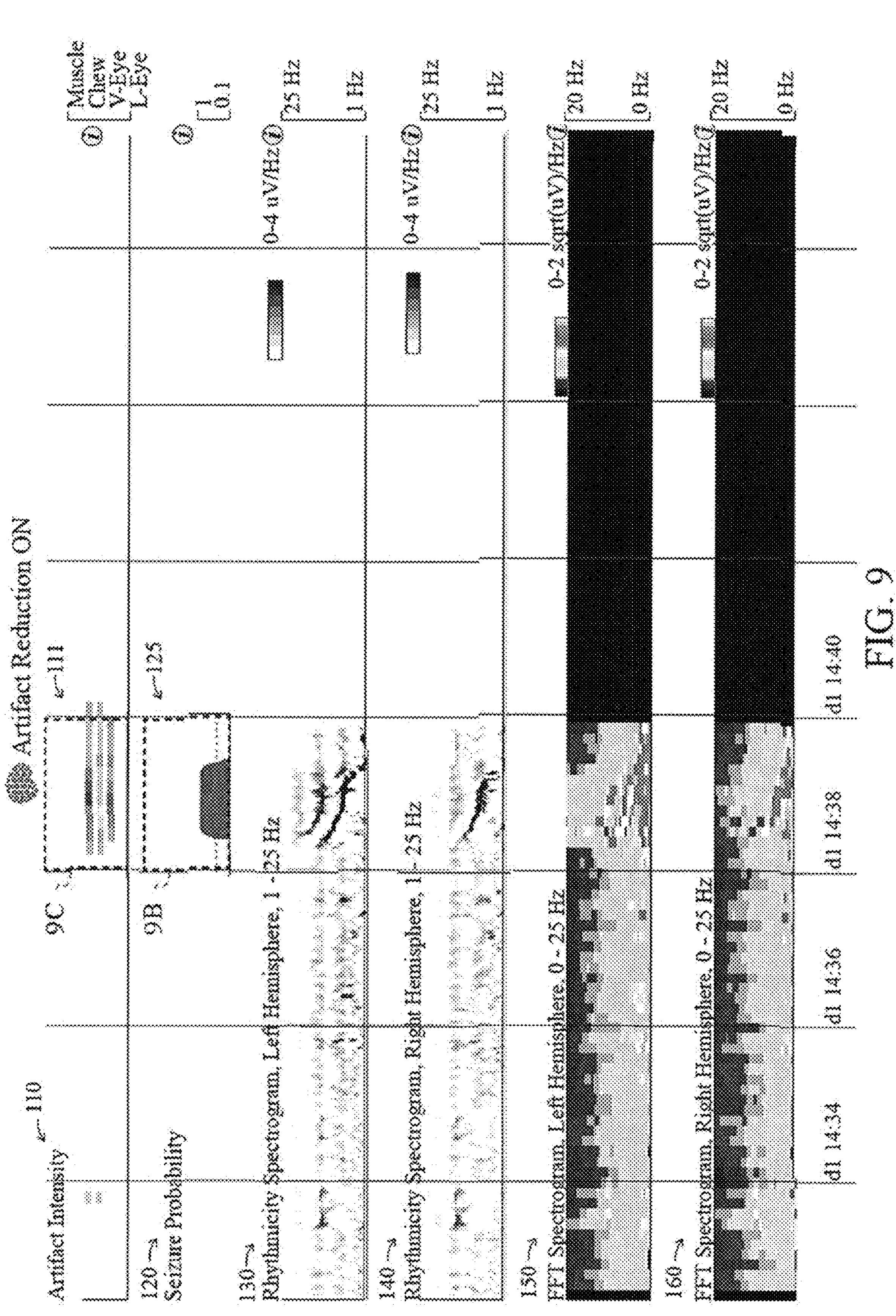
FIG. 9 is a graphical display of the amount of artifact present in an EEG recording.
Figure 9A:
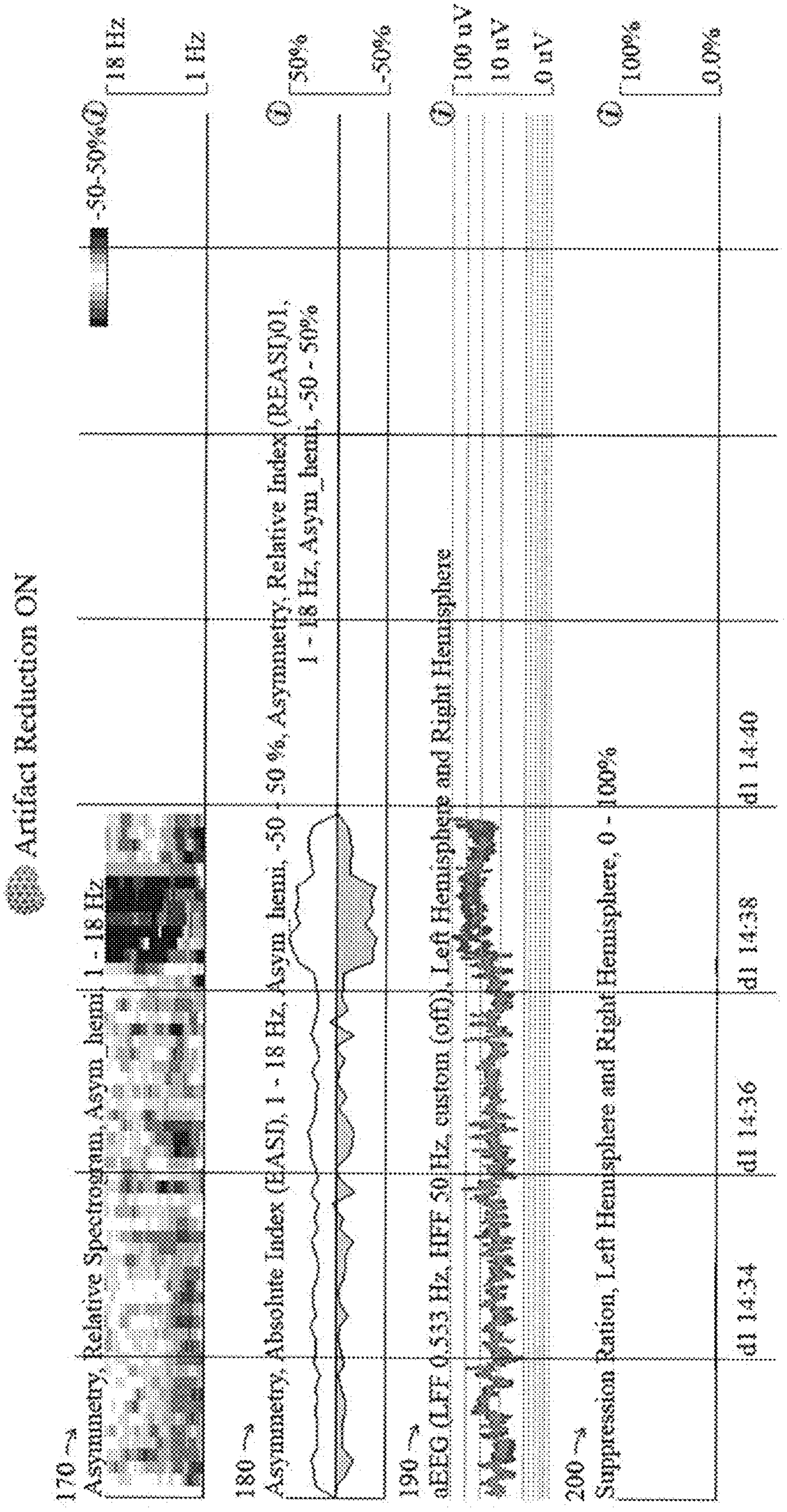
FIG. 9A is a graphical display of the amount of artifact present in an EEG recording.

Also shown in FIGS. 9 and 9A are a seizure probability channel 120, a rhythmicity spectrogram, left hemisphere channel 130, a rhythmicity spectrogram, right hemisphere channel 140, a FFT spectrogram left hemisphere channel 150, a FFT spectrogram right hemisphere channel 160, an asymmetry relative spectrogram channel 170, an asymmetry absolute index channel 180, an aEEG channel 190, and a suppression ration, left hemisphere and right hemisphere channel 200.

Rhythmicity spectrograms allow one to see the evolution of seizures in a single image. The rhythmicity spectrogram measures the amount of rhythmicity which is present at each frequency in an EEG record.

Figure 9B:
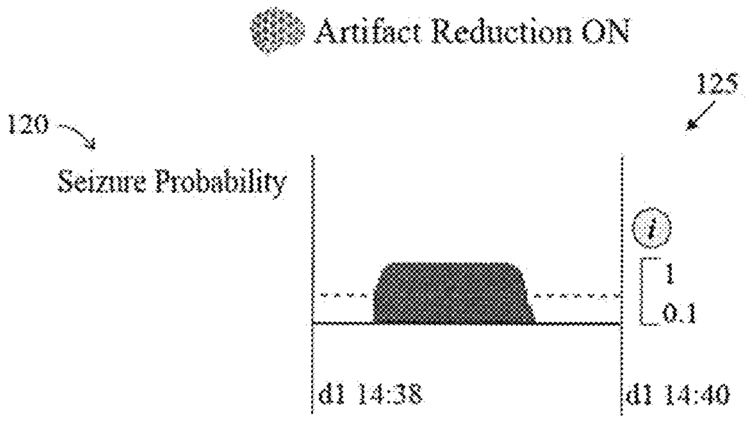
FIG. 9B is an enlarged and isolated view of a box 9B of a seizure probability channel of FIG. 9.
Figure 9C:
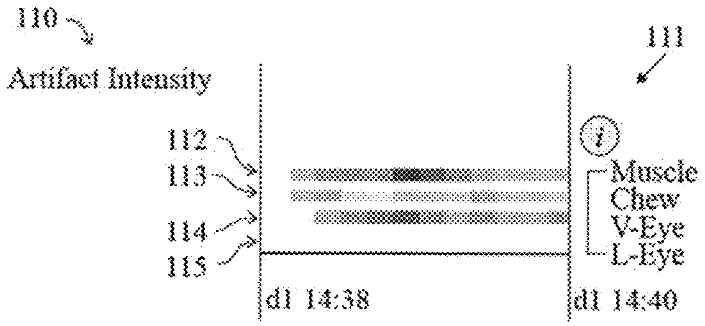
FIG. 9C is an enlarged and isolated view of horizontal lines of the artifact intensity channel of FIG. 9.

FIG. 9B shows the seizure being detected 125 in the seizure probability channel 120. The seizure probability trend shows a calculated probability of seizure activity over time. The seizure probability trend shows the duration of detected seizures, and also suggests areas of the record that may fall below the seizure detection cutoff, but are still of interest for review. The seizure probability trend when displayed along with other trends, provides a comprehensive view of quantitative changes in an EEG.

Figure 10:
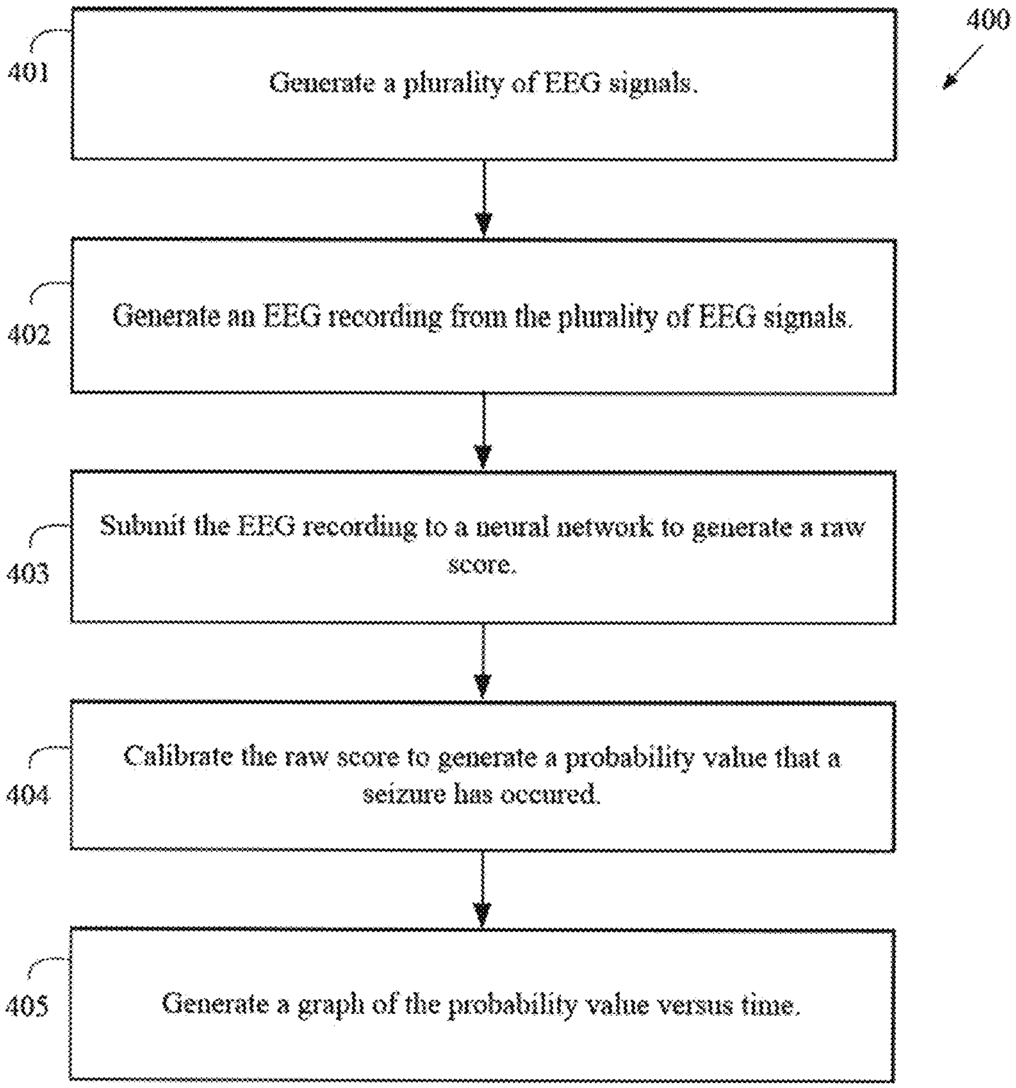
FIG. 10 is a flow chart of a method for generating a probability value for a seizure.

FIG. 10 shows a flow chart for a method, generally designated 400, of the present invention. A method 400 for validating a seizure probability for an EEG starts at step 401, generating a plurality a plurality of EEG signals. Step 402 is generating an EEG recording from the plurality of EEG signals. Step 403 is submitting the EEG recording to a neural network to generate a raw score. Step 404 is calibrating the raw score to generate a probability value that a seizure has occurred. Step 405 is generating a graph of the probability value versus time. The method 400 further includes validating the probability value (not shown).

Figure 11:
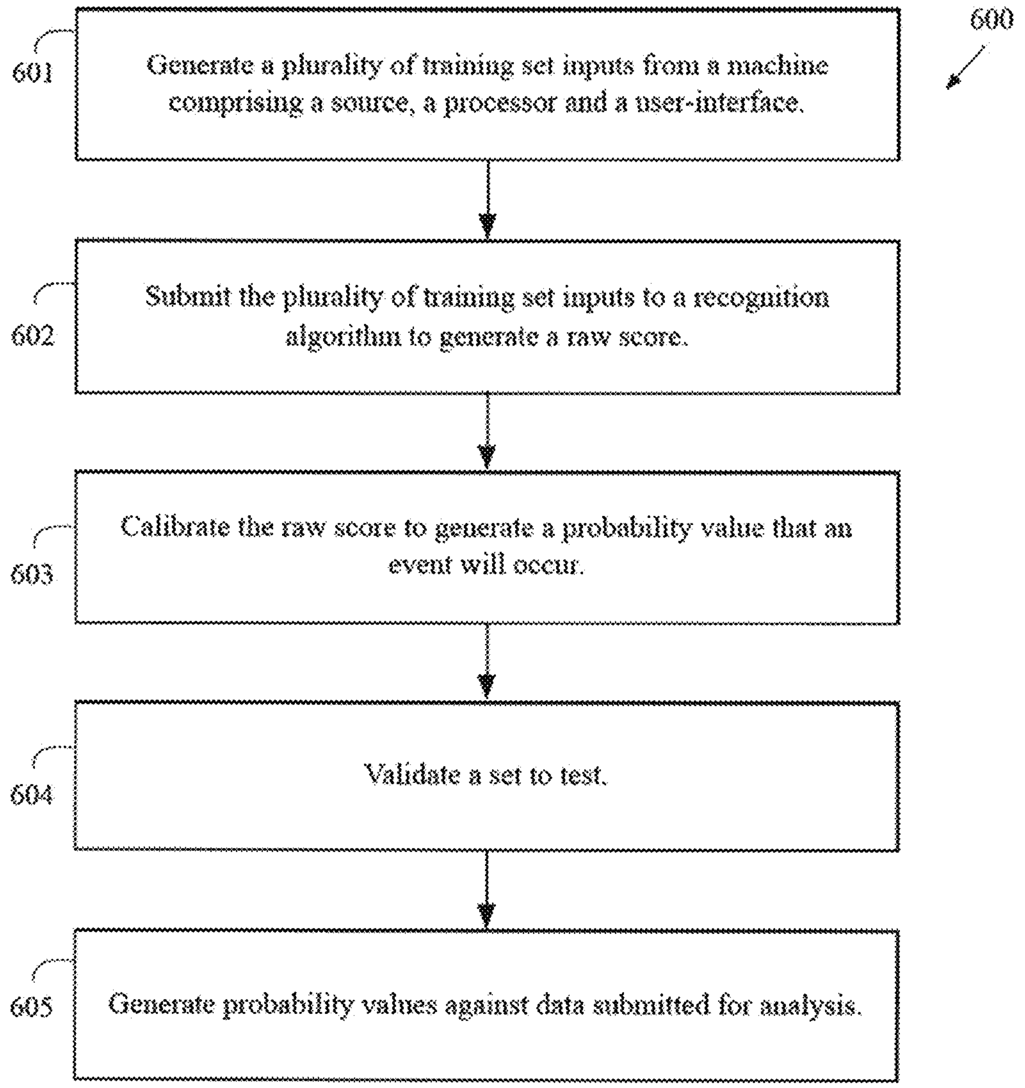
FIG. 11 is a flow chart of a method for validating a probability value for an event.

FIG. 11 shows a flow chart for a method, generally designated 600, of the present invention. A method 600 for generating a probability value for an event starts at block 601 where multiple training set inputs are generated from a machine comprising a source, a processor and a user-interface. At block 602, the multiple training set inputs are submitted to a recognition algorithm to generate a raw score. At block 603, the raw score is calibrated to generate a probability value that an event will occur. At block 604, a set is validated to test that the probability value is correct. At block 605, the probability values are generated against data submitted for analysis.

Figure 12:
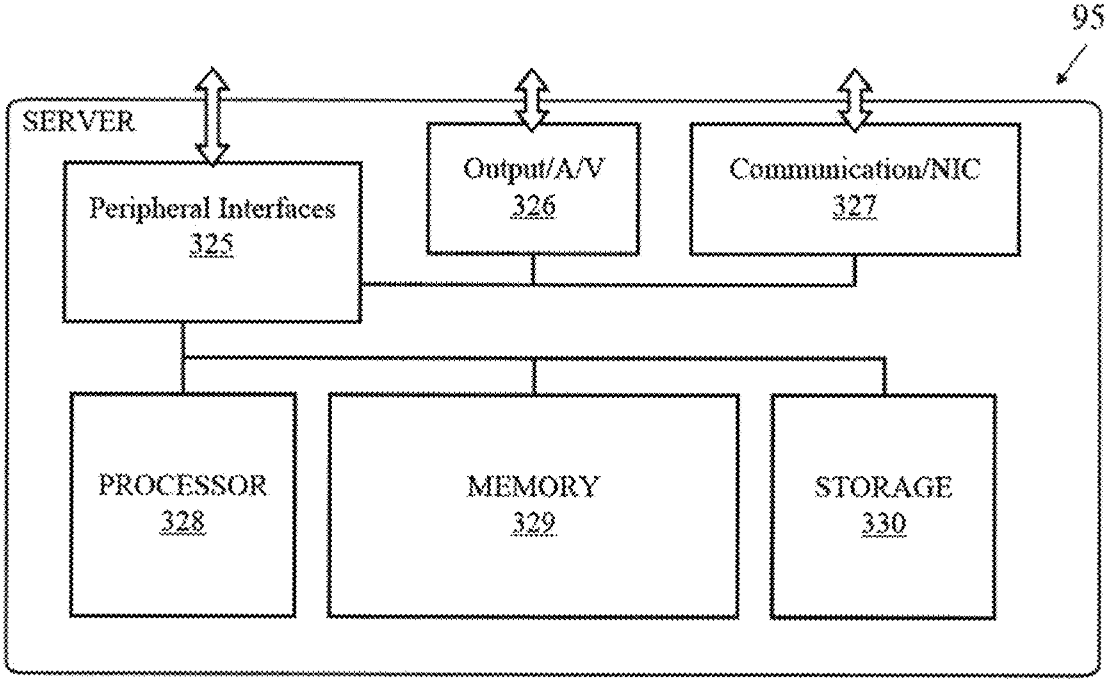
FIG. 12 is a block diagram of a computing device for EEG processing.

As shown in FIG. 12, the EEG machine component 95 preferably is a computer that includes peripheral interfaces 325, an output/A/V 326, a communication/NIC 327, a processor 328, a memory 329, and a storage 330. Those skilled in the pertinent art will recognize that the machine component 95 may include other components without departing from the scope and spirit of the present invention.

Figure 13A:
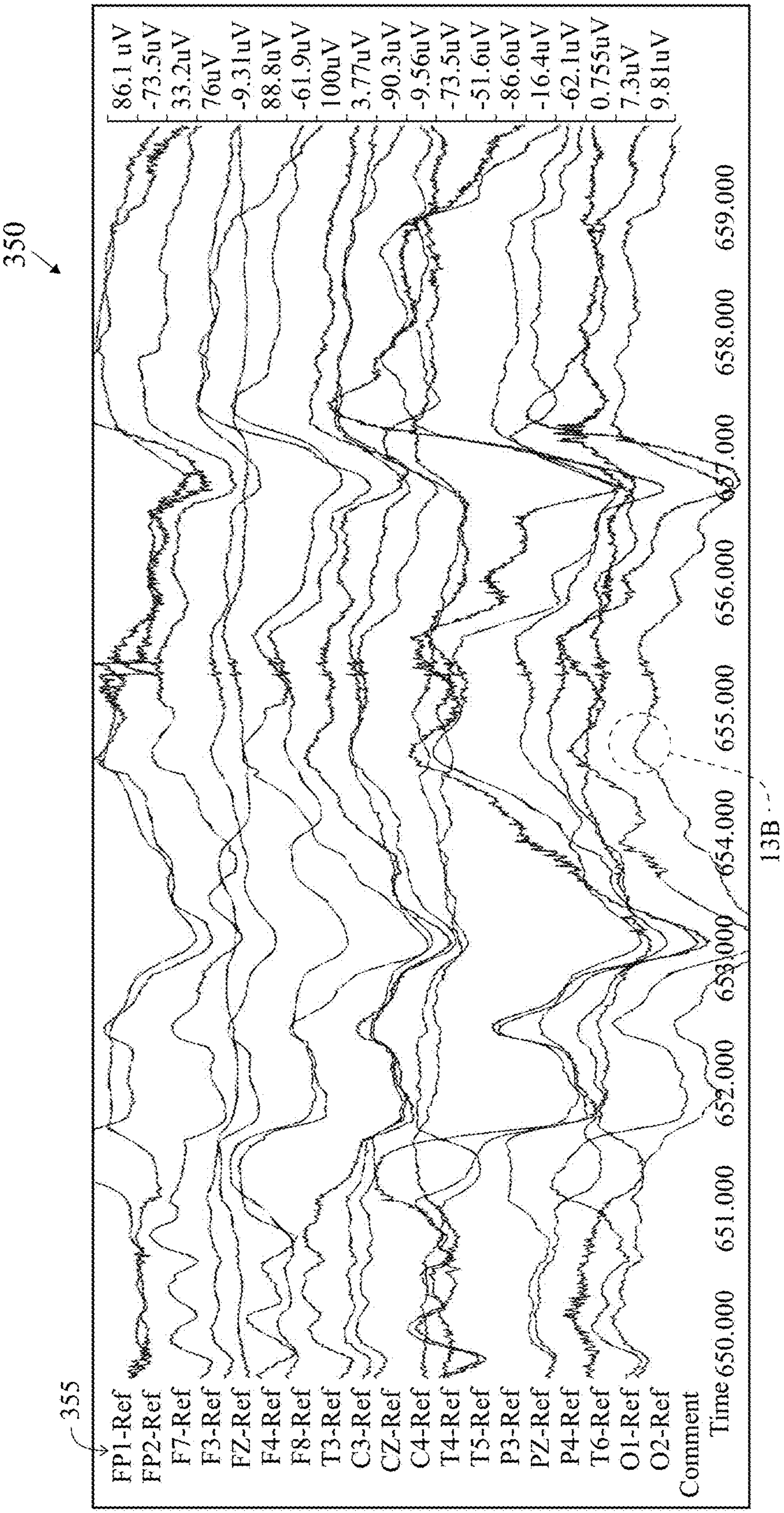
FIG. 13A is an illustration of a portion of a raw EEG report having nineteen channels.
Figure 13B:
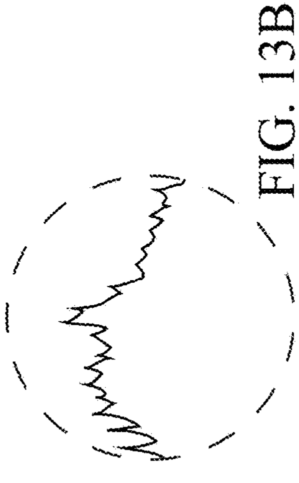
FIG. 13B is an enlargement of circle 13B of FIG. 13A.

A raw or original EEG report 350 is shown in FIG. 13A. The original EEG report 350 has a plurality of channels FP1-Ref through to O2-Ref, shown at the Y axis 355 of the report. The X-axis of the report is time. The original EEG report 350 has not been subjected to artifact reduction. The original EEG report 350 contains artifacts from various sources such as muscle movement, eye movement, sweating, electrode cables and the like. However, the EEG may also have certain activity that a physician or technician is looking for from the EEG report in order to accurately analyze the patient's brain activity. For example, the activity shown in FIG. 13B at a time 655.000 may represent a certain stage of brain activity for the patient that is important to the physician or technician. However, normally, the physician or technician will not review the raw EEG report 350 due to the presence of artifacts.

Figure 14A:
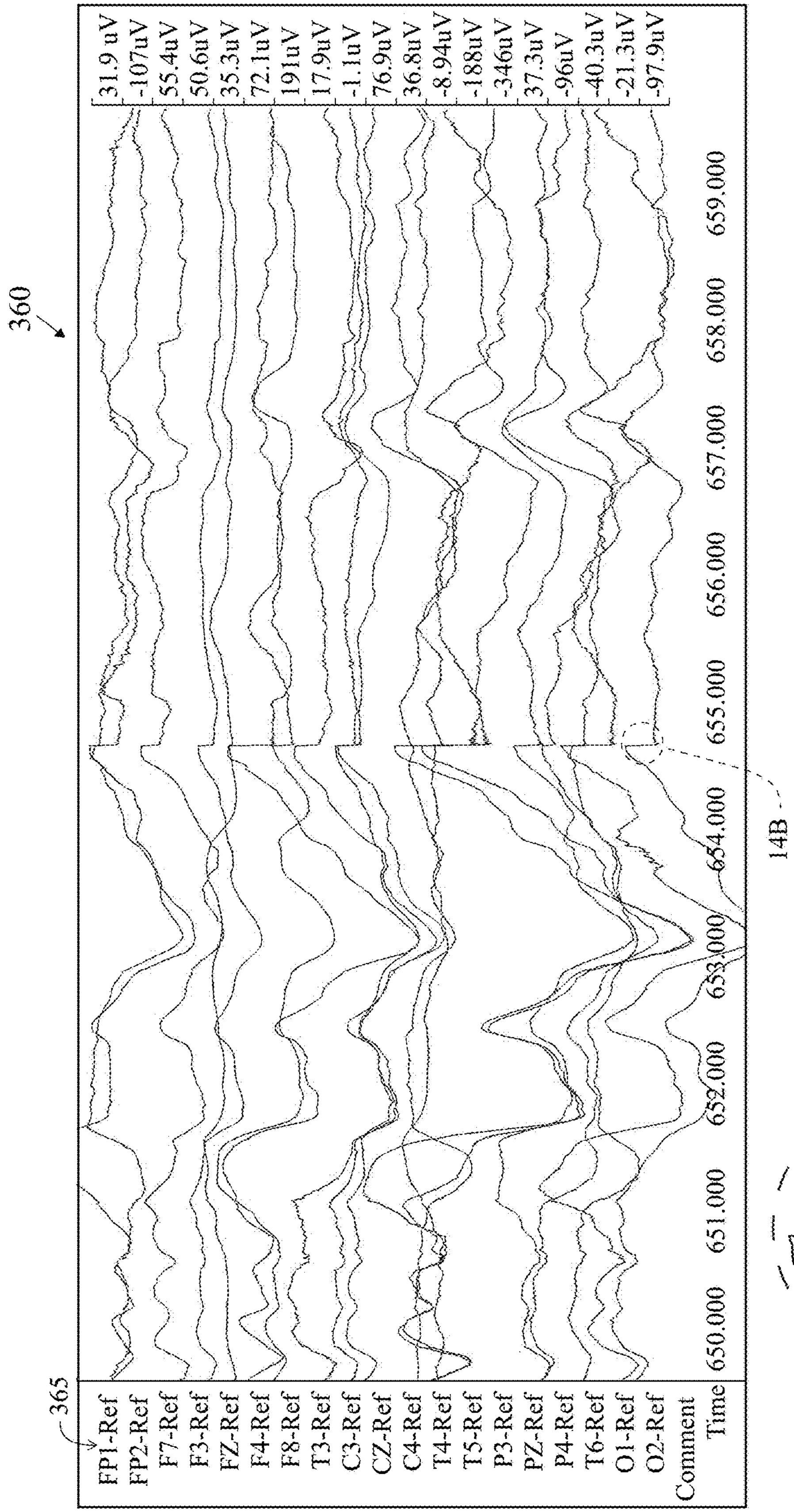
FIG. 14A is an illustration of a portion of a processed EEG report having nineteen channels in which epochs do not overlap.
Figure 14B:
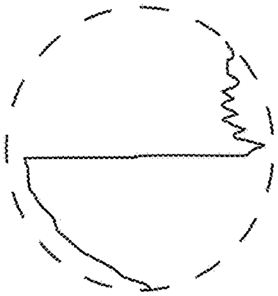
FIG. 14B is an enlargement of circle 14B of FIG. 14A.

FIG. 14A is an illustration of a processed EEG report 360 of the original EEG report 350 of FIG. 13A that has undergone artifact reduction and the stitching of epochs in order to recreate the EEG report. The processed EEG report 360 has a plurality of channels FP1-Ref through to O2-Ref, shown at the Y axis 365 of the report. The X-axis of the report is time. As shown in FIG. 14B, the processed EEG report 360 at time 655.000 is quite different in appearance than the original EEG report 350 at time 655.000 shown in FIG. 13B. This is primarily due to stitching of epochs to recreate the EEG report, however, if a physician or technician were only looking at the processed EEG report 360, the physician or technician would not be aware of the true activity at time 655.000.

Figure 15A:
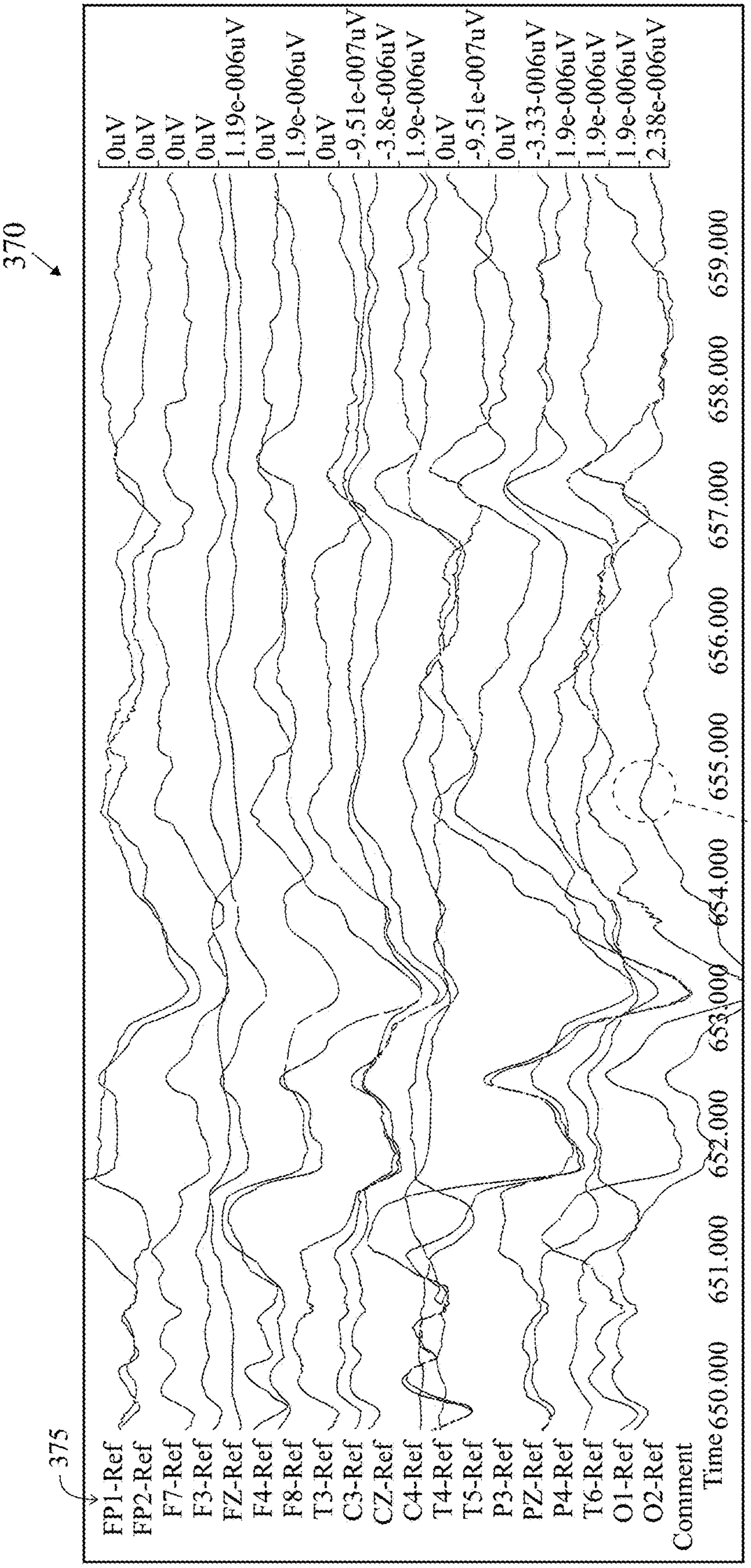
FIG. 15A is an illustration of a portion of a processed continuous EEG report in which sections of the epochs of the EEG report are stitched to overlap.
Figure 15B:
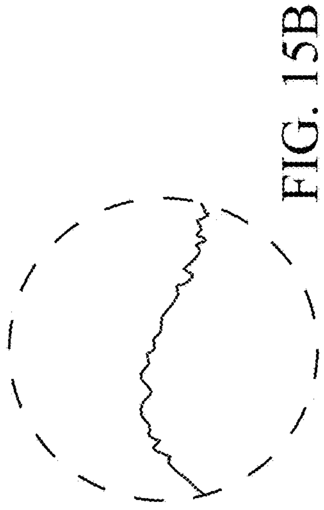
FIG. 15B is an enlargement of circle 15B of FIG. 15A.

FIG. 15A is an illustration of a processed continuous EEG report 370 of the original EEG report 350 of FIG. 13A that has undergone artifact reduction and the stitching of overlapping epochs in order to recreate the EEG report. The processed continuous EEG report 370 has a plurality of channels FP1-Ref through to O2-Ref, shown at the Y axis 375 of the report. The X-axis of the report is time. As shown in FIG. 15B, the processed continuous EEG report 370 at time 655.000 is more similar in appearance to the original EEG report 350 at time 655.000 than the processed EEG report 360 of FIG. 14A. However, there is still difficulty in analyzing a patient's brain activity by switching back and forth from an original EEG report 350 to a processed EEG report 360 or a processed continuous EEG report 370.

Figure 16A:
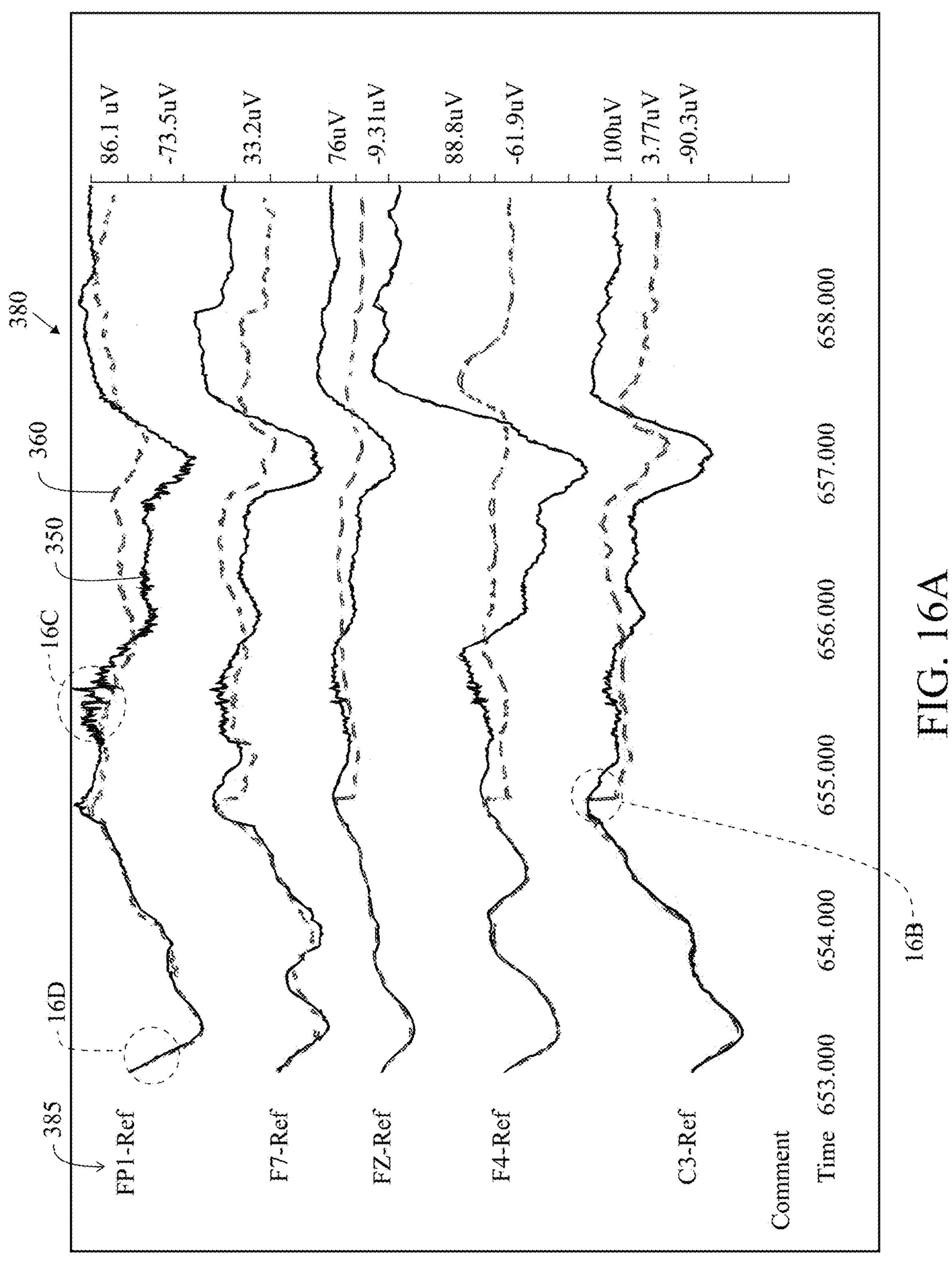
FIG. 16A is an illustration of a portion of a combined EEG report having a processed EEG report overlay on a raw EEG report.

FIG. 16A is an illustration of a combined EEG report 380 comprising the original EEG report 350 and the processed EEG report 360. The illustration of the combined EEG report 380 only has five channels in order to clearly illustrate the invention, however, those skilled in the pertinent art will recognize that the combined EEG report 380 could have sixteen, twenty, twenty-seven or any number of channels without departing from the scope and spirit of the present invention.

Figure 16B:
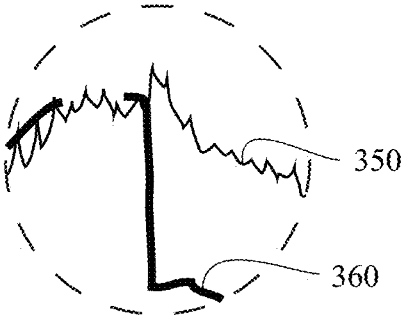
FIG. 16B is an enlargement of circle 16B of FIG. 16A.
Figure 16C:
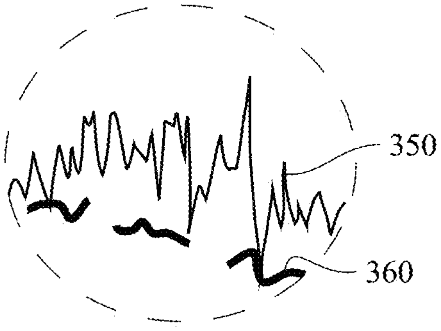
FIG. 16C is an enlargement of circle 16C of FIG. 16A.
Figure 16D:
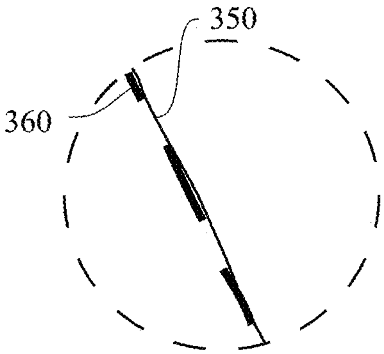
FIG. 16D is an enlargement of circle 16D of FIG. 16A.

As shown in FIGS. 16B, 16C, and 16D, the original EEG report 350 has a first line style and the processed EEG report 360 has a second line style distinctive from the first line style in order to allow a physician and technician to easily and visually distinguish between the original EEG report 350 and the processed EEG report 360. In an alternative embodiment, the original EEG report 350 has a first color (e.g., blue) and the processed EEG report 360 has a second color (e.g. red) distinctive from the first color in order to allow a physician and technician to easily and visually distinguish between the original EEG report 350 and the processed EEG report 360.

As shown in FIG. 16A and specifically FIG. 16D, the channels of the original EEG report 350 are aligned with the channels of the processed EEG report 360 in order to have y-axis 385 alignment.

As shown in FIG. 16A and specifically in FIG. 16B, the x-axis of the original EEG report 350 are aligned with the x-axis of the processed EEG report 360 in order to have time alignment of the two EEG reports in the combined EEG report 380.

Further, the amplitudes for both the original EEG report 350 and the processed EEG report 360 are contained within each of the channels in order to prevent overlapping of the signals.

As shown in FIG. 16C, the original EEG report 350 is quite different from the processed EEG report 360 and a physician or technician may be interested in the activity shown in the original EEG report 350 as compared to the processed EEG report 360.

Those skilled in the pertinent art will recognize that the processed continuous EEG report 370 may be substituted for the processed EEG report 360 in FIG. 16A in order to demonstrate a comparison between the original EEG report 350 and the processed continuous EEG report 370.

Figure 17:
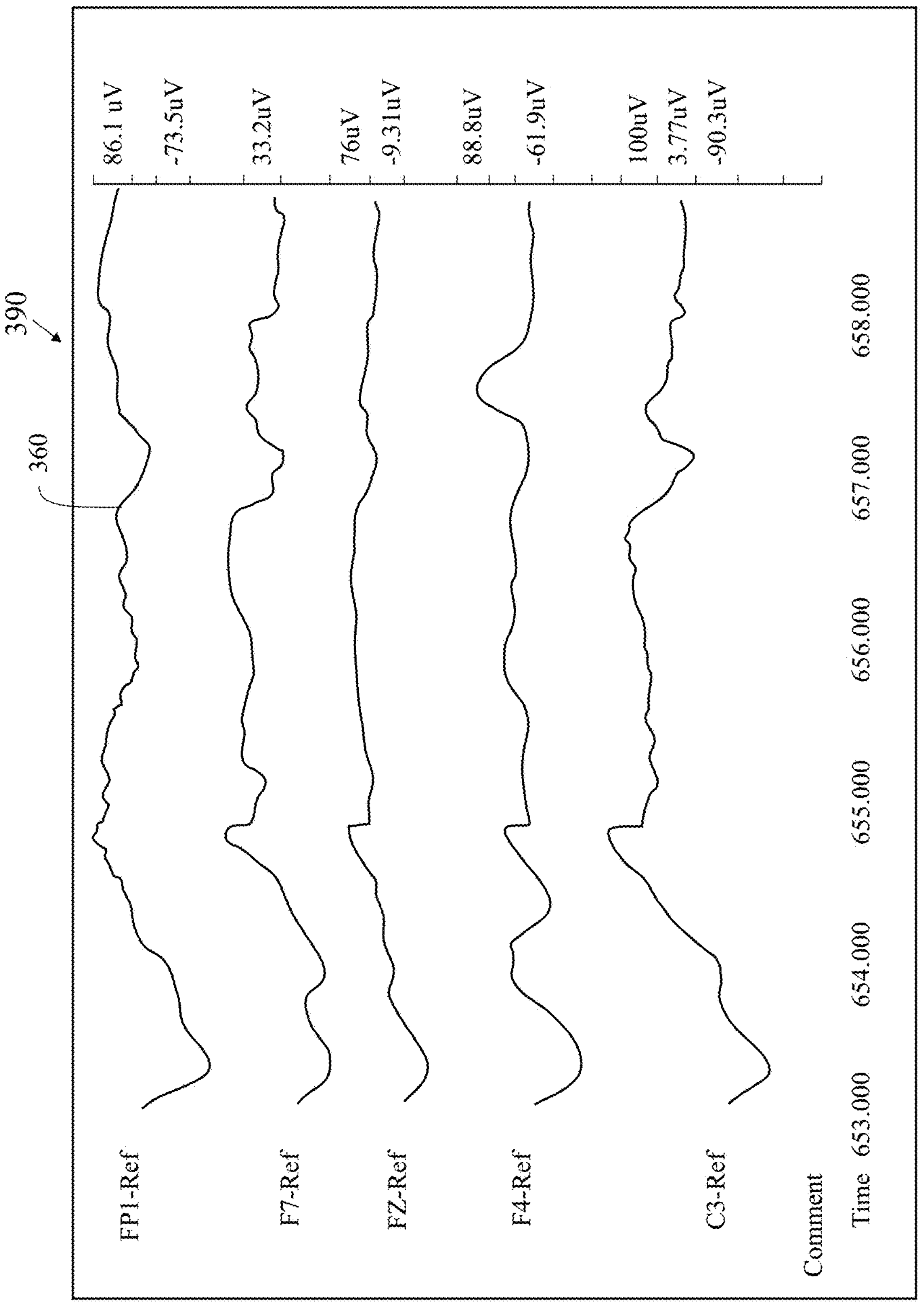
FIG. 17 is an illustration of a portion of processed continuous EEG report in which sections of the epochs of the EEG report are stitched to overlap.

FIG. 17 is an illustration of an EEG report 390, based on the EEG report 370 of FIG. 15A, in which channels have been removed for a clearer illustration of channels. The illustration of the combined EEG report 390 only has five channels in order to clearly illustrate the invention, however, those skilled in the pertinent art will recognize that the combined EEG report 390 could have sixteen, twenty, twenty-seven or any number of channels without departing from the scope and spirit of the present invention.

A flow chart for a method 700 for displaying EEG data is shown in FIG. 18. At block 701, an original EEG report is generated from an EEG signal. The original EEG report is generated from an EEG machine comprising a plurality of electrodes, an amplifier, and a processor. The original EEG report comprises a first plurality of channels. At block 702, the original EEG signal is partitioned from a set of channels into epochs of which each has a predetermined duration length and an overlap increment. At block 703, artifact reduction is performed on the epochs to generate artifact reduced epochs. At block 704, the artifact reduced epochs are combined with overlapping adjacent epochs for a continuous EEG recording to generate a processed continuous EEG report. The stitched, overlapping epochs and continuous processed EEG report is displayed on a display screen, preferably a monitor. The stitched overlapping epochs and continuous processed EEG report are not missing timeframes from stitching or creating discontinuities in the EEG report, which is read by a physician or technician. All of the brain activity remains since the epochs overlap. The brain activity is preferably spikes, sharp waves, spike and wave discharges, artifacts, and the like.

Figure 19:
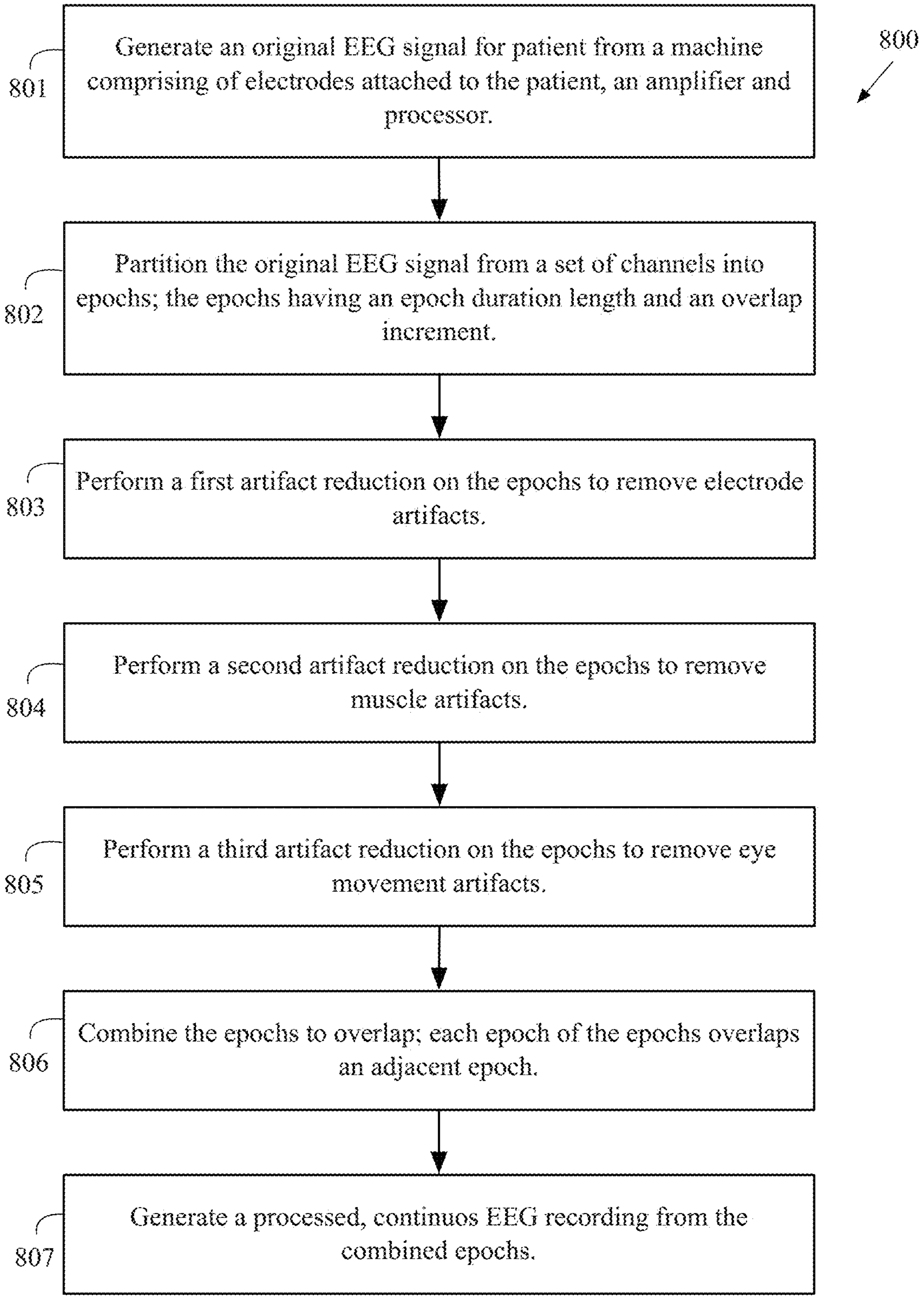
FIG. 19 is a flow chart for a method of artifact reduction.

FIG. 19 is a flow chart of a preferred method 800 for displaying EEG data. At block 801, an original EEG report is generated from an EEG signal for a patient from a machine preferably comprising electrodes attached to the patient, an amplifier and a processor. At block 802, the original EEG signal is partitioned from a set of channels into a plurality of epochs. Each of the plurality of epochs having an epoch duration length and an overlap increment. At block 803, a first artifact reduction is performed on the plurality of epochs to remove electrode artifacts. At block 804, a second artifact reduction is performed on the plurality of epochs to remove muscle artifacts. At block 805, a third artifact reduction is performed on the plurality of epochs to remove eye movement artifacts. At block 806, the plurality of epochs is combined to overlap wherein each epoch of the plurality of epochs overlaps an adjacent epoch to form a processed continuous EEG report. At block 807, a processed continuous EEG recording is generated from the combined epochs.

Each of the plurality of epochs preferably has an epoch duration length of two seconds and an increment of one second. Alternatively, each of the plurality of epochs has an epoch duration length of four seconds and an increment of two seconds. The artifact removal algorithm is preferably a blind source separation algorithm. The blind source separation algorithm is preferably a CCA algorithm or an ICA algorithm. The clean epochs are preferably combined using a weighted average and the weight of the weighted average is preferably proportional to the ratio of the distance to an epoch center.

Figure 20:
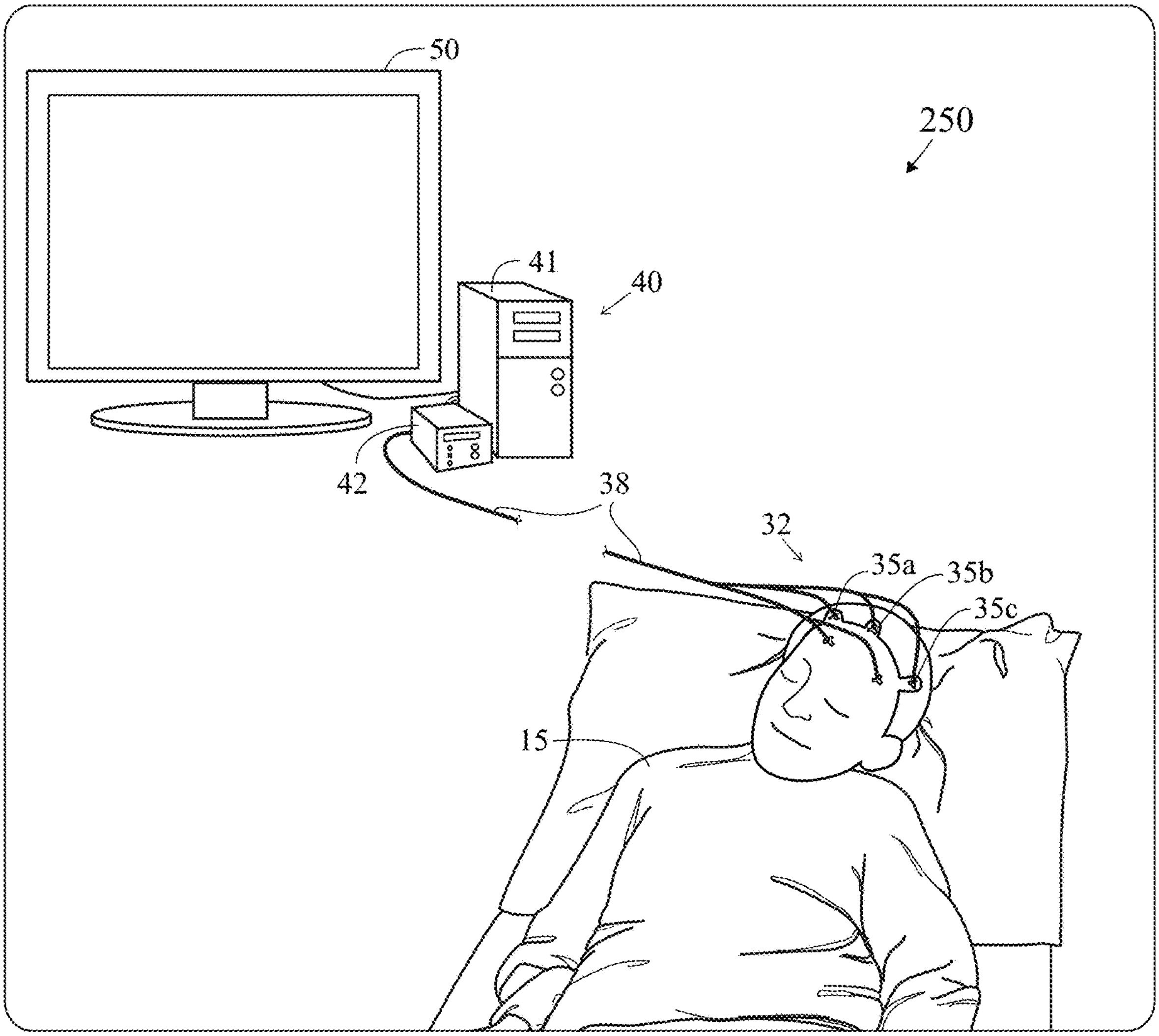
FIG. 20 is an illustration of an EEG system used on a patient.
Figure 21:
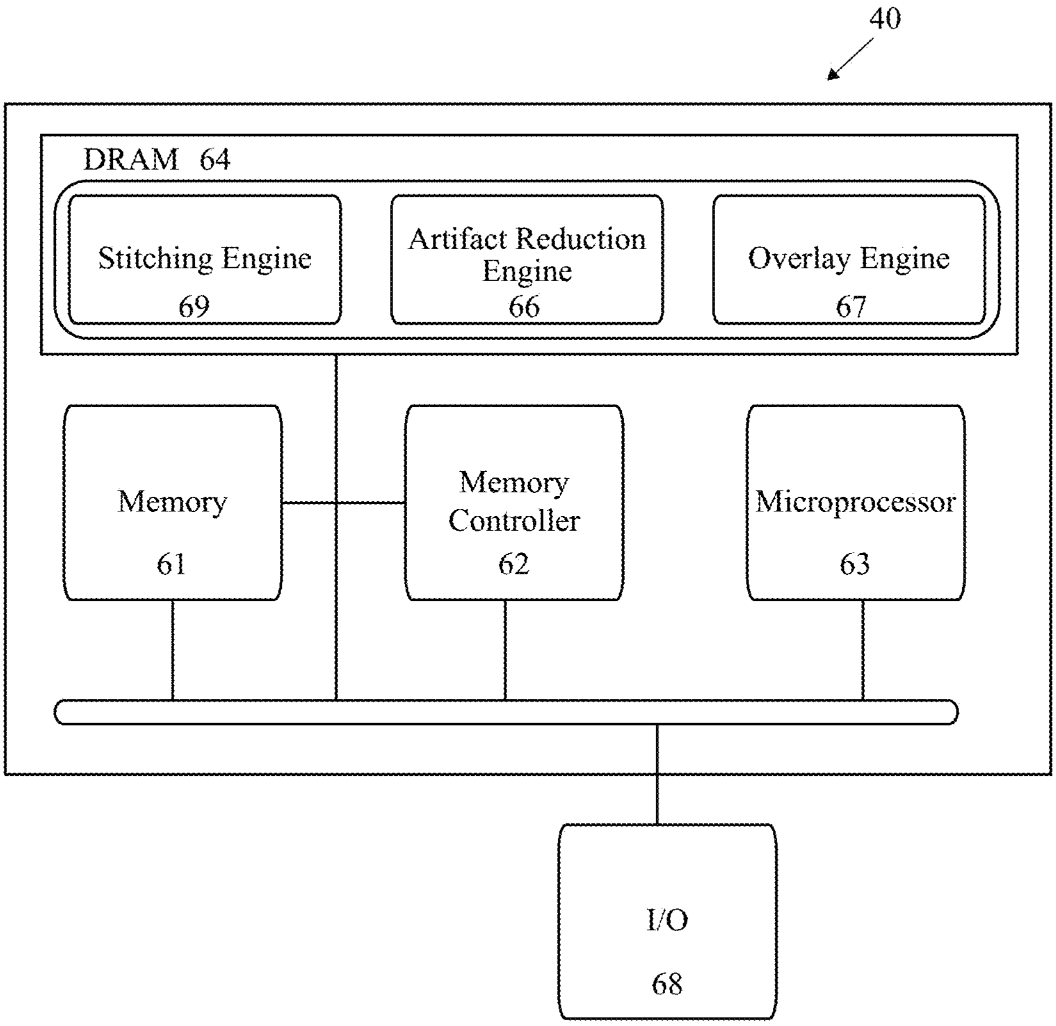
FIG. 21 is a block diagram of an EEG machine component of an EEG system.

As shown in FIG. 20, an EEG system is generally designated 250. The system preferably includes a patient component 32, an EEG machine component 40 and a display component 50. The patient component 32 includes a plurality of electrodes **35*a*, 35*b*, 35*c* attached to the patient 15 and wired by cables 38 to the EEG machine component 40. The EEG machine component 40 comprises a CPU 41 and an amplifier component 42. The EEG machine component 40 is connected to the display component 50 for display of the combined EEG reports, and for switching from a processed EEG report to the combined EEG reports, or from the processed EEG report to an original EEG report. As shown in FIG. 21, the EEG machine component 40 preferably includes a stitching engine 69, an artifact reduction engine 66, an overlay engine 67, a memory 61, a memory controller 62, a microprocessor 63, a DRAM 64, and an Input/Output 68. Those skilled in the pertinent art will recognize that the machine component 40** may include other components without departing from the scope and spirit of the present invention.

Figure 22:
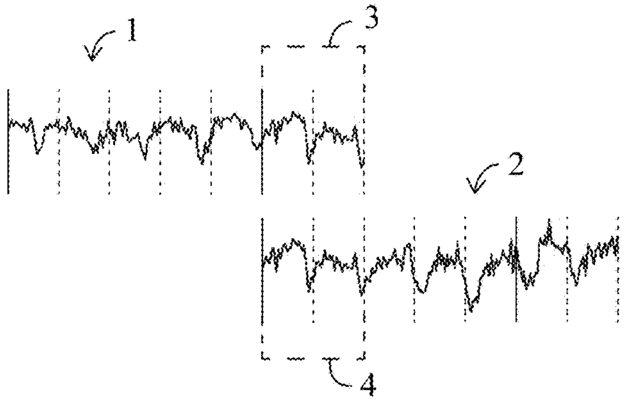
FIG. 22 is an illustration of isolated adjacent epochs.

FIG. 22 is an isolated view of adjacent unprocessed epochs 1 and 2. Epoch 1 has an overlapping portion 3 and epoch 2 has an overlapping portion 4. In this example, the overlapping portions 3 and 4 are approximately two seconds in length. Thus, overlapping portions 3 and 4 represent the same timeframe (two seconds) for a raw EEG recording.

Figure 23:
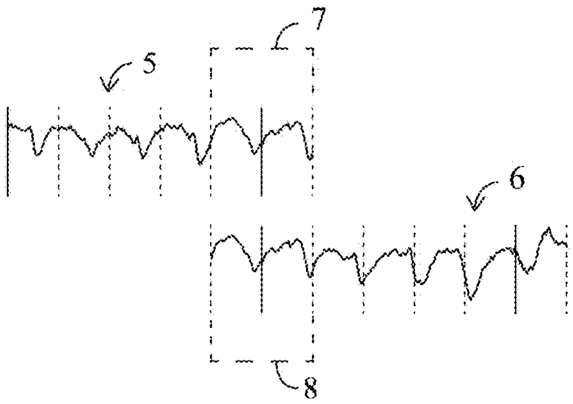
FIG. 23 is an illustration of isolated adjacent epochs.

FIG. 23 is an illustration of adjacent processed epochs 5 and 6. Artifact reduction has been performed on these epochs 5 and 6. Processed epochs 5 and 6 represent the same timeframe as unprocessed epochs 1 and 2. Thus, epoch 5 is the result of artifact reduction of unprocessed epoch 1, and epoch 6 is the result of artifact reduction of unprocessed epoch 2. Processed epoch 5 has an overlapping portion 7 and processed epoch 6 has an overlapping portion 8. Thus, overlapping portions 7 and 8 represent the same timeframe (two seconds) for the processed EEG recording. Further, overlapping portion 7 is the same timeframe as overlapping portion 3 and overlapping portion 8 is the same timeframe as overlapping portion 4. Further overlapping portions 3, 4, 7 and 8 represent all the same timeframe.

Figure 24:
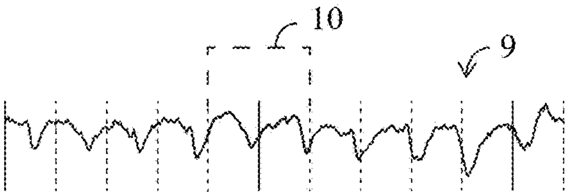
FIG. 24 is an illustration of epochs stitched together with an overlapping portion.

FIG. 24 is an illustration of the stitching of adjacent processed epochs 5 and 6 into a section of continuous processed EEG recording 9. Portion 10 is the overlapping portions 7 and 8 from adjacent processed epochs 5 and 6. As shown, no information is lost, and the processed EEG recording is continuous, without abrupt termination points where epochs have been stitched together.

Figure 25:
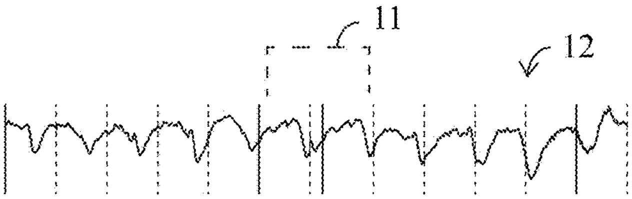
FIG. 25 is an example of prior art combining of epochs resulting in discontinuous or missing information from the processed and stitched EEG recording.

FIG. 25 is an illustration of the prior art approach of stitching of epochs without overlapping portions. The section 12 of the processed EEG recording has a stitching portion 11, which has changed from the same timeframe of the processed epochs 5 and 6. The stitching portion 11 is different from section 10 of FIG. 24.

Figure 27:
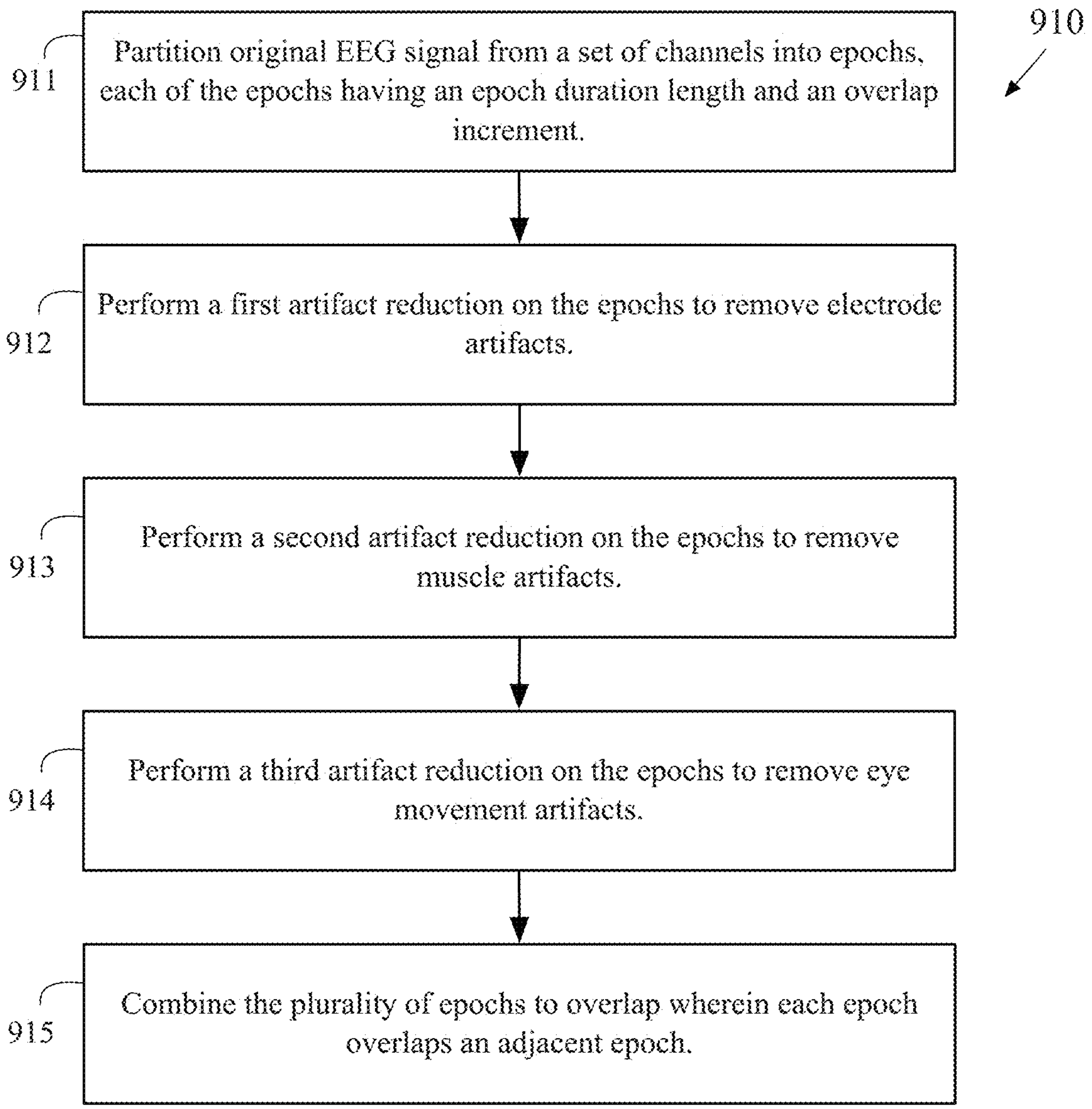
FIG. 27 is a flow chart for a method of artifact reduction.

A flow chart for a method 900 for displaying EEG data is shown in FIG. 26. At block 901, an original EEG report is generated from an EEG signal. The original EEG report is generated from an EEG machine comprising a plurality of electrodes and processor. The original EEG report comprises a first plurality of channels. At block 902, artifact reduction is performed on the original EEG signal to generate a processed EEG report. The processed EEG report comprises a second plurality of channels. At block 903, the processed EEG report overlays the original EEG report to generate a combined EEG report. An x-axis of the processed EEG report is aligned with an x-axis of the original EEG report. A y-axis of the processed EEG report is aligned with a y-axis of the original EEG report. The first plurality of channels of the original EEG report are equal to the second plurality of channels of the processed EEG report. At block 904, the combined EEG report is displayed on a display screen, preferably a monitor. The processed EEG report is visually distinctive from the original EEG report. An activity at a specific time on one channel of the first plurality of channels of the original EEG report is identifiable on a corresponding channel of the second plurality of channels of the processed EEG report at the specific time. The activity is preferably spikes, sharp waves, spike and wave discharges, artifacts, and the like FIG. 27 is a flow chart of a preferred method 910 for artifact reduction of raw EEG data. At block 911, the original EEG signal is portioned from a set of channels into a plurality of epochs. Each of the plurality of epochs having an epoch duration length and an overlap increment. At block 912, a first artifact reduction is performed on the plurality of epochs to remove electrode artifacts. At block 913, a second artifact reduction is performed on the plurality of epochs to remove muscle artifacts. At block 914, a third artifact reduction is performed on the plurality of epochs to remove eye movement artifacts. At block 915, the plurality of epochs is combined to overlap wherein each epoch of the plurality of epochs overlaps an adjacent epoch to form a processed continuous EEG report.

Each of the plurality of epochs has an epoch duration length of two seconds and an increment of one second. Alternatively, each of the plurality of epochs has an epoch duration length of four seconds and an increment of two seconds. The artifact removal algorithm is preferably a blind source separation algorithm. The blind source separation algorithm is preferably a CCA algorithm or an ICA algorithm. The clean epochs are preferably combined using a weighted average and the weight of the weighted average is preferably proportional to the ratio of the distance to an epoch center.

FIGS. 28-32 illustrate analyzed EEG recordings.

Figure 28:
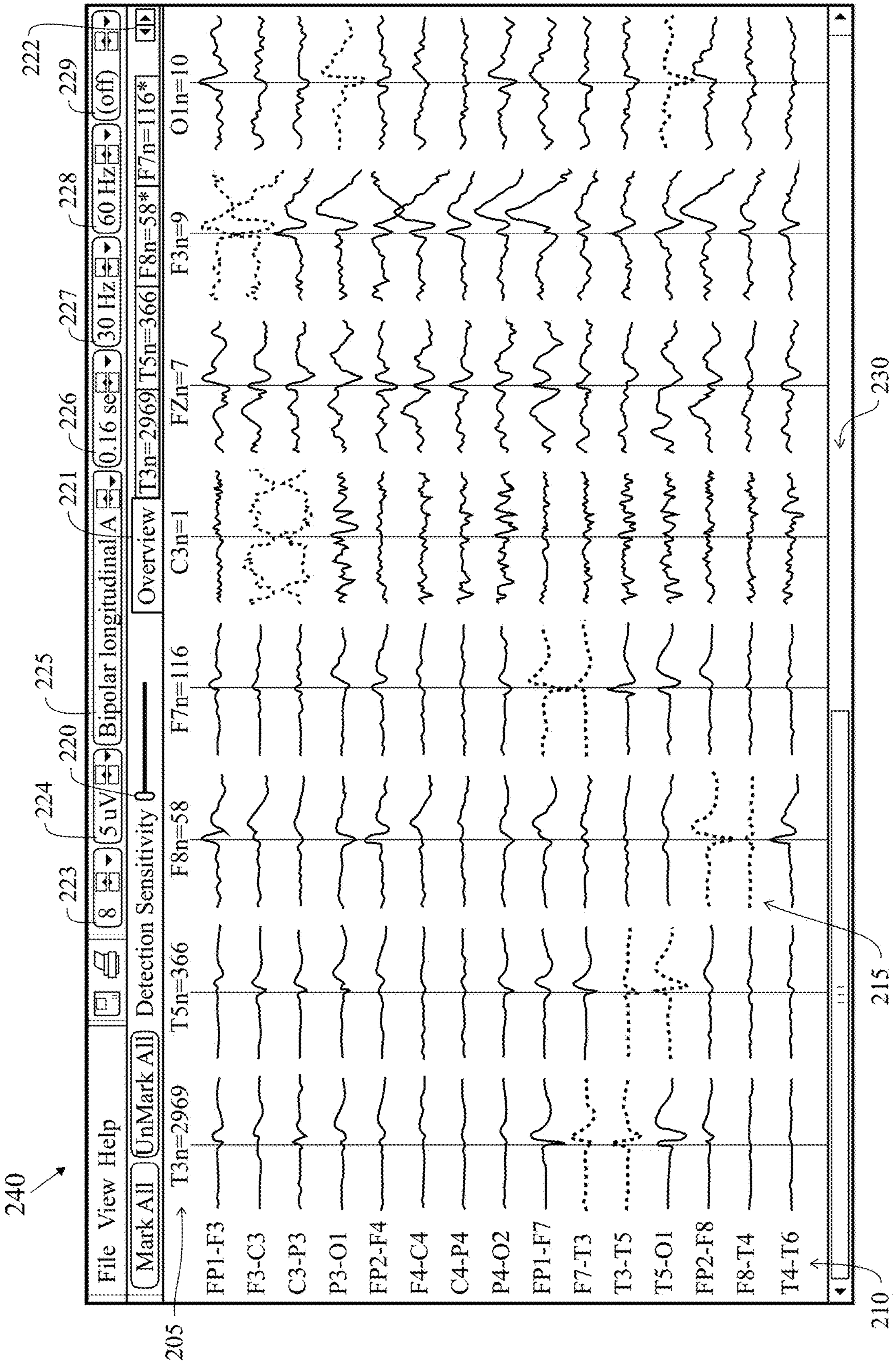
FIG. 28 is an illustration of an analyzed EEG recording.
Figure 29:
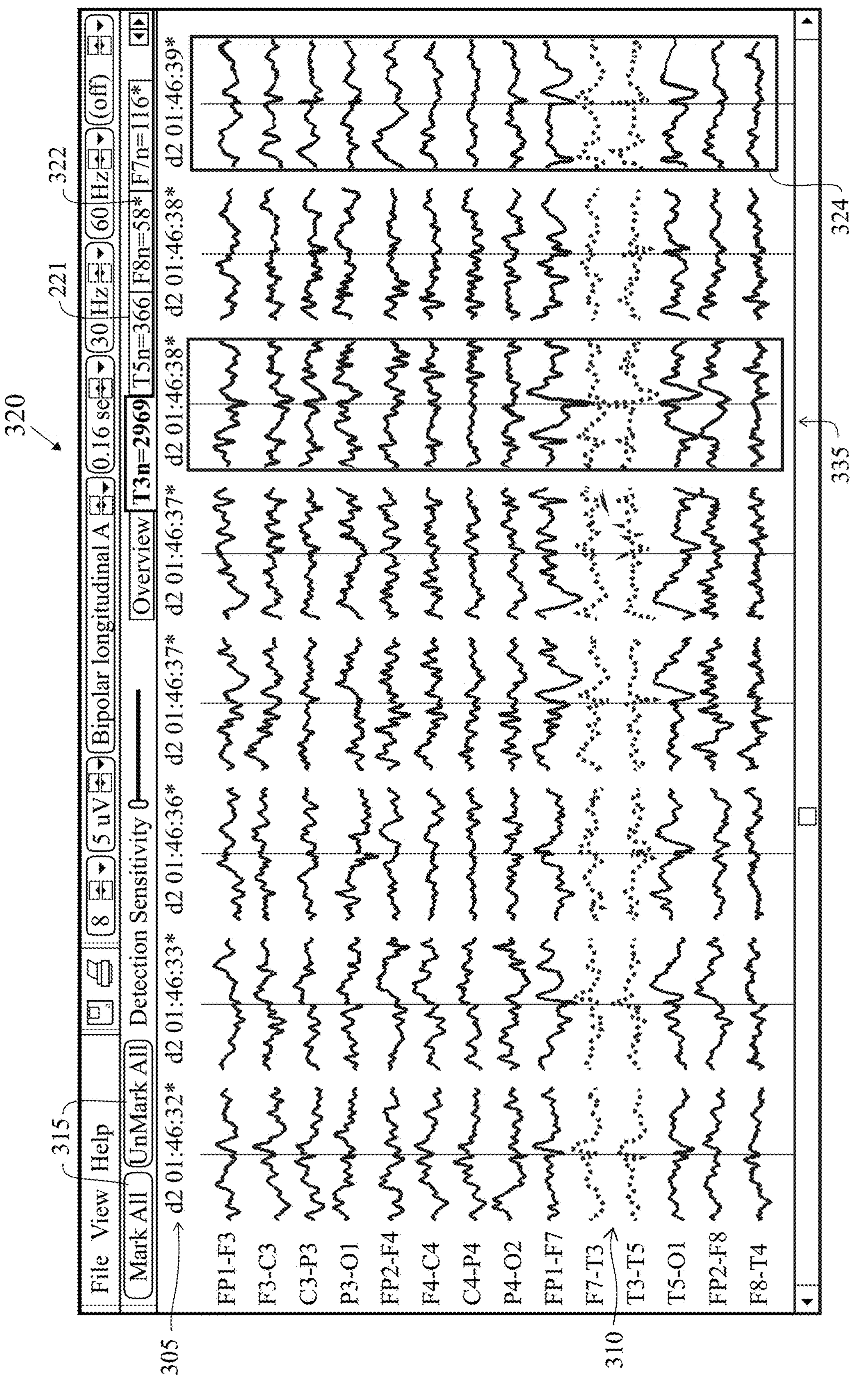
FIG. 29 is an illustration of an analyzed EEG recording.

When the Easy SpikeReview program opens, the Overview window 240 is initially presented, as shown in FIG. 28. The overview depicts averages from the various spike foci detected by a spike detection mechanism. To create these overview averages the spike detections are sorted by detection foci (electrode) and then all detections at a particular focus are mathematically averaged. For example, the first column of EEG represents an average of 2969 events that had their maximum point of detection at the T3 electrode. The columns of the EEG are preferably separated from other columns by a thin band of white. Each EEG column represents a distinct group average. The primary electrode focal point of each average, and the number of detection events incorporated into each average, 205 are shown above the columns of EEG. Channels including the detection focal point electrode are highlighted red 215, (shown in the FIGS. as dotted lines). As with evoked potentials, averaging multiple detections results in an increase in the signal-to-noise ratio and makes it easier to delineate the field of distribution of epileptiform abnormalities.

The various functions of the Easy SpikeReview window include the ability to choose spike detections per page 223, an EEG voltage amplitude selector 224, a montage selector 225, LFF (TC) 226, HFF 227, notch 228, and a custom filter 229. Navigation to other tabs not in the current view is also possible with the forward and back tabs 222. If there's more than one page of Overview averages, clicking on the bottom bar 230 will page forward. Right-clicking on the montage bar 210 will show montage controls.

The sensitivity of the SpikeDetector output can be dynamically adjusted during the review process, which is done by using the detection sensitivity slider 220 that is labeled. When Easy SpikeReview is initially opened, the detection sensitivity slider 220 is set to the far left position. In this position the SpikeDetector neural network algorithms identify sharp transients that have a high probability of being epileptiform abnormalities: these are events the detector assigned a high probability of being a real epileptiform abnormality. The rate of false positive detections at this setting is lowest. Thus, the ratio of true epileptiform signal to false positive noise is highest at this setting. However, some spikes and sharp waves that are less well-formed may not be evident with the slider set at its lowest sensitivity. The detector's sensitivity can be quickly adjusted by dragging the slider 220 towards the right so that it is more sensitive and thus more likely to identify less well-formed or lower amplitude transients. New groups may then appear in the overview display of spike averages. In concert with the increase in true spike detections, there is also an increase in false positive detections.

In records with rare epileptiform abnormalities or those in which the SpikeDetector neural networks, when set to lowest sensitivity, do not recognize the epileptiform abnormalities well, switching to the highest setting on the detection sensitivity slider 220 may allow visualization of real epileptiform abnormalities. In such cases, identifying the rare events often requires assessment of the individual raw detections. This is accomplished by either displaying all raw detections back-to-back following the spike averages on the overview page, or by reviewing the detections at each electrode location, such as in FIG. 29, by progressively selecting the location tabs 221 at the top of the EEG window. Detections that have already been viewed are marked with a trailing asterisk 322 behind the time.

Figure 30:
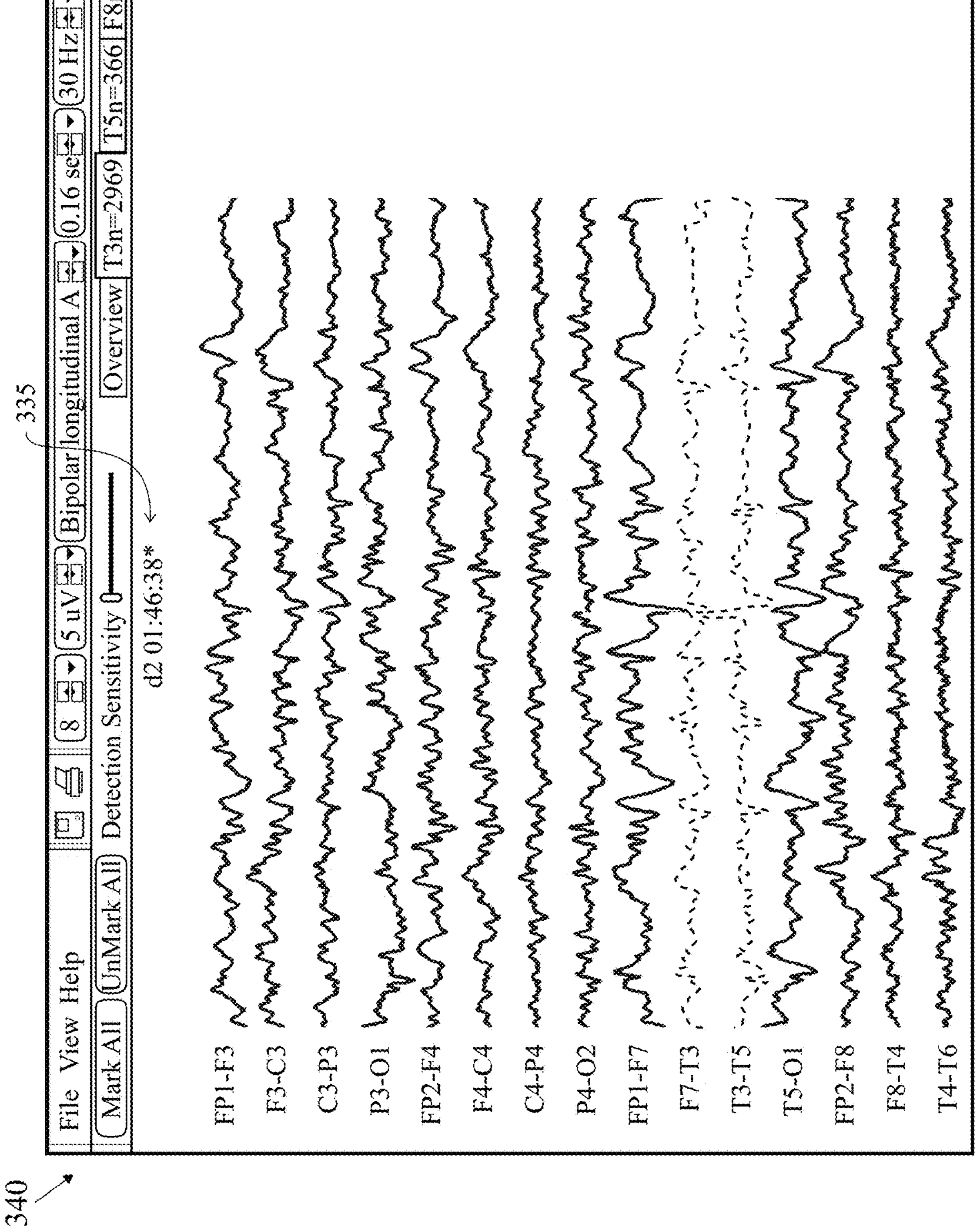
FIG. 30 is an illustration of an analyzed EEG recording.

Clicking on any of the electrode location tabs 221 at the top of the EEG window will display the raw (non-averaged) spike detections 320 that arose from that particular electrode location. The individual detections are separated by a thin band of white, and the detection point is centered in a one second segment of EEG and indicated by a faint vertical gray line with a heading indicating the time of detection 305. Channels containing the electrode involved in the detection are highlighted red 310, (shown in the FIGS. as dotted lines). Left double-clicking with the mouse on any individual detection 335 will cause an expanded EEG view 340, as shown in FIG. 30, of that particular detection 335 to appear. Left double-clicking on the expanded view 340 will return the user to a display of back-to-back individual detections 320.

Figure 31:
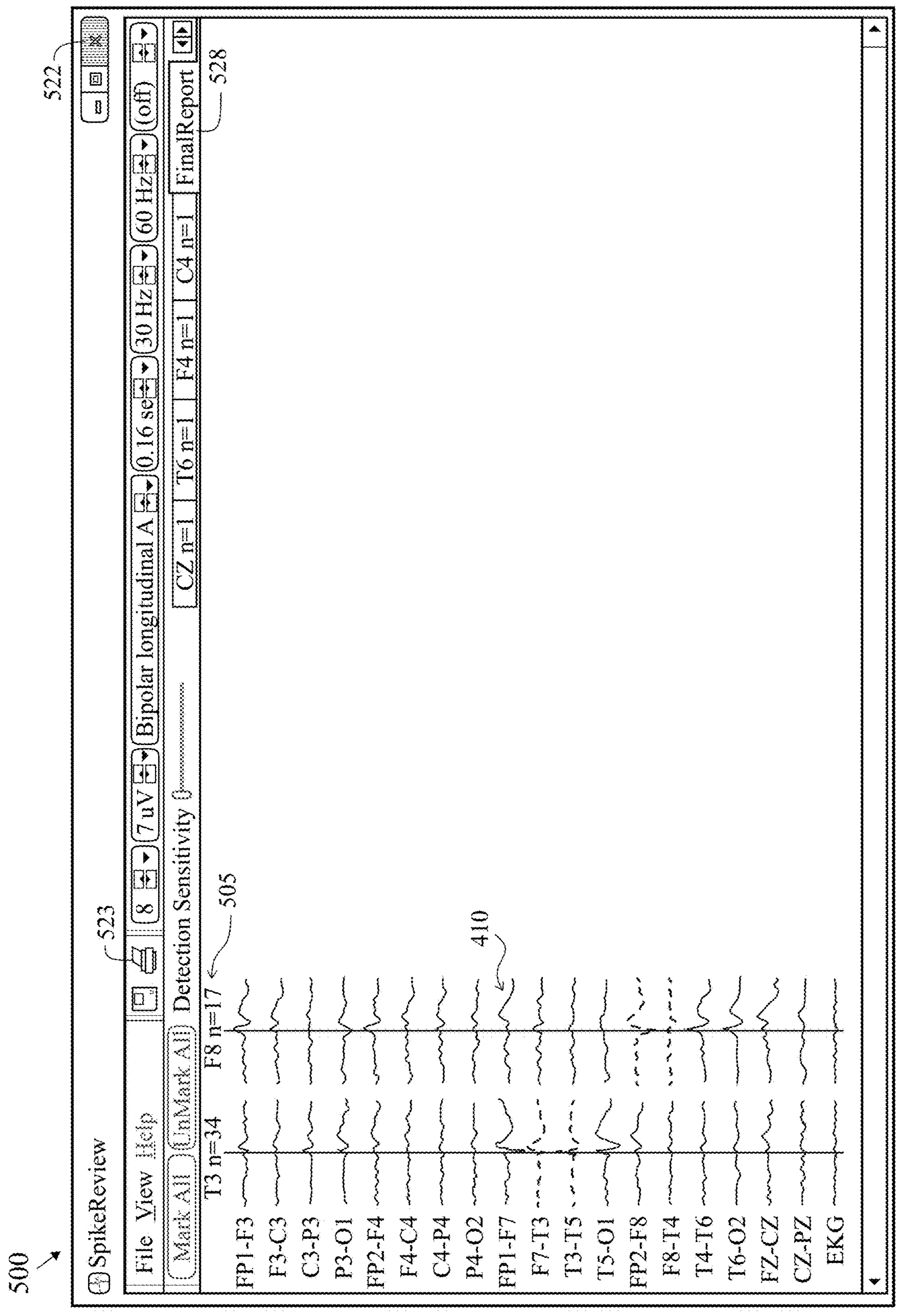
FIG. 31 is an illustration of an analyzed EEG recording.

When viewing individual spike detections (accessed from the tabs 221 above the EEG window), exemplar spikes can be hand-marked by left-clicking with the mouse on the desired example. A rectangle outlining the chosen spike 324 will appear. Marking or unmarking all detections can be done with the Mark All or UnMark All buttons 315 on the toolbar. Hand-marked detections will be included in the spike averages that appear in the FinalReport. These hand-marked events can also be displayed back-to-back, as shown in FIG. 31, immediately following their averages in FinalReport 500, and can be printed 523 for archival purposes or for evaluation by another reviewer.

Figure 32:
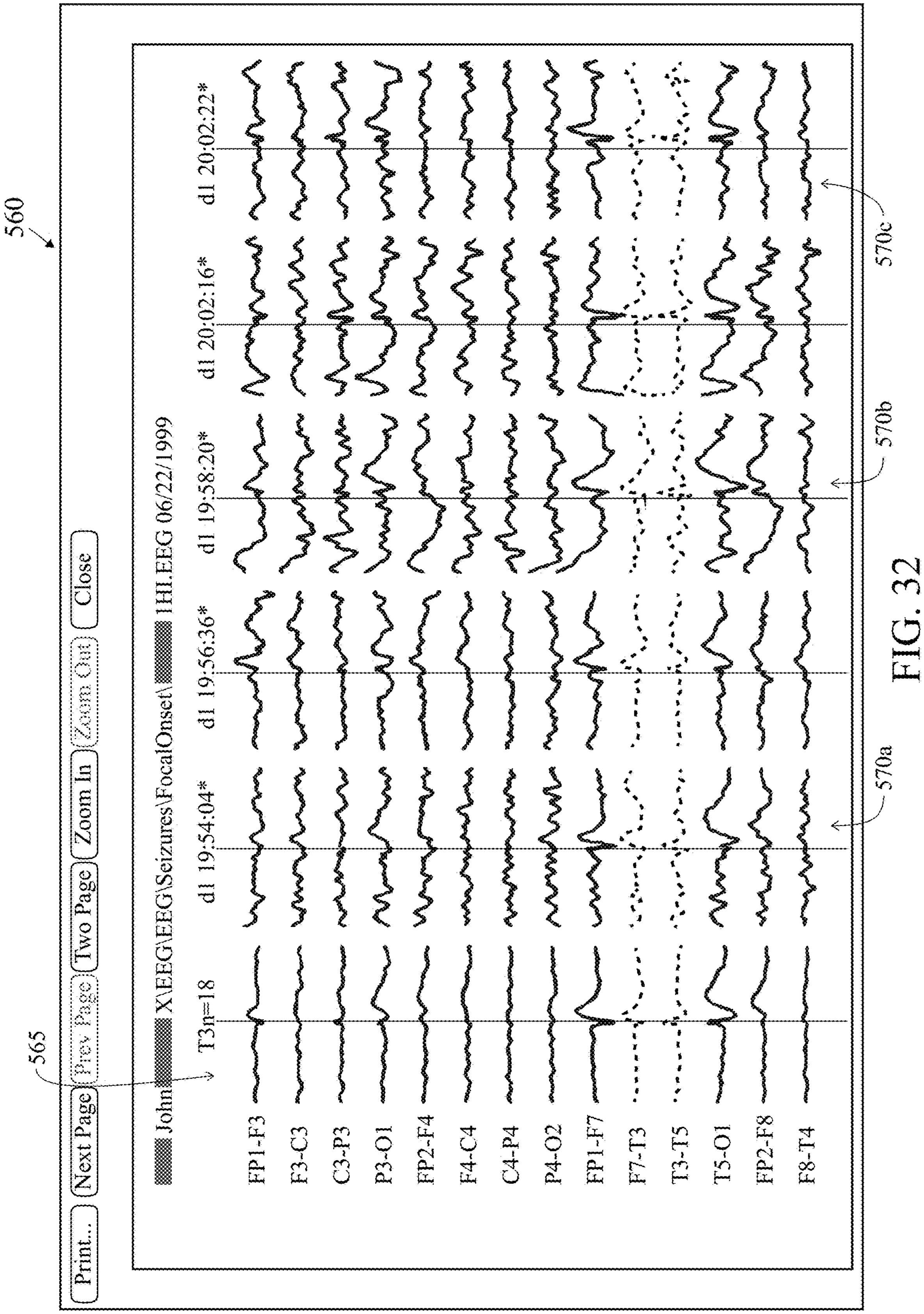
FIG. 32 is an illustration of an analyzed EEG recording.

Clicking on FinalReport tab 528 at the top of the EEG window displays a summary of all hand-marked exemplar spike or sharp waves 410 at the focus 505 chosen. The initial default view shows the mathematical averages of the user-chosen hand-marked events, sorted by electrode focus 505. As explained, head voltage topograms and back-to-back individual user-selected events are displayed by selecting menu options or via right mouse click choices. Voltage topograms are only created when viewing the EEG in a referential montage. FIG. 32 is a print preview view 560 of a FinalReport showing a group average of 18 user-selected spikes 565 and constituent spikes 570*a*-570*c*. Upon exiting 522 the program, all changes are automatically saved, including user marked spikes and viewed events.

Figure 33:
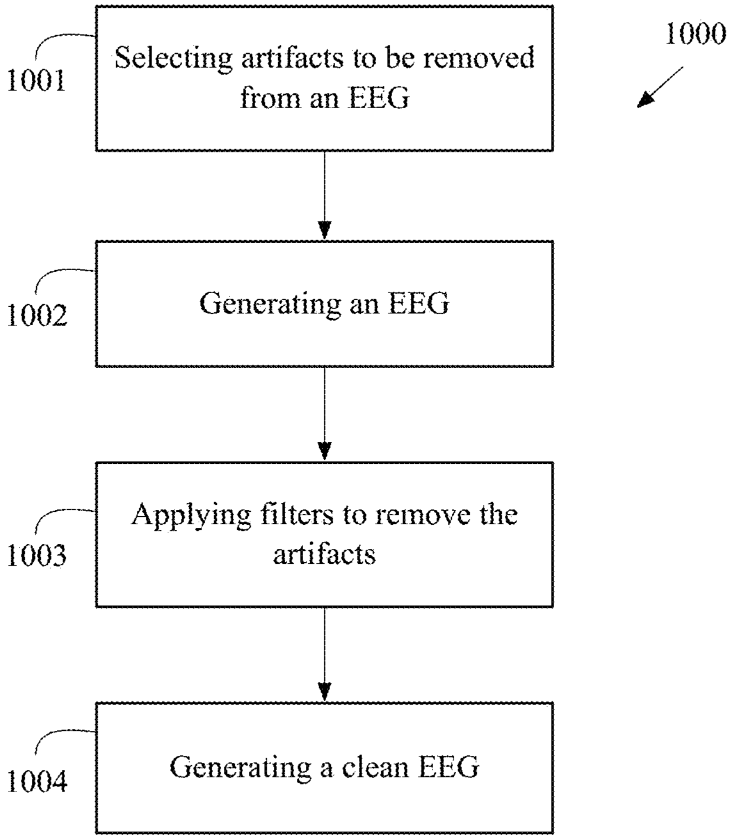
FIG. 33 is a flow chart of a general method for removing artifacts from an EEG recording.

FIG. 33 is a flow chart of a general method 1000 for removing artifacts from an EEG recording. At block 1001, a plurality of artifacts is selected to be automatically removed from an EEG recording using a user interface. At block 1002 an EEG is generated. At block 1003, a plurality of filters is applied to remove the plurality of artifacts from the EEG. At block 1004, a clean EEG is generated.

Figure 34:
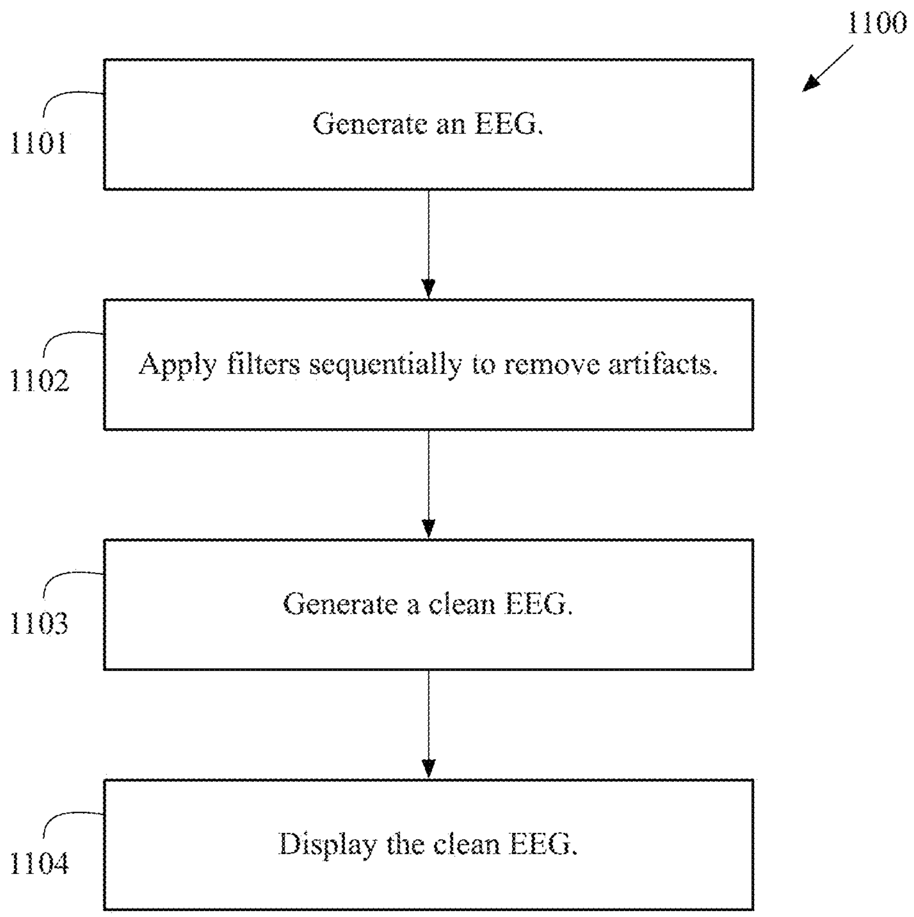
FIG. 34 is a flow chart of a another method for removing artifacts from an EEG recording.

FIG. 34 is a flow chart of another method 1100 for removing artifacts from an EEG recording. At block 1101, an EEG is generated from a machine comprising a plurality of electrodes, an amplifier and processor. At block 1102, multiple filters are applied sequentially to remove artifacts from the EEG. At block 1103, a clean EEG is generated. At block 1104, the clean EEG is displayed.

Figure 35:
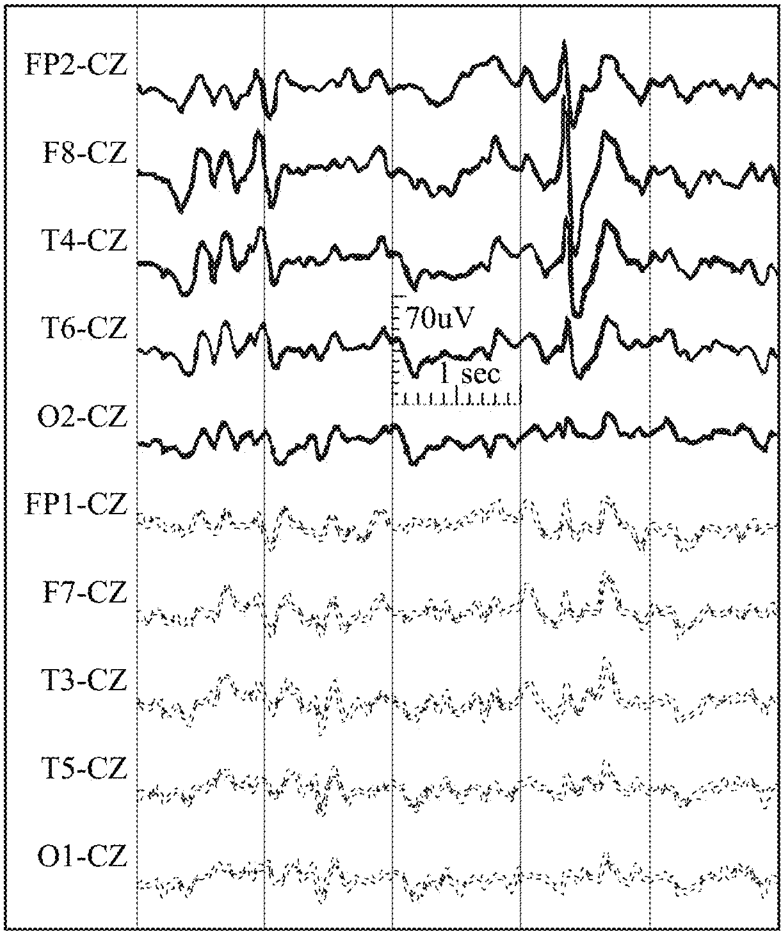
FIG. 35 is an illustration of a CZ reference montage.

FIG. 35 is an illustration of a CZ reference montage 1400.

In one example an algorithm called BSS-CCA is used to remove the effects of muscle activity from the EEG. Using the algorithm on the recorded montage will frequently not produce optimal results. In this case it is generally optimal to use a montage where the reference electrode is one of the vertex electrodes such as CZ in the international 10-20 standard. In this algorithm the recorded montage would first be transformed into a CZ reference montage prior to artifact removal. In the event that the signal at CZ indicates that it is not the best choice then the algorithm would go down a list of possible reference electrodes in order to find one that is suitable.

It is possible to perform BSS-CCA directly on the user-selected montage. However, this has two issues. First, this requires doing an expensive artifact removal process on each montage selected for viewing by the user. Second the artifact removal will vary from one montage to another, and will only be optimal when a user selects a referential montage using the optimal reference. Since a montage that is required for reviewing an EEG is frequently not the same as the one that is optimal for removing artifact this is not a good solution.

An additional description of analyzing EEG recordings is set forth in Wilson et al., U.S. patent application Ser. No. 13/684,469, filed on Nov. 23, 2012, for a User Interface For Artifact RemovalIn An EEG, which is hereby incorporated by reference in its entirety. An additional description of analyzing EEG recordings is set forth in Wilson et al., U.S. patent application Ser. No. 13/684,556, filed on Nov. 25, 2012, for a Method And System For Detecting And Removing EEG Artifacts, which is hereby incorporated by reference in its entirety.

Figure 36:
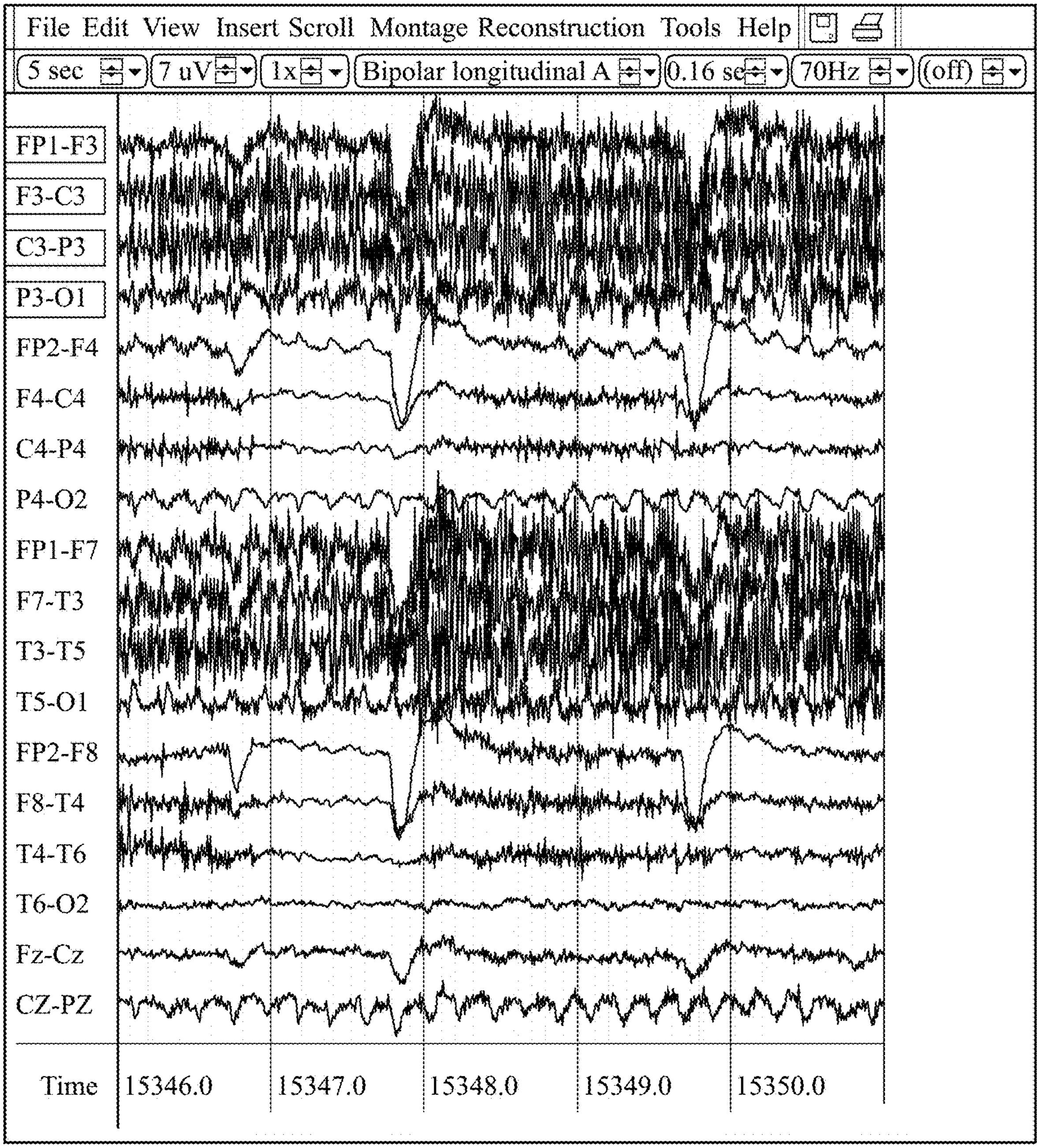
FIG. 36 is an illustration of an EEG recording containing a seizure, a muscle artifact and an eye movement artifact.
Figure 37:
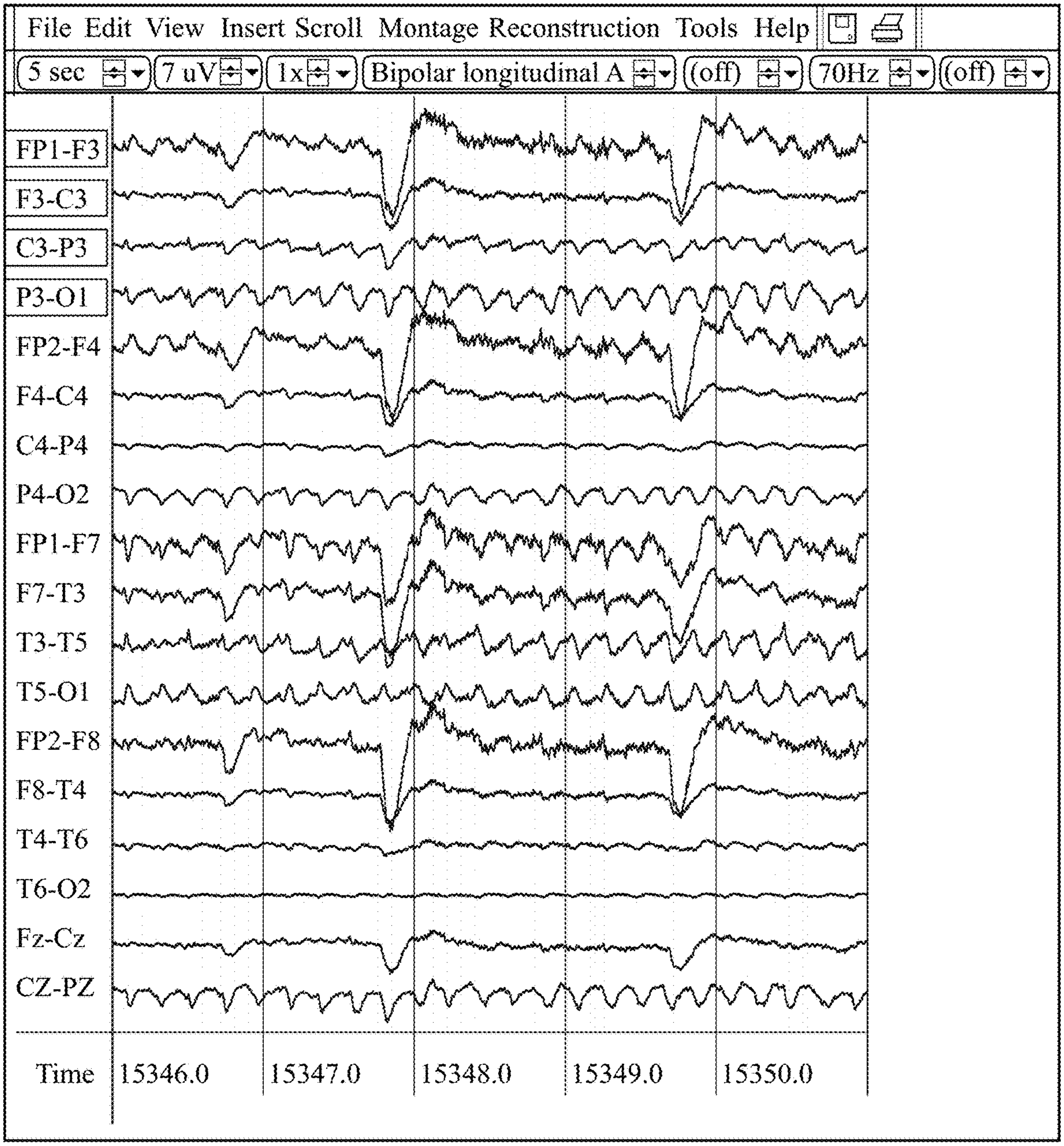
FIG. 37 is an illustration of the EEG recording of FIG. 36 with the muscle artifact removed.
Figure 38:
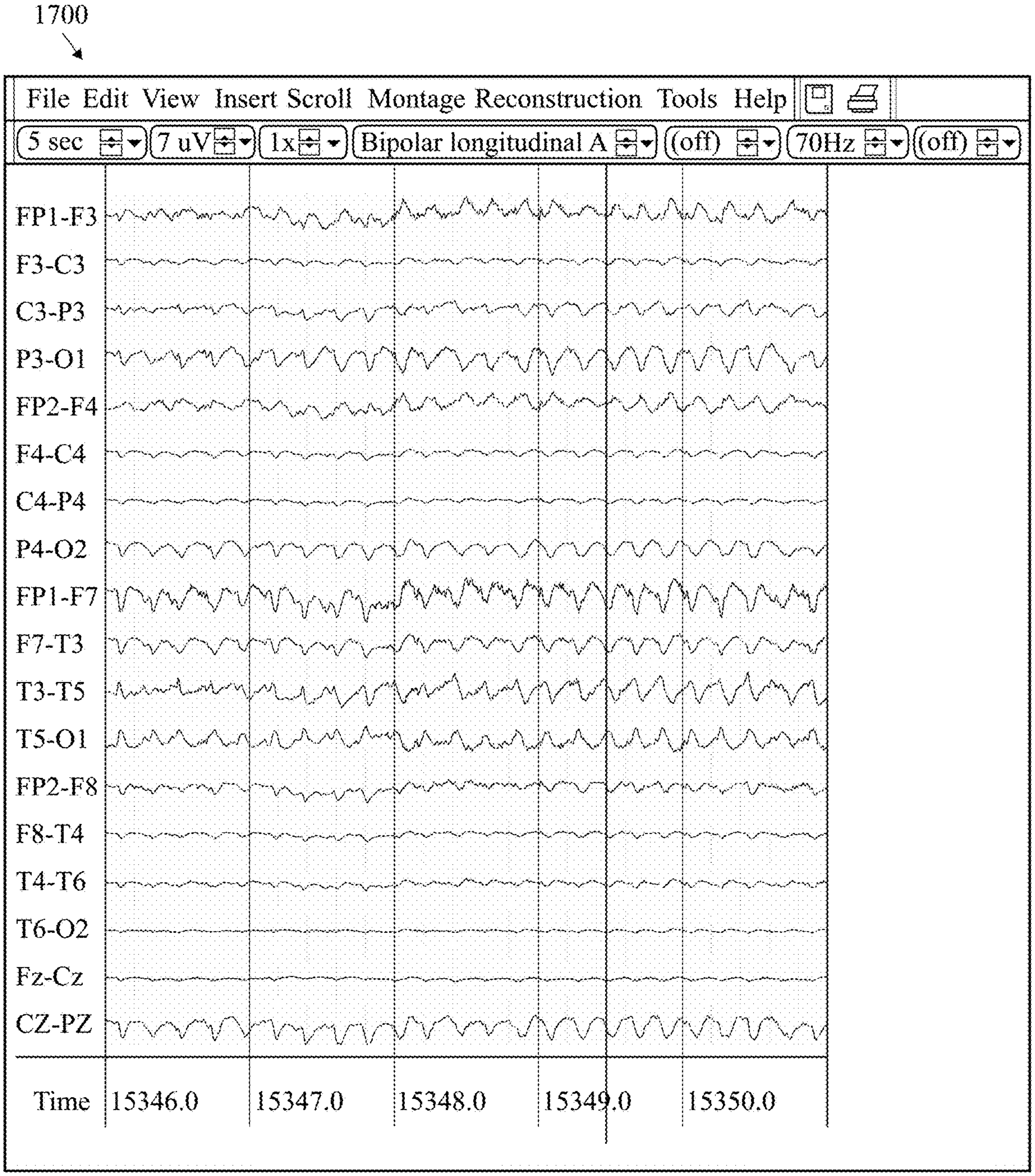
FIG. 38 is an illustration of the EEG recording of FIG. 37 with the eye movement artifact removed.

FIGS. 36-38 illustrate how removing artifacts from the EEG signal allows for a clearer illustration of a brain's true activity for the reader. FIG. 36 is an illustration of an EEG recording containing a seizure, a muscle artifact and an eye movement artifact 1500. FIG. 37 is an illustration of the EEG recording of FIG. 36 with the muscle artifact removed 1600. FIG. 38 is an illustration of the EEG recording of FIG. 37 with the eye movement artifact removed 1700.

Figure 39:
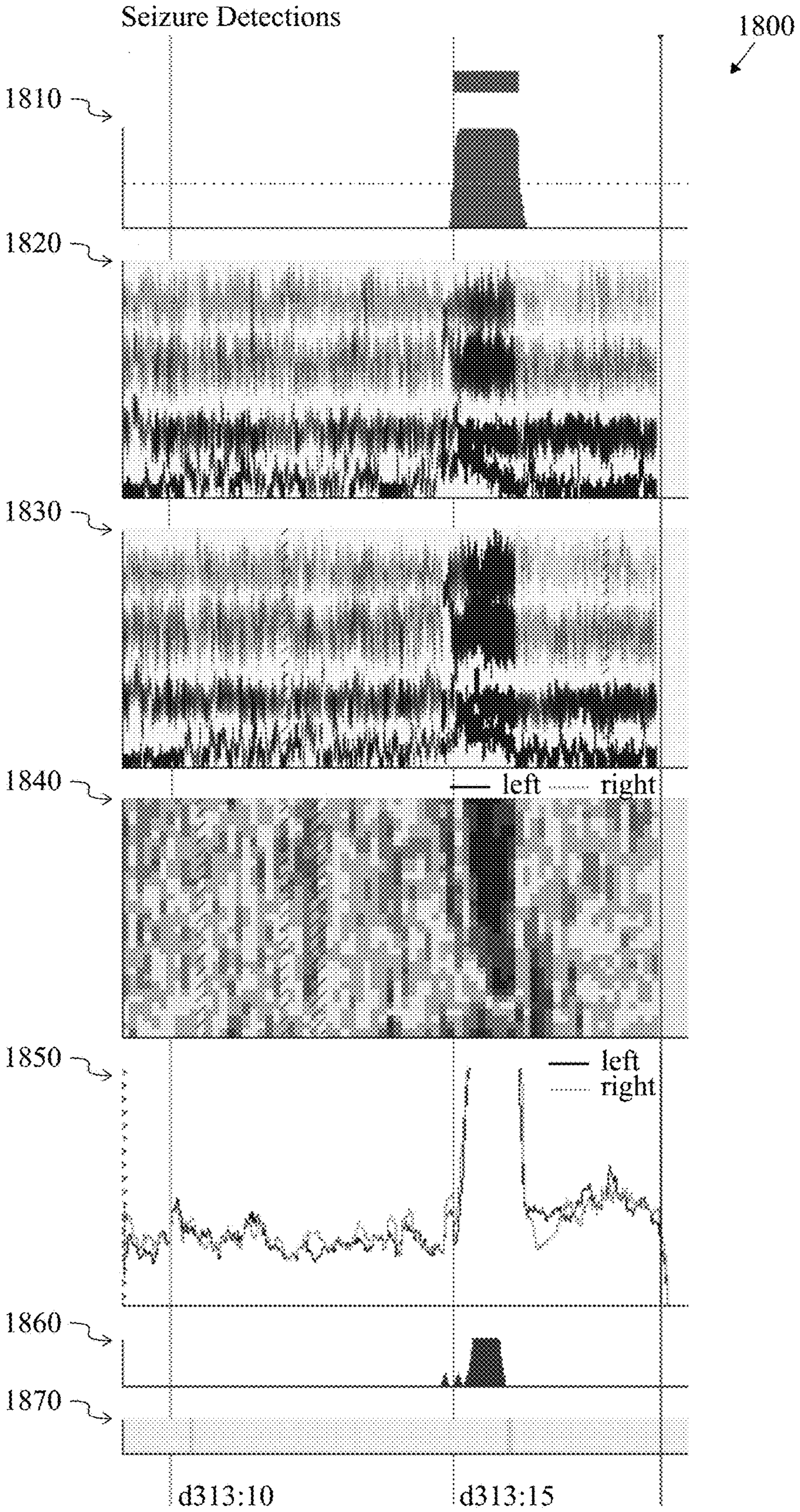
FIG. 39 is an illustration of spike detections indicative of a seizure.
Figure 40:
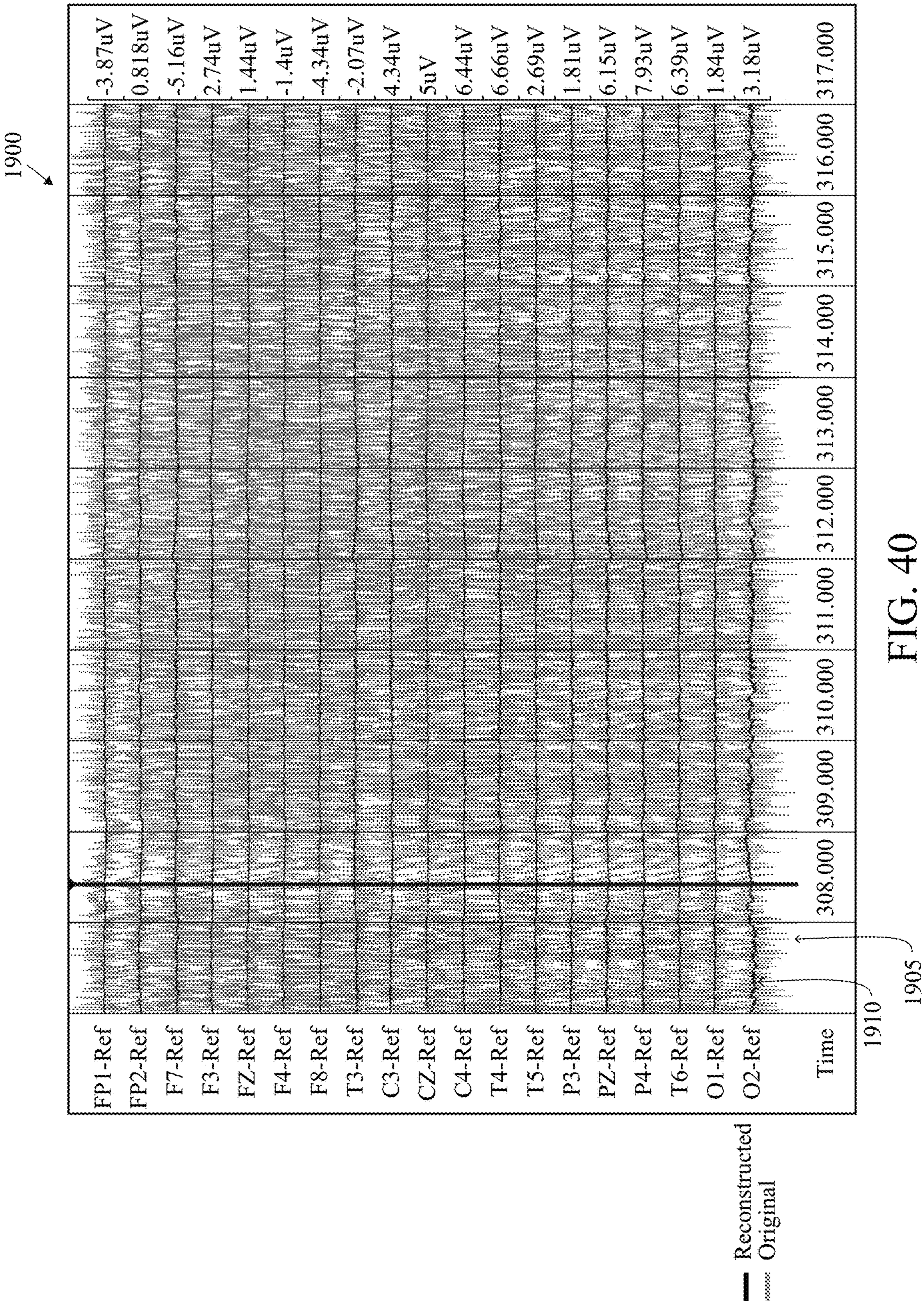
FIG. 40 is an illustration of a paralytic EEG record for a patient for a first time period of the EEG record after removing muscle artifacts using a recorded montage.
Figure 41:
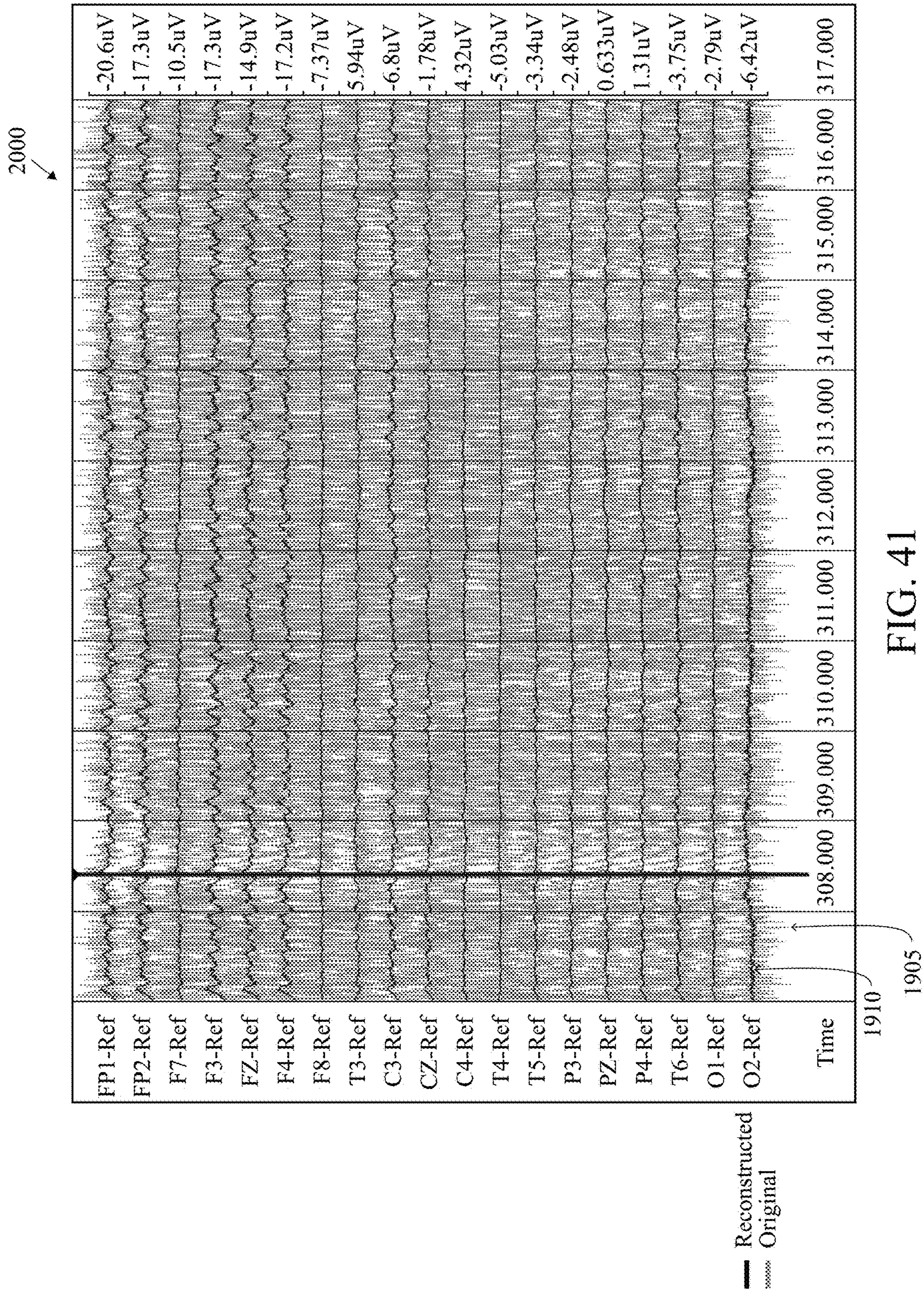
FIG. 41 is an illustration of a paralytic EEG record for a patient for a first time period of the EEG record after removing muscle artifacts using a CZ reference montage.
Figure 42:
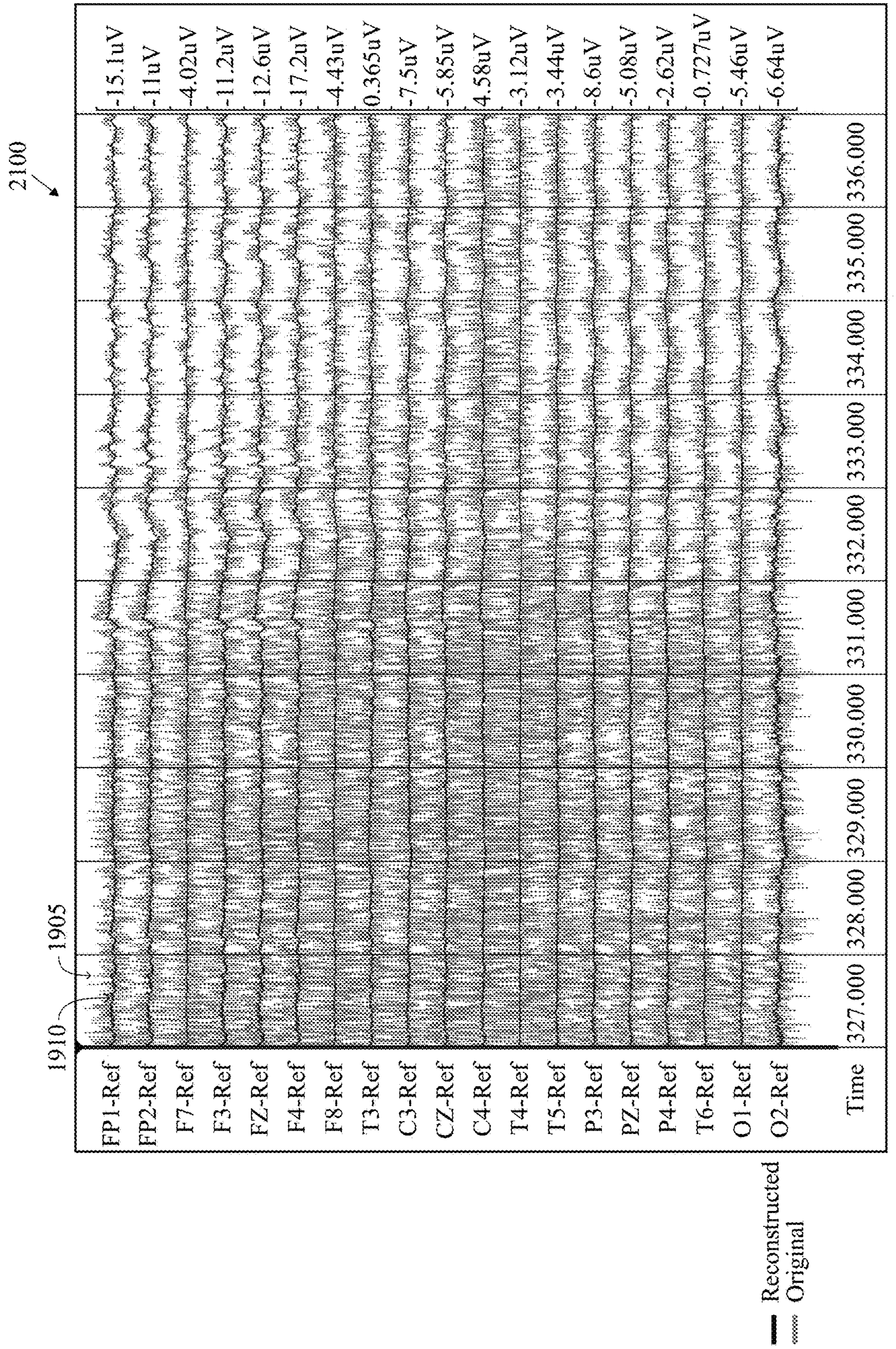
FIG. 42 is an illustration of a paralytic EEG record for a patient for a second time period of the EEG record after removing muscle artifacts using a recorded montage.
Figure 43:
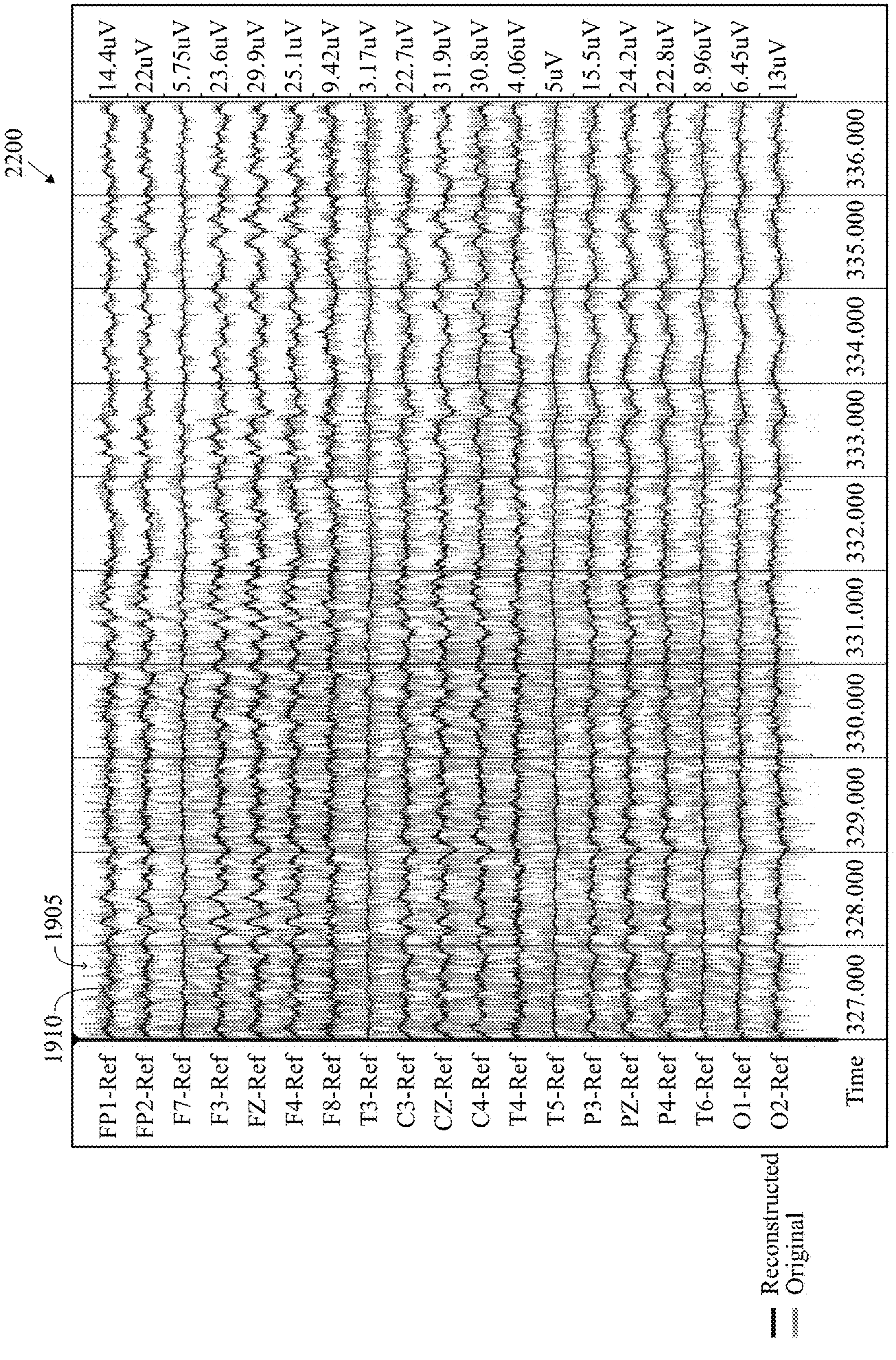
FIG. 43 is an illustration of a paralytic EEG record for a patient for a second time period of the EEG record after removing muscle artifacts using a CZ reference montage.
Figure 44:
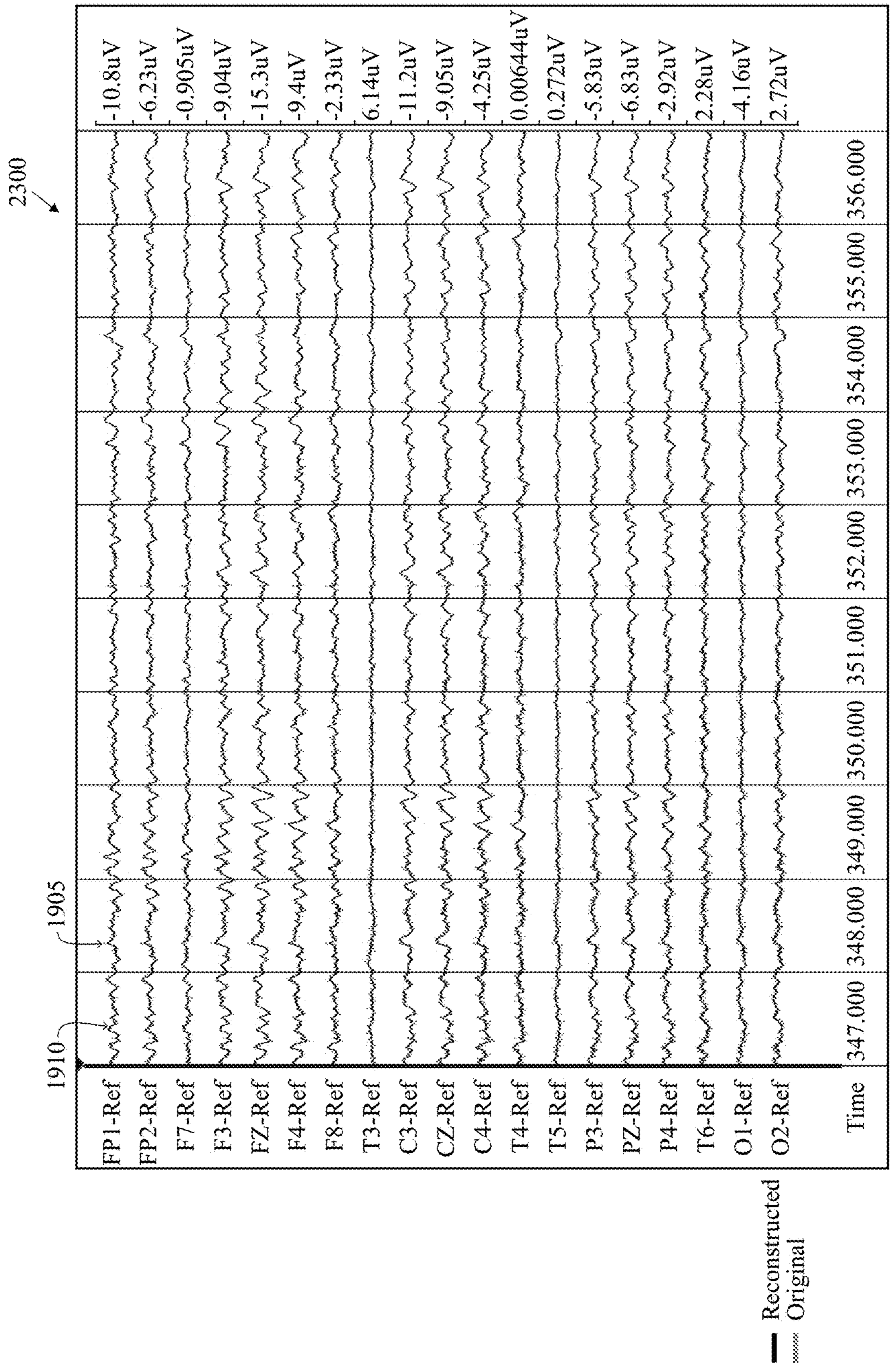
FIG. 44 is an illustration of a paralytic EEG record for a patient for a third time period (the patient has been paralyzed so the muscle activity is absent) of the EEG record after removing muscle artifacts using a recorded montage.
Figure 45:
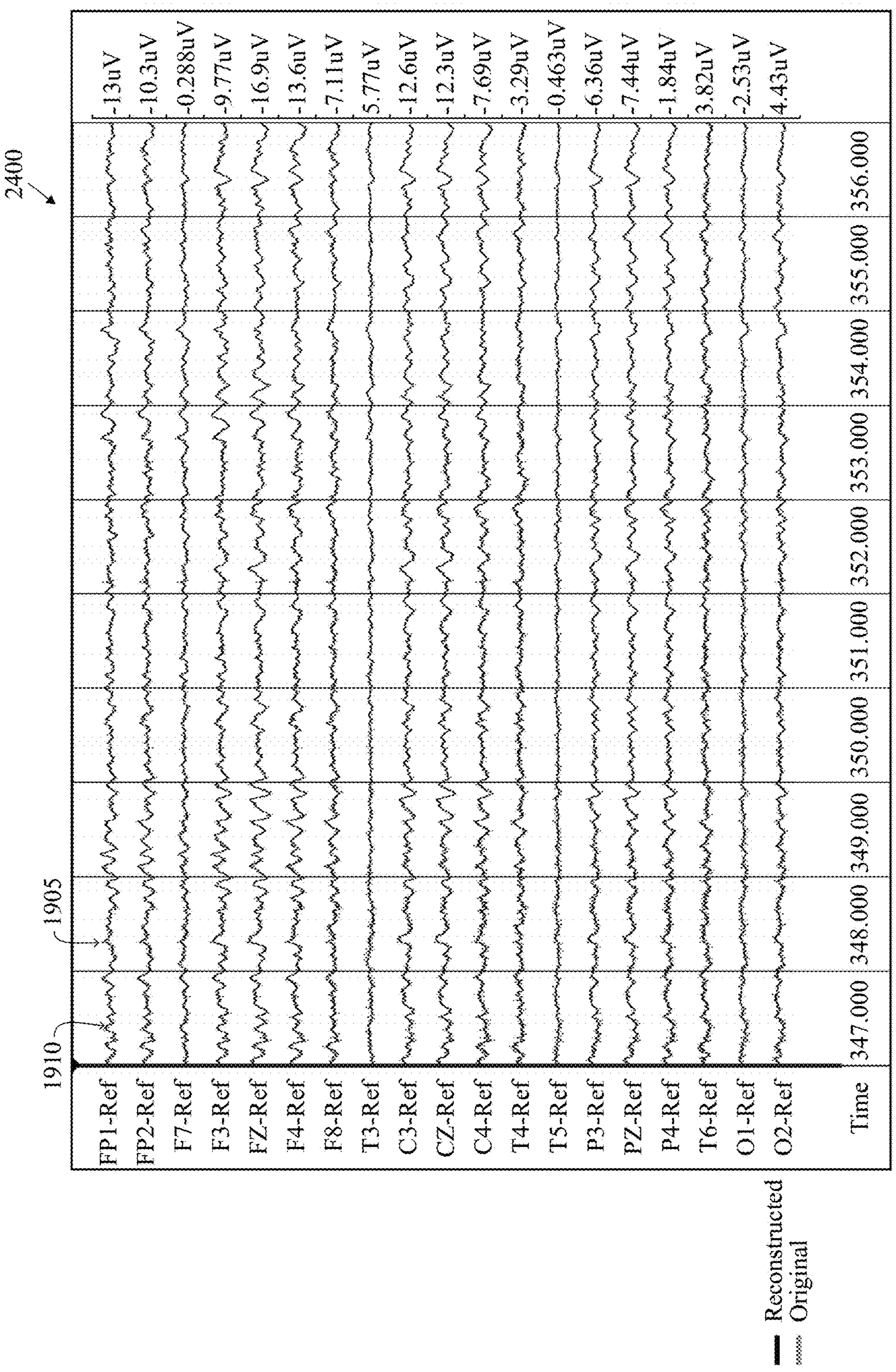
FIG. 45 is an illustration of a paralytic EEG record for a patient for a third time period (the patient has been paralyzed so the muscle activity is absent) of the EEG record after removing muscle artifacts using a CZ reference montage.

FIG. 39 is an illustration of spike detections indicative of a seizure 1800. Seizure probability 1810; Rhythmicity Spectrogram, left hemisphere, 1-25 Hz 1820; Rhythmicity Spectrogram, right hemisphere, 1-25 Hz 1830; Relative Asymmetry Spectrogram, Hemispheric, 0-18 Hz 1840; Peak Envelope, hemispheric, 2-20 Hz 1850; Spike Detections (count per 5 second epoch) 1860; and Chewing Artifact Probability 1870.

FIGS. 40 31, 42 33, and 44 35 are illustrations of a paralytic EEG record for a patient for three time periods (at the third time period the patient has been paralyzed so the muscle activity is absent 2300) of an EEG record after removing muscle artifacts using a recorded montage. FIGS. 41 32, 43 34, and 45 36 are illustrations of a paralytic EEG record for a patient for three time periods (at the third time period the patient has been paralyzed so the muscle activity is absent 2400) of an EEG record after removing muscle artifacts using a CZ reference montage. The red is the original signal 1905 (shown in the FIGS. as gray) and the black is the reconstruction 1910 (shown in the FIGS. as black). Using the recorded montage, all of the brain activity is removed and the black reconstruction appears almost flat 1900, 2100, 2300. However, using the CZ reference montage, the brain activity is retained and appears in the first two time periods 2000, 2200 similar to the third time period 2400 when the patient is paralyzed.

Various artifact removal techniques are explained in U.S. Provisional Patent Application Nos. 61/563,807, 61/563,751, 61/563,755, 61/563,731, 61/563,767 61/563,776, 61/563,796, and 61/563,828, which are all hereby incorporated by reference in their entireties.

Figure 46:
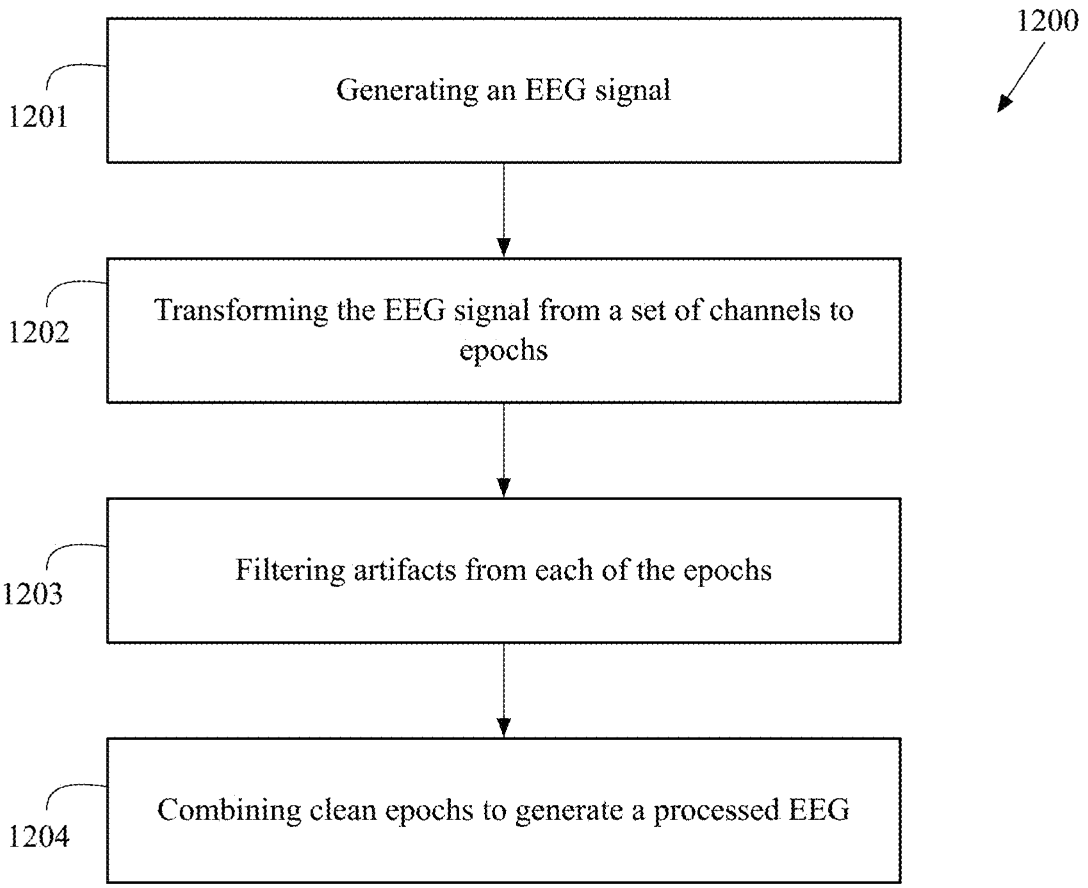
FIG. 46 is a flow chart of a general method for filtering artifacts from an EEG signal.

FIG. 46 is a flow chart of a general method 1200 for filtering artifacts from an EEG signal. At block 1201, an EEG signal is generated from a machine comprising a plurality of electrodes, an amplifier and processor. At block 1202, the EEG signal is transformed from a set of channels into a plurality of epochs. At block 1203, artifacts from each of the plurality of epochs are filtered using an artifact removal algorithm to generate a plurality of clean epochs. At block 1204, the clean epochs are combined to generate a processed EEG recording.

Each of the plurality of epochs has an epoch duration length of two seconds and an increment of one second. Alternatively, each of the plurality of epochs has an epoch duration length of four seconds and an increment of two seconds.

The artifact removal algorithm is preferably a blind source separation algorithm. The blind source separation algorithm is preferably a CCA algorithm or an ICA algorithm.

The clean epochs are preferably combined using a weighted average and the weight of the weighted average is preferably proportional to the ratio of the distance to an epoch center.

Figure 47:
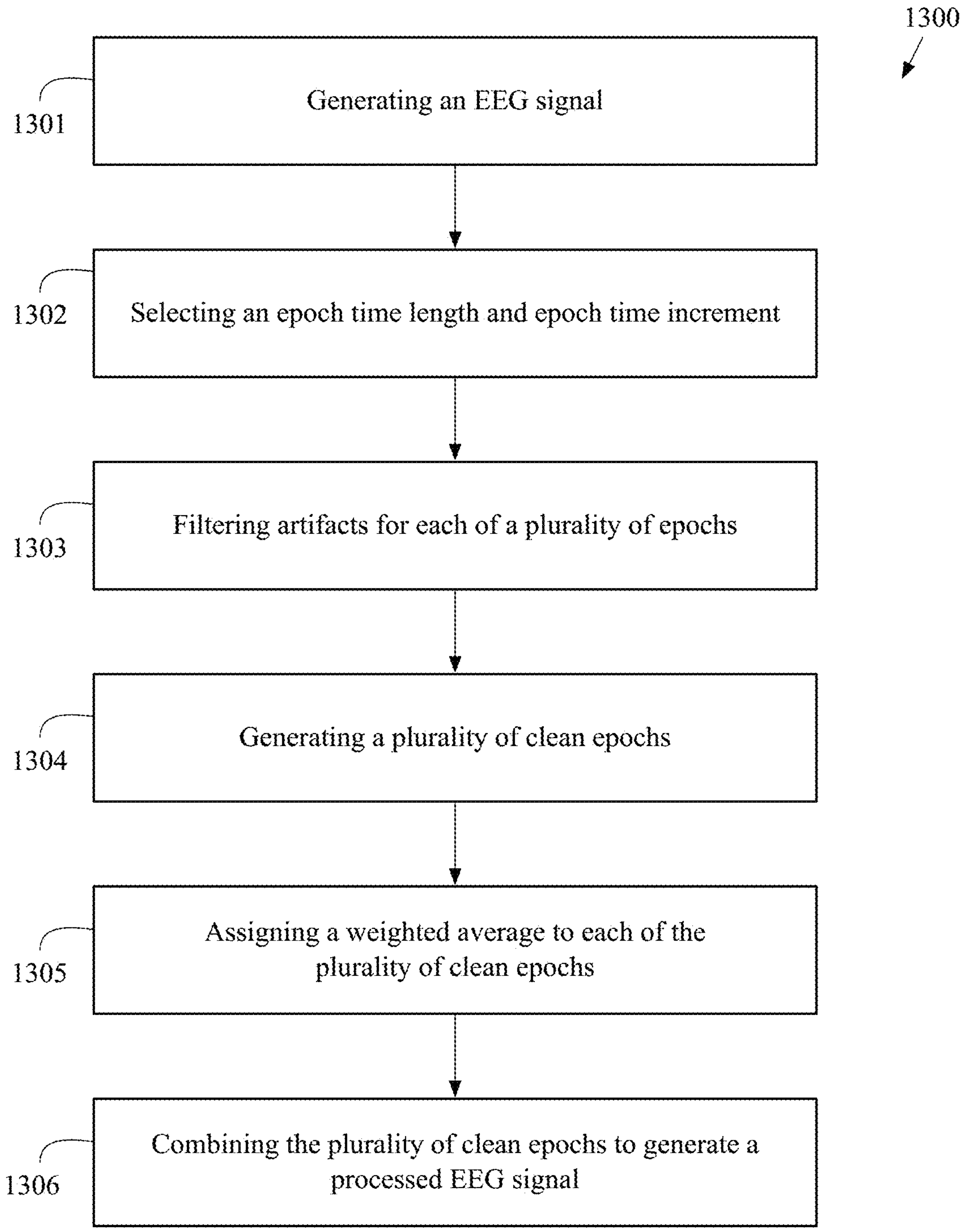
FIG. 47 is a flow chart of a specific method for filtering artifacts from an EEG signal.

FIG. 47 is a flow chart of a specific method 1300 for filtering artifacts from an EEG signal. At block 1301, an EEG signal is generated from a machine. At block 1302, an epoch time length and an epoch time increment are selected for the EEG signal. At block 1303, artifacts from each of the plurality of epochs are filtered using an artifact removal algorithm. At block 1304, a plurality of clean epochs is generated from the artifact removed epochs. At block 1305, a weighted average is assigned to each of the plurality of clean epochs. At block 1306, the clean epochs are combined to generate a processed EEG recording.

Each of the plurality of epochs has an epoch duration length of two seconds and an increment of one second. Alternatively, each of the plurality of epochs has an epoch duration length of four seconds and an increment of two seconds.

The artifact removal algorithm is preferably a blind source separation algorithm. The blind source separation algorithm is preferably a CCA algorithm or an ICA algorithm.

The clean epochs are preferably combined using a weighted average and the weight of the weighted average is preferably proportional to the ratio of the distance to an epoch center.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim.

Therefore, the embodiments of the invention in which an exclusive property or privilege is claimed are defined in the following appended claims.

We claim as our invention:

1. A method for removing artifacts in an electroencephalogram (EEG) recording, the method comprising:
   generating an EEG recording from a machine comprising
      a plurality of electrodes for generating a plurality of EEG signals,
      at least one amplifier connected to each of the plurality of electrodes by a plurality of wires to amplify each of the plurality of EEG signals,
      a processor connected to the amplifier to generate an EEG recording from the plurality of EEG signals,
      wherein the processor is configured to execute a spike review program to the EEG recording to detect a plurality of spikes on the EEG recording, and a spike detector neural network algorithms to identify sharp transients to determine a probability of being epileptiform abnormalities as a epileptiform abnormality; and
      a display connected to the processor for displaying an EEG recording;
   displaying the EEG recording on the display, the EEG recording comprising a plurality of artifacts wherein the plurality of artifacts comprises at least two of a muscle artifact, an eye movement artifact, an electrical artifact, a heartbeat artifact, a tongue movement artifact, and a chewing artifact;
   selecting at least one of the plurality of artifacts to automatically be removed from the EEG recording using a user interface on the display;
   triggering a button on a computer display to apply at least one filter of a plurality of filters to remove the at least one artifact of the plurality of artifacts from the EEG recording, wherein the button is a keyboard button or a touchscreen button, and wherein the processor is configured to apply at least one filter program to remove a filter from the EEG recording; and
   generating a filtered EEG recording on the display for viewing.

2. The method according to claim 1 further comprising selecting colors for traces and the amount of darkness.

3. A method for removing artifacts in an electroencephalogram (EEG) recording, the method comprising:
   generating an EEG recording from a machine comprising
      a plurality of electrodes for generating a plurality of EEG signals,
      at least one amplifier connected to each of the plurality of electrodes by a plurality of wires to amplify each of the plurality of EEG signals,
      a processor connected to the amplifier to generate an EEG recording from the plurality of EEG signals,
      wherein the processor is configured to execute a spike review program to the EEG recording to detect a plurality of spikes on the EEG recording, and spike detector neural network algorithms to identify sharp transients to determine a probability of being epileptiform abnormalities as a epileptiform abnormality; and
      a display connected to the processor for displaying an EEG recording;
   displaying the EEG recording on the display, the EEG recording comprising a plurality of artifacts wherein the plurality of artifacts comprises at least two of a muscle artifact, an eye movement artifact, an electrical artifact, a heartbeat artifact, a tongue movement artifact, and a chewing artifact;
   filtering the EEG recording to remove a first artifact to generate a first filtered EEG recording to replace the EEG recording on the display, wherein the processor is configured to apply a first filter program to the EEG recording;
   filtering the first filtered EEG recording to remove a second artifact to generate a second filtered EEG recording to replace the first filtered EEG recording on the display wherein the processor is configured to apply a second filter program to the EEG recording;
   filtering the second filtered EEG recording to remove a third artifact to generate a third filtered EEG recording to replace the second filtered EEG recording on the display wherein the processor is configured to apply a third filter program to the EEG recording;
   filtering the third filtered EEG recording to remove a fourth artifact to generate a fourth filtered EEG recording to replace the third filtered EEG recording on the display wherein the processor is configured to apply a fourth filter program to the EEG recording; and
   generating a clean EEG recording for viewing from a last filtered EEG recording,
   wherein each of the first artifact, the second artifact, the third artifact and the fourth artifact is selected from the group comprising muscle artifact, eye movement artifact, electrical artifact, heartbeat artifact, tongue movement artifact, and chewing artifact.

4. A non-transitory computer-readable medium that stores a program that causes a processor to perform functions for removing artifacts in an electroencephalogram (EEG) recording by executing the following steps:
   generating an EEG recording from a machine comprising
      a plurality of electrodes for generating a plurality of EEG signals,
      at least one amplifier connected to each of the plurality of electrodes by a plurality of wires to amplify each of the plurality of EEG signals,
      a processor connected to the amplifier to generate an EEG recording from the plurality of EEG signals,
      wherein the processor is configured to execute a spike review program to the EEG recording to detect a plurality of spikes on the EEG recording, and spike detector neural network algorithms to identify sharp transients to determine a probability of being epileptiform abnormalities as a epileptiform abnormality; and
      a display connected to the processor for displaying an EEG recording;
   displaying the EEG recording on the display, the EEG recording comprising a plurality of artifacts wherein the plurality of artifacts comprises at least two of a muscle artifact, an eye movement artifact, an electrical artifact, a heartbeat artifact, a tongue movement artifact, and a chewing artifact;
   selecting at least one of the plurality of artifacts to automatically be removed from the EEG recording using a user interface on the display;
   triggering, through use of a mouse, a button on a computer display to apply at least one filter of a plurality of filters to remove the at least one artifact of the plurality of artifacts from the EEG recording, and wherein the processor is configured to apply at least one filter program to remove a filter from the EEG recording; and
   generating a filtered EEG recording on the display for viewing.

* * * * *